United States Patent [19]

Moon et al.

[11] 4,072,498
[45] Feb. 7, 1978

[54] PYRAZOLE AMIDES

[75] Inventors: Malcolm W. Moon; Gabriel Kornis, both of Kalamazoo, Mich.

[73] Assignee: The Upjohn Company, Kalamazoo, Mich.

[21] Appl. No.: 686,548

[22] Filed: May 14, 1976

Related U.S. Application Data

[63] Continuation-in-part of Ser. No. 524,231, Nov. 15, 1974, abandoned.

[51] Int. Cl.$^2$ .................. A01N 9/22; C07D 231/16; C07D 231/12
[52] U.S. Cl. ............................. 71/92; 71/90; 260/293.7; 544/140; 548/369; 548/374; 548/375; 548/376; 548/377; 548/378
[58] Field of Search ............. 260/310 R, 293.7; 71/92, 90, 94; 548/372, 374, 375, 376, 377, 378, 369

[56] References Cited

U.S. PATENT DOCUMENTS

| | | |
|---|---|---|
| 3,625,953 | 12/1971 | Rutz .................. 71/92 |
| 3,855,236 | 12/1974 | Kornis ................ 71/92 |

OTHER PUBLICATIONS

Jones et al., J. Org. Chem., vol. 19, pp. 1428–1434, 1954.
Kornis et al., C. A., vol. 75, 129808x.
Talbert et al., C. A., vol. 76, 122780u.

*Primary Examiner*—Natalie Trousof
*Assistant Examiner*—Jane T. Fan
*Attorney, Agent, or Firm*—Bruce Stein; John J. Killinger; Roman Saliwanchik

[57] ABSTRACT

The present invention discloses amides and thioamides substituted in the $\alpha$ or $\beta$ position with substituted pyrazoles which are useful as herbicides.

122 Claims, No Drawings

PYRAZOLE AMIDES

CROSS REFERENCE TO RELATED APPLICATION

This application is a continuation in part of application Ser. No. 524,231, filed Nov. 15, 1974.

BRIEF DESCRIPTION OF THE INVENTION

This invention concerns novel compounds of formula I which are useful in agriculture as herbicides. The compounds are formulated with carriers to prepare compositions which can be applied as pre- and post-emergent herbicides.

DETAILED DESCRIPTION OF THE INVENTION

The invention relates to substituted pyrazoles of the formula:

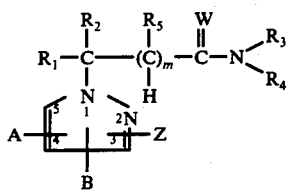

where $R_1$ is hydrogen, alkyl of 1 to 7 carbon atoms, inclusive, haloalkyl of 1 to 7 carbon atoms, inclusive, phenyl, benzyl or cycloalkyl of 3 to 6 carbon atoms, inclusive, with the proviso that when $R_1$ is benzyl or cycloalkyl, $m = 0$; $R_2$ and $R_5$ are the same or different and are hydrogen, halogen, alkyl of 1 to 6 carbon atoms, inclusive, haloalkyl of 1 to 6 carbon atoms, inclusive, or phenyl; $R_1$ and $R_2$ together with the attached carbon atom can be cycloalkyl of 3 to 6 carbon atoms, inclusive, when $m = 0$; $m$ is 0 or 1 provided that when $m = 0$, $R_1$ is not hydrogen and when $m = 1$ at least one of $R_2$ or $R_5$ is hydrogen; $R_3$ is hydrogen, alkyl of from 1 to 8 carbon atoms, inclusive, phenyl or benzyl; $R_4$ is hydrogen, or alkyl of from 1 to 6 carbon atoms, inclusive, and $R_3$ and $R_4$ can be joined together to form a heterocyclic ring selected from the group consisting of morpholine, pyrrolidine or piperidine; A and B are the same or different and are hydrogen, alkyl of from 1 to 6 carbon atoms, inclusive, phenyl, halogen, cyano, haloalkyl of 1 to 6 carbon atoms, inclusive, alkoxy or alkylthio in which the alkyl group is from 1 to 3 carbon atoms, inclusive, or trifluoromethyl and when adjacent can be joined to form a ring of from 5 to 7 carbon atoms, inclusive; Z is selected from the group consisting of

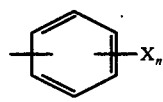

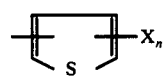

or

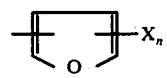

wherein X is halogen, nitro, cyano, acetyl, dimethylcarbamoyl, alkyl, haloalkyl, alkoxy or carboalkoxy in which the alkyl group is from 1 to 3 carbon atoms, inclusive, phenyl, benzyl, 2-phenylethyl and $n$ is 0, 1, or 2; W is selected from the group consisting of oxygen and sulfur; or an acid addition salt thereof which are useful in agriculture as herbicides.

Also disclosed are compounds of the formula:

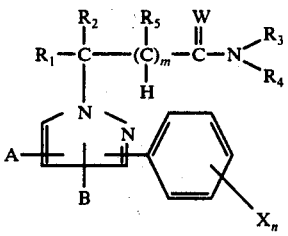

Further disclosed are compounds of the formula:

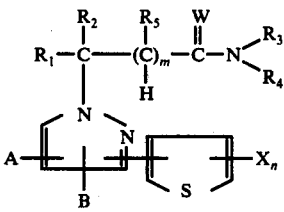

Other substituted pyrazole herbicides disclosed are of the formula:

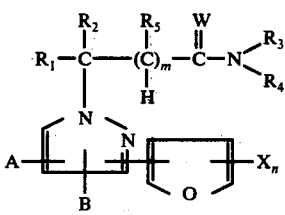

In formulas II thru IV $R_1$, $R_2$, $R_3$, $R_4$, $R_5$, A, B, W, X, $m$ and $n$ are as defined previously. Also disclosed are the acid addition salts of the compounds of formulas II thru IV.

It is preferred that Z be phenyl, formula II. It is preferred that when Z is phenyl that it be attached at the 3 position of the pyrazole group.

It is preferred that the pyrazole group be attached to the α position of the amide or thioamide from the 1 position of the pyrazole group. It is preferred $R_3$ and $R_4$ are alkyl of from 1 to 3 carbon atoms, inclusive. It is preferred X be halogen, alkyl or alkoxy when present.

Disclosed is a method for controlling weeds or undesirable vegetation which comprises applying to the locus thereof a herbicidally effective amount of a compound of the formula:

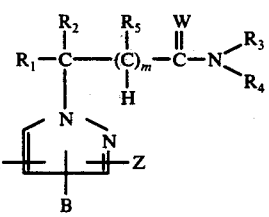

Further disclosed is a method for controlling weeds or undesirable vegetation which comprises applying to the locus thereof a herbicidally effective amount of a compound of the formula:

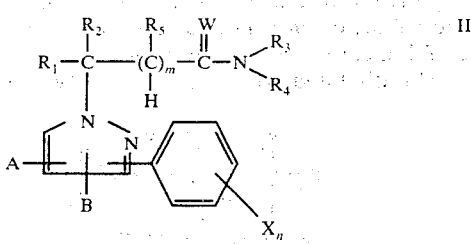

II

Disclosed is a composition for herbicidal use comprising an inert adjuvant and, as the active ingredient, an effective amount of a compound of the formula:

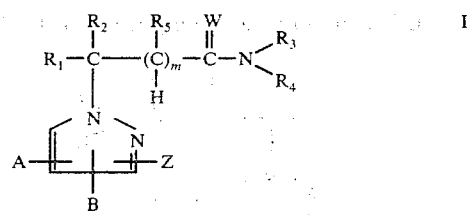

I

Further disclosed is a composition for herbicidal use comprising inert adjuvants and, as the active ingredient, an effective amount of a compound of the formula:

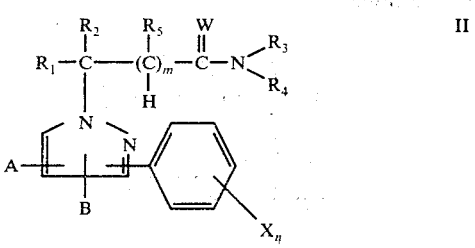

II $R_1$, $R_2$, $R_3$, $R_4$, $R_5$, A, B, X, W, Z, m, and n are as defined previously.

The term alkyl of 1 to 6 carbon atoms, 1 to 7 carbon atoms, or 1 to 8 carbon atoms, inclusive, denotes a straight or branched chain hydrocarbon group as exemplified by methyl, ethyl, propyl, isopropyl, butyl, isobutyl, tertiary butyl, pentyl, isopentyl, 3-methylbutyl, hexyl, isohexyl, 2-methylpentyl, 3-methylpentyl, heptyl, octyl, and the like.

Haloalkyl includes the term alkyl as defined above, for example chloromethyl, dichloromethyl, trifluoromethyl, 2-chloropropyl, 3-chloropropyl, 4-chlorobutyl, 3-chlorobutyl, 5-chloropentyl, 3-chloropentyl, 6-chlorohexyl, 4-chlorohexyl, 2-chlorohexyl, and the like.

Cycloalkyl of 3 to 6 carbon atoms is exemplified by cyclopropyl, cyclobutyl, cyclopentyl and cyclohexyl.

Halogen is exemplified by fluorine, chloride, bromine, and iodine.

Alkoxy is exemplified by methoxy, ethoxy, propoxy, and isopropoxy.

Alkylthio of 1 to 3 carbon atoms is exemplified by methylthio, ethylthio, propylthio, and isopropylthio.

Carboalkoxy in which the alkyl group is from 1 to 3 carbon atoms is exemplified by carbomethoxy, carboethoxy, carbopropoxy and the like.

Acid addition salts are formed when the amides of the present invention are reacted with strong acids. Strong acids are exemplified by mineral acids such as hydrochloric, sulfuric and phosphoric. Other strong acids are aryl and alkyl sulfonic acids such as p-toluenesulfonic acid.

The compounds of formulas I thru VI are prepared according to processes illustrated by the following reaction schemes:

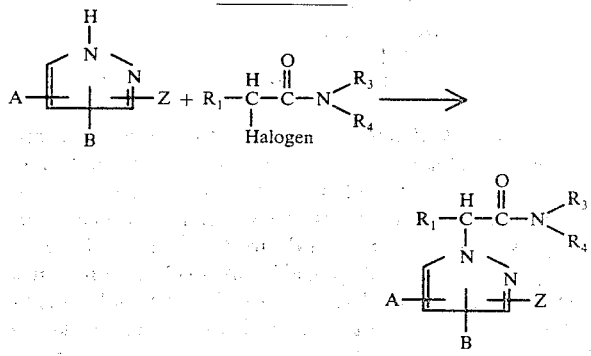

Process A wherein $R_1$, $R_3$, $R_4$, A, B, and Z are as previously defined, and Halogen is chlorine or bromine. The process is carried out by reacting a 2-haloalkanoamide with an appropriately substituted pyrazole in the presence of a base such as sodium hydride, sodium methoxide, sodium ethoxide, sodium carbonate, potassium carbonate, or the like. The reaction can be carried out in absence of added solvent or in a solvent, such as benzene, ether, tetrahydrofuran, methanol ethanol, acetone, dimethylformamide, or the like. When potassium carbonate or anhydrous sodium methoxide is used no solvent is necessary. The reaction is carried out at temperatures of 0° to 200° C. The reaction product is isolated by conventional techniques, such as chromatography, crystallization, etc. When this procedure is used a mixture of isomers is formed at positions 3 and 5, and these isomers are easily separated. This process is illustrated in examples 1–48 and 138–143.

Process B

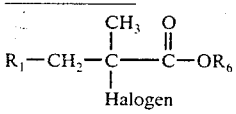

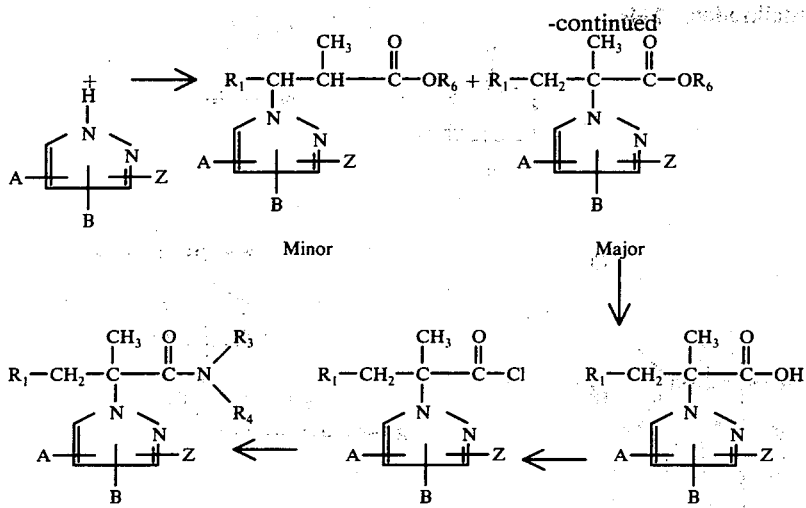
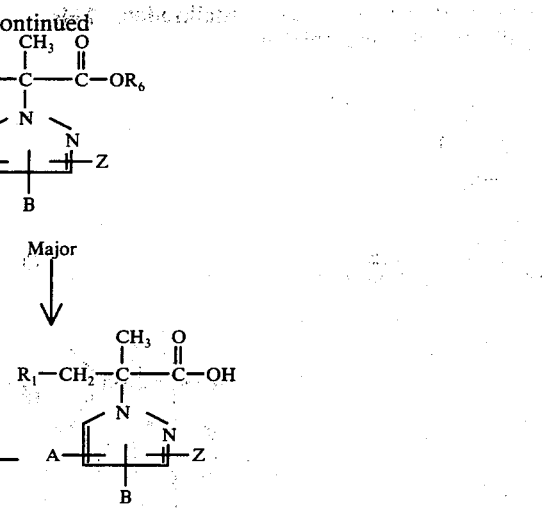

wherein A, B, Z, R₁, R₃, and R₄ are defined as above, halogen is chlorine or bromine, and R₆ is an alkyl group of 1 to 6 carbon atoms. The first step involves the reaction of a 2-haloalkanoic acid ester with the pyrazole to give a major and minor product. The major product is easily purified if desired by conventional techniques such as chromatography. The reaction is carried out using a base at temperatures of 30° to 150° C. The base can be sodium hydride, sodium methoxide or ethoxide and the like. The reaction can be carried out in absence of added solvent or in a solvent such as benzene, tetrahydrofuran, dimethylformamide and the like. To obtain the amide, the major product can be treated in conventional ways. The ester is hydrolyzed to the acid which is converted to the acid chloride with thionyl chloride and the like. Treating the acid chloride with an amine affords the product. When the crude ester mixture is treated in the above manner, both major and minor ester products are converted into the corresponding amides. This process is illustrated by examples 49–67 and 144–145.

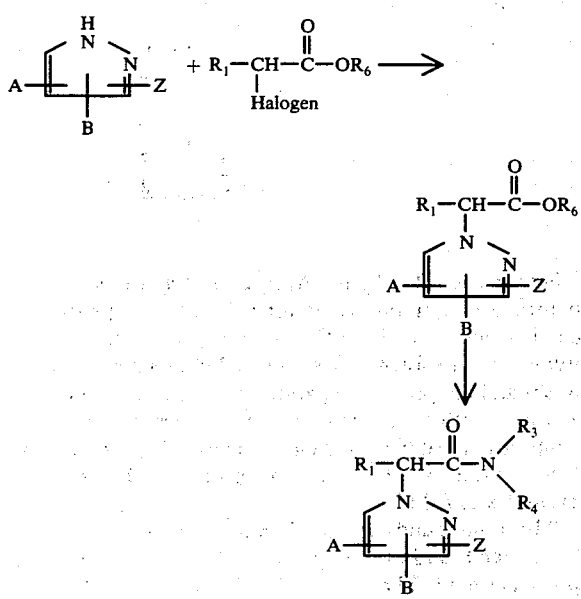

wherein A, B, Z, R₁, R₃, R₄, and R₆ are as described previously, and Halogen is chlorine or bromine. The reaction is carried out by reacting the pyrazole with an α-halo carboxylic acid ester in the presence of a base such as sodium hydride, sodium alkoxide, potassium carbonate and the like, to give a pyrazole-1-acetic acid ester. The reaction can be carried out in absence of added solvent or in a solvent such as ether, tetrahydrofuran, benzene, alcohol and the like. The ester is then hydrolyzed to the corresponding pyrazole-1-acetic acid. The acid is converted to the amide via an acid chloride using conventional techniques. The product is separated by crystallization, chromatography or other suitable means known in the art. This process is illustrated in examples 68–93.

In a related procedure, the ester products initially formed in Processes B and C may be directly converted to the amide by reaction with the appropriate amine in a sealed reaction vessel at temperatures of 30° to 200° C. The one step amidation reaction can be carried out in absence of added solvent, or in presence of a solvent, such as benzene, methanol, and the like.

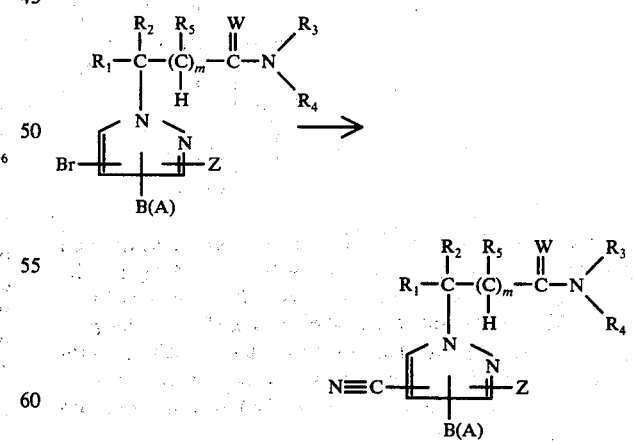

where R₁, R₂, R₃, R₄, R₅, B, and Z are as defined above. This process is used to prepare compounds of formula I, wherein A or B is cyano. The process is carried out by reacting the pyrazole in a solvent, such as dimethylformamide, with cuprous cyanide under reflux conditions for 2–24 hours. The product is separated using conventional methods, such as crystallization. This process is illustrated in example 94.

Process E

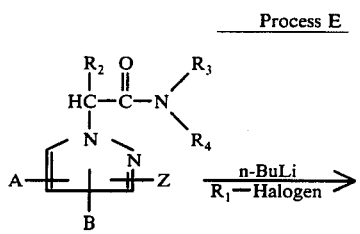

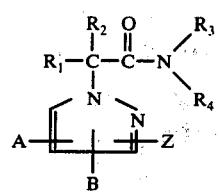

wherein A, B, Z, R₁, R₂, R₃, and R₄ are defined as above, and Halogen is preferably iodine or bromine. This process enables the addition of various alkyl groups to the parent pyrazole. The reaction is carried out by adding a solution of n-butyl lithium in hexane to the pyrazole in an inert atmosphere, such as nitrogen, in a solvent such as ether or tetrahydrofuran. Other strong bases, such as tert-butyl lithium and lithium diisopropylamide may be used in place of n-butyl lithium. An alkyl halide is added to this and the reaction is allowed to stir for 1-2 hours. The product is separated and isolated using conventional techniques. This process is illustrated in examples 95-107.

Process F

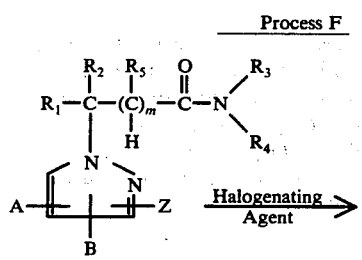

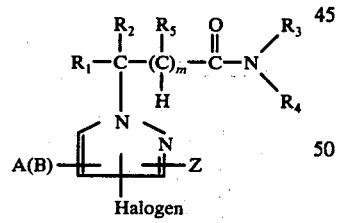

where A, B, Z, R₁, R₂, R₃, R₄, R₅, and m are as defined above provided that A or B or both are hydrogen. The halogenating agent, e.g., bromine, chlorine, tert-butyl hypochlorite, or sulfuryl chloride, is added to the pyrazole in a solvent, such as chloroform, carbon tetrachloride, acetic acid, and the product isolated using conventional techniques. This process is illustrated in examples 108-120 and 146-148

Process G

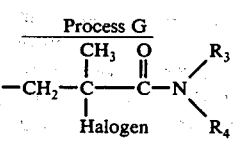

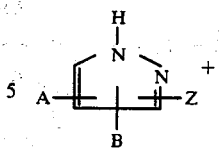

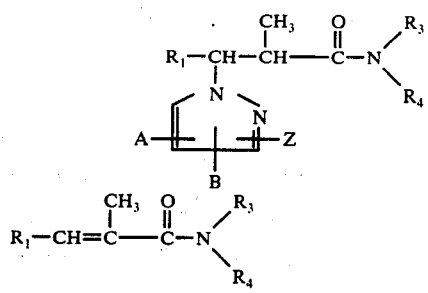

where A, B, R₁, R₃, R₄, and Z are as described previously and Halogen is chlorine or bromine. The reaction is carried out by reacting the pyrazole with an α-haloalkanoamide or an acrylamide at a temperature of 50° to 200° C. The reaction can be carried out in absence of added solvent, or in an inert solvent such as toluene, dimethylformamide and the like. When the α-haloalkanoamide is used, addition of 1 equivalent of a base such as sodium methoxide, sodium carbonate and the like is advantageous; in this reaction, the α-haloalkanoamide is first converted to the acrylamide which then reacts with the pyrazole. This process is illustrated in examples 121-126 and example 149.

Process H

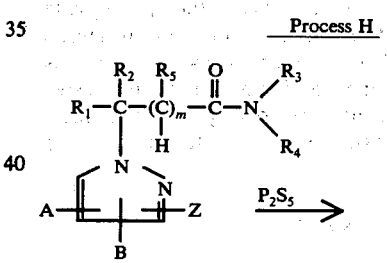

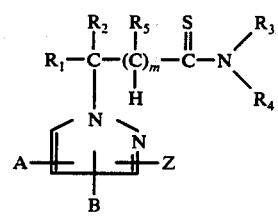

where R₁, R₂, R₃, R₄, R₅, A, B, Z, and m are defined as before for compounds of formula 1. This process is carried out by adding phosphorus pentasulfide to the pyrazole in a solvent. This is heated over a period of 1-6 hours and the product separated by extraction, crystallization or other conventional techniques. Suitable solvents are pyridine, benzene, dimethylformamide, xylene, dioxane and the like. This process is illustrated in examples 127-137.

The compounds of the formula 1 of this invention have been found to be active as herbicides both pre- and post-emergent. The compounds of the formula 1 can be used to prevent damage to field crops due to weed competition, and they can be used to prevent unsightly and deleterious growths of weeds on home lawns, golf courses, cemeteries, railroad rights-of-way, waterways, rice paddies and parks.

Compounds of the formula 1 have been found to be highly active against both broadleaf and grassy weeds. Illustratively, against various weeds, e.g., crabgrass (*Digitaria sanguinalis L.*), yellow foxtail (*Setaria glauca L.*), wild oat (*Avena fatua L.*), bindweed (*Convolvulus arvensis L.*), Johnson grass (*Sorghum halepense L.*), buckhorn plantain (*Plantago lanceolata L.*), curly dock (*Rumex crispus L.*), wild mustard (*Brassica kaber DG.*), purslane (*Portulaca oleracea L.*), barnyard-grass (*Echinochloa crusgalli L.*), yellow nutsedge (*Cyperus esculentus*), and purple nutsedge (*Cyperus rotundus*).

Illustratively, control and significant growth retardation of the foregoing weed species has been achieved using the compounds of this invention at rates of from 0.01 to 12.5 lbs. per acre. Depending upon the kinds of weeds to be controlled, the stage of weed development, the degree of infestation, and the presence or absence of aesthetic or crop plants, the compounds of this invention can be applied to soil, germinating weed seeds, weed seedlings, plant growth media, growing plants, or any other selected situs for control of weeds at rates ranging from about 1/16 to 1/8 lb. per acre up to about 50 lbs. per acre. Ordinarily, the situs will be soil, but this term is used in the broad sense — anywhere where weed growth might be a problem, e.g., gravel driveways, railroad beds, flat built-up roofs, ponds, lakes, streams, and canals. Aquatic applications effectively use about 2 to about 10,000 or more, parts per million (ppm), by weight.

The compounds of formula 1 can be applied to a situs in a dispersible pure form, but dispersible formulations for herbicidal use are preferred. The dispersible formulations of this invention comprise a compound of the formula 1 in a homogeneous, dispersible form with a homogeneous dispersible carrier. Adjuvants such as surfactants, humectants, dispersants, adhesive or sticking or spreading agents, corrosion inhibitors, and anti-foaming agents can be included.

A homogeneous dispersible carrier comprehends a particulate solid carrier or a liquid carrier diluent. The compound can be dispersed in a liquid carrier diluent as a solute or as finely divided particles (suspension).

The term "dispersible", as used in this specification and in th claims, means matter in a liquid or particulate state such that it can be evenly distributed over a given area or metered into a body of water. A "liquid" state includes true solutions as well as dispersions of particulate solids in a liquid. Emulsions of one liquid in another, e.g., oil-in-water, are also contemplated. The active compound can be in either the dispersed phase, the continuous phase, or partitioned between them both. In general, the active compound will be preponderantly in the dispersed phase when emulsions are used. A "particulate" state includes the general concept of finely divided separate particles, and granular particles as large as 10 mesh (U.S.) or even somewhat larger when appropriate herbicidal practice indicates as advantage in using larger granules.

The granular particles could be included in what is termed an "iterstitial" state, which contemplates the deposition or entrapment of the active compound within the interstices of a porous body. For example, the compounds can be mixed with an elastomer, e.g., natural rubber, chloroprene, butyl rubber, polyether and polyester urethanes and the like, which may be further processed according to conventional techniques in the elastomeric art. The latter elastomeric matrices as well as conventional granules provide a slow, sustained release of the active herbicide so that herbicidal concentrations of the active compound can be obtained over a prolonged interval for the control of weeds.

Illustrative of the adjuvants named above, humectants include glycerol, diethylene glycol, solubilized lignins (such as calcium ligninsulfonate), and the like. Dispersants include bentonite, sodium, ammonium, calcium or aluminum ligninsulfonate, condensed naphthalene sulfonate and the like. Adhesive or sticking agents include vegetable oils, naturally occurring gums, casein, and the like. A suitable corrosion inhibitor is epichlorohydrin, and suitable anti-foaming agents such as fatty acids, e.g., sodium stearate; and silicones.

Representative surfactants include alkyl sulfates and sulfonates, alkyl aryl sulfonates, sulfosuccinate esters, polyoxyethylene sulfates, polyoxyethylene-sorbitan esters, e.g., monolaurate, alkyl aryl polyether sulfates, alkyl aryl polyether alcohols, alkyl naphthalene sulfonates, alkyl quaternary ammonium salts, sulfated fatty acids and esters, sulfated fatty acid amides, glycerol mannitan laurate, polyalkylether condensates of fatty acids or alcohols, and the like.

Suitable surfactants include blends of alkyl aryl sulfonates and polyalcohol carboxylic acid esters (Emcol H-77), blends of polyoxyethylene ethers and oil-soluble sulfonates (Emcol H-400), blends of alkyl aryl sulfonates and alkylphenoxy polyethoxy ethanols (Tritons X-151, X-161, and X-171), e.g., about equal parts of sodium aryl or alkylbenzene sulfonate and isooctylphenoxy polyethoxy ethanol containing about 12 ethoxy groups, and blends of calcium alkyl aryl sulfonates and polyethoxylated vegetable oils (Agrimul $N_4S$). It will be understood, of course, that the sulfate and sulfonate surfactants suggested above will preferably be used in the form of their soluble salts, for example, their sodium salts. All of these surfactants are capable of reducing the surface tension of water to less than about 40 dynes per centimeter in concentrations of about 1% or less. The dispersible powder formulations can be prepared with a mixture of surfactants of the types indicated if desired.

The concentration of the active compound of the Formula 1 according to this invention, in the new herbicidal formulations of this invention is not usually a critical, limiting factor in achieving a desired herbicidal effect. The most important factor is how much compound is applied to an area of weeds to be controlled. It is readily apparent that one can apply a large amount of a formulation having a low concentration of active compound or a relatively small amount of a formulation having a high concentration. Whether a low or high concentration should be used depends upon the mode of application, the amount and kinds of vegetation, and the thoroughness of coverage desired. The total amount to be applied depends upon the kinds of weeds and crop, if any, the severity of infestation, the stage of plant development, and the season of the year.

Representative homogeneous dispersible formulations according to this invention include sprays, dusts, and granular formulations. Spray formulations are preferred for foliar applications and for uniformly controlled applications to a soil. Granular formulations are usually applied in bands spanning the seeded row, although broadcast distribution is advantageous when soil incorporation is practiced and a prolonged effect is desired.

The spray formulations in accordance with the invention can be aqueous solutions, aqueous suspensions, water-in-oil emulsions, oil-in-water emulsions, and oil solutions. The spray formulations will conveniently comprise from about 0.1% or lower to about 50% by weight or even higher, a volume of spray being applied so that a herbicidally effective amount of compound of Formula I is distributed over the treated area. Sprays containing about 0.25 ounce to about 16 lbs. of compound of Formula I in a 20 gal. to 40 gal. volume are applied to foliage or soil for effective herbicidal action.

Concentrates for preparing spray formulations are advantageously prepared by dissolving the active compounds of the invention in a solvent, or by dispersing the active compounds in a dispersible solid or liquid carrier diluent. Illustratively, the herbicidally active compound of Formula I of this invention is dissolved or dispersed in water or a suitable water-miscible or water-immiscible inert organic liquid. Representative water-miscible organic liquids include acetone, methyl ethyl ketone, dimethylformamide, alcohols, monoalkyl ethers of ethylene glycol, ethyl acetate, and the like. Representative substantially water-immiscible organic liquids (i.e., a solvent carrier which is soluble in water to the extent of less that 2.5% by volume at temperatures of the order of 20° to 30° C.) for preparing emulsifiable concentrates include petroleum oils, distillates, toluene, xylene, cumene, and like aromatic hydrocarbons, isoparaffin oil, mineral oil, and the like.

Advantageously, the concentration of active ingredient in the emulsifiable concentrates (with or without surfactant) can range from about 5% to about 90% by weight, preferably from about 10% to about 40%. A concentrate comprising 20% (by weight) of the compound dissolved in a water-immiscible solvent of the kind noted above can be admixed with an aqueous medium in the proportions of 13 ml. of concentrate with 1 gal. of medium to give a mixture containing 700 parts of active ingredient per million parts of liquid carrier. Similarly, 1 qt. of a 20% concentrate mixed with 40 gals. of water provides about 1200 ppm (parts per million) of active ingredient. In the same manner, more concentrated solutions of active ingredient can be prepared.

Dust formulations in accordance with the invention are readily prepared by dispersing the active compound in a dispersible solid by grinding a mixture of the compound and a pulverulent solid carrier in the presence of each other. Grinding is conveniently accomplished in a ball mill, a hammermill, or by air-blast micronization. These dust compositions can also be prepared by dissolving the compound of Formula I in a volatile solvent such as methylene chloride, mixing the solution with a pulverulent solid carrier, evaporating the solvent, and pulverizing the impregnated carrier. A suitable ultimate particle size is less than 60 microns. Perferably, 95% of the particles are less than 50 microns, and about 75% are 5 to 20 microns. Dusts of this degree of comminution are conveniently free-flowing.

Representative suitable pulverulent solid carriers include the natural clays such as China, Georgia, Barden, Attapulgus, kaolin, and Montmorillonite clays; minerals in their natural forms as they are obtained from the earth such as talc, pyrophyllite, quartz, diatomaceous earth, fuller's earth, chalk, rock phosphates and sulfates, calcium carbonates, sulfur, silica and sillicates; chemically modified minerals such as washed bentonite, precipitated calcium phosphate, precipitated calcium carbonate, precipitated calcium silicate, synthetic magnesium silicate, and colloidal silica; and organic flours such as wood, walnut shell, soybean, cottonseed, and tobacco flours, and free-flowing, hydrophobic starches.

The proportions of pulverulent carrier and compound of Formula I can vary over a wide range depending upon the plants to be controlled, rates of application according to equipment available, and the conditions of treatment. In general, dust formulations contain up to about 90% (on a weight basis) of the active ingredient. Dusts having as little as 0.001% of the active ingredient can be used, but a generally preferred proportion is from about 0.50% to about 20% of active ingredient.

Advantageously, a dust formulation as described above includes a surfactant, because about 0.1% to about 12% of a surfactant promotes dispersibility of a dust in water and facilitates formulation of aqueous sprays or dispersibility of a dust formulation applied directly to water surfaces or aquatic weeds. Dust formulations comprising a surfactant are known as dispersible or wettable powders. As indicated, dispersible or wettable powders can be admixed with water to obtain any desired concentration up to about 50% w/v of active ingredient. The dispersible or wettable powders conveniently comprise from about 10% to about 90% active ingredient, preferably about 30% to about 80%.

A suitable dispersible powder formulation is obtained by blending and milling 327 lbs. of Georgia Clay, 4.5 lbs. of calcium alkyl aryl benzene sulfonate (NeKal BA77) as a wetting agent, 9 lbs. of a polymerized sodium salt of substituted benzoid long-chain sulfonic acid (Daxad 27) as a dispersing agent, and 113 lbs. of the active ingredient. The resulting formulation has the following percentage composition (parts herein are by weight unless otherwise specified):

| | |
|---|---|
| Active ingredient | 25% |
| Calcium alkyl aryl benzene sulfonate | 1% |
| Polymerized sodium salt of substituted benzoid long-chain sulfonic acid | 2% |
| Georgia Clay | 72% |

This formulation, when dispersed in water at the rate of 10 lbs. per 100 gals., gives a spray formulation containing about 0.3% (3000 ppm) active ingredient which can be applied to weeds at the rate of 40 gals. per acre to give a total application of active ingredient of 1 lb. per acre.

Further in accordance with this invention, formulations of the compounds of the Formula I with oil are particularly efficacious, and herbicidal action of the compound is improved. Any petroleum oil can be used so long as it is not so viscous as to be too difficult to disperse. A non-phytotoxic oil is satisfactory.

Advantageously, a 50% wettable powder of the herbicidally active ingredient is mixed with about 38 gals. water and 2 gals. oil for spray application.

The following examples are illustrative of the process and products of the present invention but are not to be construed as limiting.

EXAMPLE 1

N,N,α,4-Tetramethyl-3-phenylpyrazole-1-acetamide and
N,N,α,4-tetramethyl-5-phenylpyrazole-1-acetamide To a solution of the sodium salt of 4-methyl-3-phenylpyrazole, prepared by addition of sodium hydride (3.0 g., 57% in oil, 0.071 mole) to 4-methyl-3-phenylpyrazole (10.5 g., 0.066 mole) in THF (100 ml.), was added 10.0 g. (0.075 mole) of N,N-dimethyl-2-chloropropionamide. After 18 hours, the solution was evaporated and the residue was partitioned between chloroform and water. The residue obtained on evaporation of the chloroform phase was chromatographed on silica gel using benzene:ethyl acetate as eluant to give, as the first product eluted from the column, N,N,α,4-tetramethyl-3-phenylpyrazole-1-acetamide (17.7 g.). Two recrystallizations from cyclohexane gave the analytical sample as fine needles, m.p. 74.5°–76.5° C.: nmr (CDCl$_3$) δ 1.63 (d, 3, CH$_3$—CH), 2.20 (s, 3, ArCH$_3$), 2.92 (s, 3, N—CH$_3$), 3.02 (s, 3, N—CH$_3$), 5.43 (q, 1, CH$_3$CH), 7.30–7.50 (m, 4, ArH) and 7.56–7.80 (m, 2, ArH).

Analysis: Calc'd. for C$_{15}$H$_{19}$N$_3$O: C, 70.00; H, 7.44; N, 16.33. Found: C, 70.08; H, 7.46; N, 16.62.

Continued elution of the column gave N,N,α,4-tetramethyl-5-phenylpyrazole-1-acetamide (2.4 g.). Recrystallization from benzene:Skellysolve B followed by ethyl acetate gave the analytical sample, m.p. 88°–90° C.: nmr (CDCl$_3$) δ 1.67 (d, 3, CH$_3$CH), 1.97 (s, 3, ArCH$_3$), 2.57 (s, 3, N—CH$_3$), 2.83 (s, 3, N—CH$_3$), 5.02 (q, 1, CH$_3$CH) and 7.15–7.55 (m, 6, ArH).

Analysis: Calc'd. for C$_{15}$H$_{19}$N$_3$O: C, 70.00; H, 7.44; N, 16.33. Found: C, 70.13; H, 7.51; N, 16.49.

Alternative Synthesis for
N,N,α,4-tetramethyl-3-phenylpyrazole-1-acetamide

A mixture of 4-methyl-3-phenylpyrazole (3.65 g., 0.023 mole) N,N-dimethyl-2-chloropropionamide (3.78 g., 0.027 mole) and anhydrous potassium carbonate (4.4 g., 0.032 mole) was heated with stirring at 130° C. for 6 hours. The reaction mixture was cooled and crystallized from 50% aqueous methanol to give 4.5 g. of N,N,α,4-tetramethyl-3-phenylpyrazole-1-acetamide as large rods, m.p. 87°–89° C.

EXAMPLE 2

N,N,α-Trimethyl-3-phenylpyrazole-1-acetamide and N,N,α-trimethyl-5-phenylpyrazole-1-acetamide Using the procedure of Example 1, but substituting 3-phenylpyrazole for 4-methyl-3-phenylpyrazole there was obtained
N,N,α-trimethyl-3-phenylpyrazole-1-acetamide with a melting point of 79.5°–80° C.

Analysis: Calc'd. for C$_{14}$H$_{17}$N$_3$O: C, 69.11; H, 7.04; N, 17.27. Found: C, 69.42; H, 7.03; N, 17.52.
and N,N,α-trimethyl-5-phenylpyrazole-1-acetamide as an oil.

Analysis: Calc'd. for C$_{14}$H$_{17}$N$_3$O: C, 69.11; H, 7.04; N, 17.27. Found: C, 67.86; H, 7.18; N, 16.62.

EXAMPLE 3

N,N,α,5-Tetramethyl-3-phenylpyrazole-1-acetamide and
N,N,α,3-tetramethyl-5-phenylpyrazole-1-acetamide Using the procedure of Example 1, but substituting 3-methyl-5-phenylpyrazole for 4-methyl-3-phenylpyrazole there were obtained N,N,α,5-tetramethyl-3-phenylpyrazole-1-acetamide with a melting point of 98°–99° C.

Analysis: Calc'd. for C$_{15}$H$_{19}$N$_3$O: C, 70.00; H, 7.44; N, 16.33. Found: C, 70.03; H, 7.51; N, 16.53.
and N,N,α,3-tetramethyl-5-phenylpyrazole-1-acetamide with a melting point of 91°–93° C.

Analysis: Calc'd. for C$_{15}$H$_{19}$N$_3$O: C, 70.00; H, 7.44; N, 16.33. Found: C, 70.05; H, 7.38; N, 16.39.

EXAMPLE 4

4-Bromo-N,N,α-trimethyl-3-phenylpyrazole-1-acetamide and
4-bromo-N,N,α-trimethyl-5-phenylpyrazole-1-acetamide Using the procedure of Example 1, but substituting 4-bromo-3-phenylpyrazole for 4-methyl-3-phenylpyrazole there were obtained 4-bromo-N,N,α-trimethyl-3-phenylpyrazole-1-acetamide with a melting point of 90.5°–91.5° C.

Analysis: Calc'd. for C$_{14}$H$_{16}$BrN$_3$O: C, 52.18; H, 5.04; N, 13.04; Br, 24.80. Found: C, 51.82; H, 4.90; N, 13.12; Br, 24.73.
and 4-bromo-N,N,α-trimethyl-5-phenylpyrazole-1-acetamide having a melting point of 117.5°–119° C.

Analysis: Calc'd. for C$_{14}$H$_{16}$BrN$_3$O: C, 52.18; H, 5.04; N, 13.04; Br, 24.80. Found: C, 52.42; H, 4.98; N, 13.10; Br, 24.61.

EXAMPLE 5

4-Chloro-N,N,α-trimethyl-3-phenylpyrazole-1-acetamide and
4-chloro-N,N,α-trimethyl-5-phenylpyrazole-1-acetamide Using the procedure of Example 1, but substituting 4-chloro-3-phenylpyrazole for 4-methyl-3-phenylpyrazole there were obtained 4-chloro-N,N,α-trimethyl-3-phenylpyrazole-1-acetamide with a melting point of 73.5°–75° C.

Analysis: Calc'd. for C$_{14}$H$_{16}$ClN$_3$O: C, 60.54; H, 5.81; N, 15.13; Cl, 12.77. Found: C, 60.62; H, 5.83; N, 15.09; Cl, 12.72.
and 4-chloro-N,N,α-trimethyl-5-phenylpyrazole-1-acetamide with a melting point of 100.5°–102° C.

Analysis: Calc'd. for C$_{14}$H$_{16}$ClN$_3$O: C, 60.54; H, 5.81; N, 15.13; Cl, 12.77. Found: C, 60.80; H, 5.95; N, 15.49; Cl, 12.91.

EXAMPLE 6

4,5-Dibromo-N,N,α-trimethyl-3-phenylpyrazole-1-acetamide and
3,4-dibromo-N,N,α-trimethyl-5-phenylpyrazole-1-acetamide Using the procedure of Example 1, but substituting 3,4-dibromo-5-phenylpyrazole for 4-methyl-3-phenylpyrazole there were obtained 4,5-dibromo-N,N,α-trimethyl-3-phenylpyrazole-1-acetamide having a melting point of 132°–134° C.

Analysis: Calc'd. for C$_{14}$H$_{15}$Br$_2$N$_3$O: C, 41.92; H, 3,77; N, 10.47; Br, 39.85. Found: C, 42.24; H, 3,82; N, 10.66; Br, 39.63.
and 3,4-dibromo-N,N,α-trimethyl-5-phenylpyrazole-1-acetamide having a melting point of 115°–118° C.

Analysis: Calc'd. for C$_{14}$H$_{15}$Br$_2$N$_3$O: C, 41.92; H, 3.77; N, 10.47; Br, 39.85. Found: C, 41.92; H, 3.83; N, 10.76; Br, 39.58.

EXAMPLE 7

N,N,α-Trimethyl-3,4-diphenylpyrazole-1-acetamide and N,N,α-trimethyl-4,5-diphenylpyrazole-1-acetamide Using the procedure of Example 1, but substituting 3,4-diphenylpyrazole for 4-methyl-3-phenylpyrazole there were obtained N,N,α-trimethyl-3,4-diphenylpyrazole-1-acetamide having a melting point of 122°–124° C.

Analysis: Calc'd. for $C_{20}H_{21}N_3O$: C, 75.21; H, 6.63; N, 13.16. Found: C, 75.13; H, 6.49; N, 13.54.
and N,N,α-trimethyl-4,5-diphenylpyrazole-1-acetamide having a melting point of 151°–153° C.

Analysis: Calc'd. for $C_{20}H_{21}N_3O$: C, 75.21; H, 6.63; N, 13.16. Found: C, 75.30; H, 6.62; N, 13.46.

EXAMPLE 8

4-Ethyl-N,N,α-trimethyl-3-phenylpyrazole-1-acetamide

Using the procedure of Example 1, but substituting 4-ethyl-3-phenylpyrazole for 4-methyl-3-phenylpyrazole there was obtained 4-ethyl-N,N,α-trimethyl-3-phenylpyrazole-1-acetamide having a melting point of 73.5°–75° C.

Analysis: Calc'd. for $C_{16}H_{21}N_3O$: C, 70.82; H, 7.80; N, 15.49. Found: C, 70.88; H, 7.75; N, 15.75.

EXAMPLE 9

4,5,6,7-Tetrahydro-N,N,α-trimethyl-3-phenyl-1H-indazole-1-acetamide

Using the procedure of Example 1, but substituting 3-phenyl-4,5,6,7-tetrahydroindazole for 4-methyl-3-phenylpyrazole there was obtained 4,5,6,7-tetrahydro-N,N,α-trimethyl-3-phenyl-1H-indazole-1-acetamide having a melting point of 101°–103° C.

Analysis: Calc'd. for $C_{18}H_{23}N_3O$: C, 72.69; H, 7.80; N, 14.13. Found: C, 72.77; H, 7.73; N, 14.24.

EXAMPLE 10

N,N,α-Trimethyl-3,5-diphenylpyrazole-1-acetamide

Using the procedure of Example 1, but substituting 3,5-diphenylpyrazole for 4-methyl-3-phenylpyrazole, there was obtained N,N,α-trimethyl-3,5-diphenylpyrazole-1-acetamide having a melting point of 133°–135° C.

Analysis: Calc'd. for $C_{20}H_{21}N_3O$: C, 75.21; H, 6.63; N, 13.16. Found: C, 75.31; H, 6.71; N, 13.51.

EXAMPLE 11

N,N,α,3,5-Pentamethyl-4-phenylpyrazole-1-acetamide

Using the procedure of Example 1, but substituting 3,5-dimethyl-4-phenylpyrazole for 4-methyl-3-phenylpyrazole there was obtained N,N,α,3,5-pentamethyl-4-phenylpyrazole-1-acetamide having a melting point of 122°–123.5° C.

Analysis: Calc'd. for $C_{16}H_{21}N_3O$: C, 70.82; H, 7.80; N, 15.49. Found: C, 70.83; H, 7.71; N, 15.79.

EXAMPLE 12

N,N,α,4,5-Pentamethyl-3-phenylpyrazole-1-acetamide

Using the procedure of Example 1, but substituting 3,4-dimethyl-5-phenylpyrazole for 4-methyl-3-phenylpryazole there was obtained N,N,α,4,5-pentamethyl-3-phenylpyrazole-1-acetamide having a melting point of 76°–79° C.

Analysis: Calc'd. for $C_{16}H_{21}N_3O$: C, 70.82; H, 7.80; N, 15.49. Found: C, 70.64; H, 7.75; N, 15.55.

EXAMPLE 13

N,N,α-Trimethyl-3-(o-tolyl)pyrazole-1-acetamide and N,N,α-trimethyl-5-(o-tolyl)pyrazole-1-acetamide Using the procedure of Example 1, but substituting 3-(o-tolyl)pyrazole for 4-methyl-3-phenylpyrazole there was obtained N,N,α-trimethyl-3-(o-tolyl)-pyrazole-1-acetamide having a boiling point of 164°–174°/0.3 mm.

Analysis: Calc'd. for $C_{15}H_{19}N_3O$: C, 70.00; H, 7.44; N, 16.33. Found: C, 69.90; H, 7.50; N, 16.22.
and N,N,α-trimethyl-5-(o-tolyl)pyrazole-1-acetamide having a melting point of 84.5°–86.5° C.

Analysis: Calc'd. for $C_{15}H_{19}N_3O$: C, 70.00; H, 7.44; N, 16.33. Found: C, 69.94; H, 7.32; N, 16.23.

EXAMPLE 14

N,N,α,4-Tetramethyl-3-(o-methoxyphenyl)pyrazole-1-acetamide and
N,N,α,4-tetramethyl-5-(o-methoxyphenyl)pyrazole-1-acetamide Using the procedure of Example 1, but substituting 4-methyl 3-(o-methoxyphenyl)pyrazole for 4-methyl-3-phenylpyrazole there was obtained N,N,α,4-tetramethyl-3-(o-methoxyphenyl)pyrazole-1-acetamide having a boiling point of 180°/0.5 mm.

Analysis: Calc'd. for $C_{16}H_{21}N_3O_2$: C, 66.87; H, 7.37; N, 14.62. Found: C, 66.13; H, 7.42; N, 14.50.
and N,N,α,4-tetramethyl-5-(o-methoxyphenyl)-pyrazole-1-acetamide having a melting point of 118°–120° C.

Analysis: Calc'd. for $C_{16}H_{21}N_3O_2$: C, 66.87; H, 7.37; N, 14.62. Found: C, 66.62; H, 7.27; N, 14.63.

EXAMPLE 15

3-(o-Chlorophenyl)-N,N,α-trimethylpyrazole-1-acetamide and
5-(o-chlorophenyl)-N,N,α-trimethylpyrazole-1-acetamide Using the procedure of Example 1, but substituting 3-(o-chlorophenyl)pyrazole for 4-methyl-3-phenylpyrazole there was obtained 3-(o-chlorophenyl)-N,N,α-trimethylpyrazole-1-acetamide having a boiling point of 176°–178°/.1 mm.

Analysis: Calc'd. for $C_{14}H_{16}ClN_3O$: C, 60.54; H, 5.81; N, 15.13; Cl, 12.77. Found: C, 60.17; H, 5.82; N, 14.96; Cl, 12.58.
and 5-(o-chlorophenyl)-N,N,α-trimethylpyrazole-1-acetamide having a melting point of 83°–86° C.

Analysis: Calc'd. for $C_{14}H_{16}ClN_3O$: C, 60.54; H, 5.81; N, 15.13; Cl, 12.77. Found: C, 60.89; H, 5.82; N, 15.06; Cl, 12.38.

EXAMPLE 16

3-(p-Chlorophenyl)-N,N,α-trimethylpyrazole-1-acetamide and
5-(p-chlorophenyl)-N,N,α-trimethylpyrazole-1-acetamide Using the procedure of Example 1, but substituting 3-(p-chlorophenyl)pyrazole for 4-methyl-3-phenylpyrazole there were obtained 3-(p-chlorophenyl)-N,N,α-trimethylpyrazole-1-acetamide having a melting point of 95°–99° C.

Analysis: Calc'd. for $C_{14}H_{16}ClN_3O$: C, 60.54; H, 5.81; N, 15.13; Cl, 12.77. Found: C, 60.57; H, 5.84; N, 15.20; Cl, 12.83.

and 5-(p-chlorophenyl)-N,N,α-trimethylpyrazole-1-acetamide having a melting point of 96°–97° C.

Analysis: Calc'd. for $C_{14}H_{16}ClN_3O$: C, 60.54; H, 5.81; N, 15.13; Cl, 12.77. Found: C, 60.62; H, 5.74; N, 15.07; Cl, 2.96.

EXAMPLE 17

3-(p-Chlorophenyl)-N,N,α,4-tetramethylpyrazole-1-acetamide

Following the procedure of Example 1, but substituting 3-(p-chlorophenyl)-4-methylpyrazole for 4-methyl-3-phenylpyrazole there was obtaned 3-(p-chlorophenyl)-N,N,α,4-tetramethylpyrazole-1-acetamide having a melting point of 99.5°–101° C.

Analysis:
Calc'd. for $C_{15}H_{18}ClN_3O$: C, 61.74; H, 6.22; N, 14.41; Cl, 12.15. Found: C, 61.55; H, 6.04; N, 14.41; Cl, 12.19.

EXAMPLE 18

3-(o-Methoxyphenyl)-N,N,α-trimethylpyrazole-1-acetamide

Following the procedure of Example 1, but substituting 3-(o-methoxyphenyl)pyrazole for 4-methyl-3-phenylpyrazole there was obtained 3-(o-methoxyphenyl)-N,N,α-trimethylpyrazole-1-acetamide having a melting point of 92°–94° C.

Analysis: Calc'd. for $C_{15}H_{19}N_3O_2$: C, 65.91; H, 7.01; N, 15.37. Found: C, 65.63; H, 6.96; N, 15.33.

EXAMPLE 19

3-(o-Chlorophenyl)-N,N,α,4-tetramethylpyrazole-1-acetamide

Following the procedure of Example 1, but substituting 3-(o-chlorophenyl)-4-methylpyrazole for 4-methyl-3-phenylpyrazole there was obtained 3-(o-chlorophenyl)-N,N,α,4-tetramethylpyrazole-1-acetamide having a melting point of 98.5°–100.5° C.

Analysis: Calc'd. for $C_{15}H_{18}ClN_3O$: C, 61.74; H, 6.22; N, 14.40; Cl, 12.15. Found: C, 61.98; H, 6.35; N, 14.39; Cl, 12.22

EXAMPLE 20

3-(m-Chlorophenyl)-N,N,α,4-tetramethylpyrazole-1-acetamide

Following the procedure of Example 1, but subsituting 3-(m-chlorophenyl)-4-methylpyrazole for 4-methyl-3-phenylpyrazole there was obtained 3-(m-chlorophenyl)-N,N,α,4-tetramethylpyrazole-1-acetamide having a melting point of 73°–75° C.

Analysis: Calc'd. for $C_{15}H_{18}ClN_3O$: C, 61.74; H, 6.22; N, 14.40; Cl, 12.15. Found: C, 61.90; H, 6.20; N, 14.30; Cl, 12.21.

EXAMPLE 21

3-(m-Chlorophenyl)-N,N,α-trimethylpyrazole-1-acetamide

Following the procedure of Example 1, but substituting 3-(m-chlorophenyl)pyrazole for 4-methyl-3-phenylpyrazole there was obtained 3-(m-chlorophenyl)-N,N,α-trimethylpyrazole-1-acetamide having a boiling point of 175° /0.08 mm.

Analysis: Calc'd. for $C_{14}H_{16}ClN_3O$: C, 60.54; H, 5.81; N, 15.13; Cl, 12.77. Found: C, 60.24; H, 5.92; N, 15.39; Cl, 13.12.

EXAMPLE 22

3-(2,5-Dichlorophenyl)-N,N,α-trimethylpyrazole-1-acetamide

Following the procedure of Example 1, but substituting 3-(2,5-dichlorophenyl)pyrazole for 4-methyl-3-phenylpyrazole there was obtained 3-(2,5-dichlorophenyl)-N,N,α-trimethylpyrazole-1-acetamide having a melting point of 73.5°–76.5° C.

Analysis: Calc'd. for $C_4H_{15}Cl_2N_3O$: C, 53.86; H, 4.84; N, 13.46; Cl, 22.71. Found: C, 54.04; H, 4.92; N, 13.65; Cl, 22.73.

EXAMPLE 23

N,N,α,4-Tetramethyl-3-(o-tolyl)pyrazole-1-acetamide

Following the procedure of Example 1, but substituting 4-methyl-3-(o-tolyl)pyrazole for 4-methyl-3-phenylpyrazole there was obtained N,N,α,4-tetramethyl-3-(o-tolyl)pyrazole-1-acetamide having a boiling point of 178°–182° /0.7 mm.

EXAMPLE 24

N,N,α-Trimethyl-3-(p-tolyl)pyrazole-1-acetamide

Following the procedure of Example 1, but substituting 3-(p-tolyl)pyrazole for 4-methyl-3-phenylpyrazole there was obtained N,N,α-trimethyl-3-(p-tolyl)-pyrazole-1-acetamide having a melting point of 79°–82° C.

Analysis: Calc'd. for $C_{15}H_{19}N_3O$: C, 70.00; H, 7.44; N, 16.33. Found: C, 70.24; H, 7.29; N, 16.60.

EXAMPLE 25

N,N,α-Trimethyl-3-(m-nitrophenyl)pyrazole-1-acetamide

Following the procedure of Example 1, but substituting 3-(m-nitrophenyl)pyrazole for 4-methyl-3-phenylpyrazole there was obtained N,N,α-trimethyl-3-(m-nitrophenyl)pyrazole-1-acetamide having a melting point of 117°–119° C.

Analysis: Calc'd. for $C_{14}H_{16}N_4O_3$: C, 58.32; H, 5.59; N, 19.44. Found: C, 59.06; H, 5.68; N, 19.72.

EXAMPLE 26

N,N,α-Trimethyl-3-(2,6-dichlorophenyl)pyrazole-1-acetamide

Following the procedure of Example 1, but substituting 3-(2,6-dichlorophenyl)pyrazole for 4-methyl-3-phenylpyrazole there was obtained N,N,α-trimethyl-3-(2,6-dichlorophenyl)pyrazole-1-acetamide having a melting point of 88°–90° C.

Analysis: Calc'd. for $C_{14}H_{15}Cl_2N_3O$: C, 53.86; H, 4.84; N, 13.46; Cl, 22.71. Found: C, 53.78; H, 5.02; N, 13.41; Cl, 22.73.

EXAMPLE 27

4-Chloro-N,N-diethyl-α-methyl-3-phenylpyrazole-1-acetamide and
4-chloro-N,N-diethyl-α-methyl-5-phenylpyrazole-1-acetamide Using the procedure of Example 1, but substituting 2-chloro-N,N-diethylpropionamide for 2-chloro-N,N-dimethylpropionamide and 4-chloro-3-phenylpyrazole for 4-methyl-3-phenylpyrazole there were obtained 4-chloro-N,N-diethyl-α-methyl-3-phenylpyrazole-1-acetamide having a boiling point of 191°-192° /0.75 mm.

Analysis: Calc'd. for $C_{16}H_{20}ClN_3O$: C, 62.84; H, 6.59; N, 13.74; Cl, 11.59. Found: C, 62.50; H, 6.74; N, 13.48; Cl, 11.58.

and 4-chloro-N,N-diethyl-α-methyl-5-phenylpyrazole-1-acetamide having a melting point of 85°-87° C.

Analysis: Calc'd. for $C_{16}H_{20}ClN_3O$: C, 62.84; H, 6.59; N, 13.74; Cl, 11.59. Found: C, 62.92; H, 6.71; N, 13.62; Cl, 11.58.

EXAMPLE 28

α-Ethyl-N,N,4-trimethyl-3-phenylpyrazole-1-acetamide and
α-ethyl-N,N,4-trimethyl-5-phenylpyrazole-1-acetamide Using the procedure of Example 1, but substituting 2-chloro-N,N-dimethylbutyramide for 2-chloro-N,N-dimethylpropionamide there were obtained α-ethyl-N,N,4-trimethyl-3-phenylpyrazole-1-acetamide having a melting point of 86°-88° C.

Analysis: Calc'd. for $C_{16}H_{21}N_3O$: C, 70.82; H, 7.80; N, 15.49. Found: C, 70.91; H, 7.93; N, 15.73.

and α-ethyl-N,N,4-trimethyl-5-phenylpryazole-1-acetamide having a melting point of 88°-90° C.

Analysis: Calc'd. for $C_{16}H_{21}N_3O$: C, 70,82; H, 7.80; N, 15.49. Found: C, 70.83; H, 7.82; N, 15.56.

Alternate Synthesis for
α-ethyl-N,N,4-trimethyl-3-phenylpyrazole-1-acetamide

Sodium methoxide powder (216 g., 4.0 mole) was added over 10 minutes at a stirred solution of 4-methyl-3-phenylpyrazole (632 g., 4.0 mole) in tetrahydrofuran (1.0 liter) at 10° C. 2-Bromo-N,N-dimethylbutyramide (911 g., 4.7 mole) was added dropwise over 30 minutes while maintaining the temperature of the reaction solution below 30° C. by external cooling. The solution was stirred for an additional 30 minutes at room temperature, and the THF was then removed under reduced pressure. The residual oil was partitioned between chloroform and water. The chloroform layer was evaporated and the residual oil was recrystallized from benzene:Skellysolve B to give 772 g. of α-ethyl-N,N,4-trimethyl-3-phenylpyrazole-1-acetamide, m.p. 85.5°-87.5° C.

Evaporation of the crystallization mother liquors gave 365 g. of oil containing additional product.

EXAMPLE 29

N,N,α-Trimethyl-3-(2-thienyl)pyrazole-1-acetamide and N,N,α-trimethyl-5-(2-thienyl)pyrazole-1-acetamide Following the procedure of Example 1, but substituting 3-(2-thienyl)pyrazole for 4-methyl-3-phenylpyrazole there were obtained N,N,α-trimethyl-3-(2-thienyl)pyrazole-1-acetamide having a melting point of 95°-97° C.

Analysis:

Calc'd. for $C_{12}H_{15}N_3OS$: C, 57.80; H, 6.06; N, 16.85; S, 12.85. Found: C, 57.52; H, 5.98; N, 16.76; S, 13,17.

and N,N,α-trimethyl-5-(2-thienyl)pyrazole-1-acetamide having a melting point of 80°-82° C.

Analysis: Calc'd. for $C_{12}H_{15}N_3OS$: C, 57.80; H, 6.06; N, 16.85; S, 12.85. Found: C, 58.10; H, 5,95; N, 16.87; S, 13.05.

EXAMPLE 30

N,N,α,4-Tetramethyl-3-(2-thienyl)pyrazole-1-acetamide and
N,N,α,4-tetramethyl-5-(2-thienyl)pyrazole-1-acetamide Following the procedure of Example 1, but substituting 4-methyl-3-(2-thienyl)pyrazole for 4-methyl-3-phenylpyazole there were obtained N,N,α,4-tetramethyl-3-(2-thienyl)pyrazole-1-acetamide having a melting point of 100° -102° C.

Analysis: Calc'd. for $C_{13}H_{17}N_3OS$: C, 59.29; H, 6.51; N, 15.96; S, 12.17. Found: C, 59.09; H, 6.52; N, 15.86; S, 11.99.

and N,N,α,4-tetramethyl-5-(2-thienyl)pyrazole-1-acetamide having a melting point of 77°-80° C.

Analysis: Calc'd. for $C_{13}H_{17}N_3OS$: C, 59.29; H, 6.51; N, 15.96; S, 12.17. Found: C, 59.02; H, 6.27; N, 15.87; S, 12.29.

EXAMPLE 31

α-Ethyl-N,N,4-trimethyl-3-(2-thienyl)pyrazole-1-acetamide and
α-ethyl-N,N,4-trimethyl-5-(2-thienyl)pyrazole-1-acetamide Following the procedure of Example 1, but substituting 4-methyl-3-(2-thienyl)pyrazole for 4-methyl-3-phenylpyrazole and 2-bromo-N,N-dimethylbutyramide for 2-chloro-N,N-dimethylpropionamide there were obtained α-ethyl-N,N,4-trimethyl-3-(2-thienyl)-pyrazole-1-acetamide having a melting point of 83°-85° C.

Analysis: Calc'd. for $C_{14}H_{19}N_3OS$: C, 60.62; H, 6.90; N, 15.15; S, 11.56. Found: C, 60.61; H, 6.76; N, 15.14; S, 11.49.

and α-ethyl-N,N,4-trimethyl-5-(2-thienyl)pyrazole-1-acetamide having a boiling point of 170°/0.7 mm.

Analysis: Calc'd. for $C_{14}H_{19}N_3OS$: C, 60.62; H, 6.90; N, 15.15; S, 11.56. Found: C, 60.31; H, 6.97; N, 15.07; S, 11.23.

EXAMPLE 32

N,N,α,4-Tetramethyl-3-(5-chloro-2-thienyl)pyrazole-1-acetamide

Following the procedure of Example 1, but substituting 4-methyl-3-(5-chloro-2-thienyl)pyrazole for 4-methyl-3-phenylpyrazole there was obtained N,N,α,4-tetramethyl-3-(5-chloro-2-thienyl)pyrazole-1-acetamide having a melting point of 111.5°-114° C.

Analysis: Calc'd. for $C_{13}H_{16}ClN_3OS$: C, 52.43; H, 5.42; N, 14.11; Cl, 11.91; S, 10.77. Found: C, 52.44; H, 5.59; N, 14.19; Cl, 11.68; S, 10.85.

EXAMPLE 33

N,N,4-Trimethyl-α-propyl-3-(2-thienyl)pyrazole-1-acetamide

Following the procedure of Example 1, but substituting 4-methyl-3-(2-thienyl)pyrazole for 4-methyl-3-phenylpyrazole and 2-bromo-N,N-dimethylvaleramide for 2-chloro-N,N-dimethylpropionamide there was obtained N,N4-trimethyl-α-propyl-3-(2-thienyl)pyrazole-1-acetamide having a melting point of 85°-87.5° C.

Analysis: Calc'd. for $C_{15}H_{21}N_3OS$: C, 61.82; H, 7.26; N, 14.42; S, 11.00. Found: C, 61.70; H, 7.40; N, 14.40; S, 11.05.

EXAMPLE 34

3-(2-Furyl)-N,N,α,4-tetramethylpyrazole-1-acetamide

Following the procedure of Example 1, but substituting 3-(2-furyl)-4-methylpyrazole for 3-methyl-4-phenylpyrazole there was obtained 3-(2-furyl)-N,N,α,4-tetramethylpyrazole-1-acetamide having a melting point of 93°–95° C.

Analysis: Calc'd. for $C_{13}H_{17}N_3O_2$: C, 63.14; H, 6.93; N, 16.99. Found: C, 63.17; H, 7.13; N, 17.07.

EXAMPLE 35

α-Ethyl-3-(2-furyl)-N,N,4-trimethylpryazole-1-acetamide

Following the procedure of Example 1, but substituting 3-(2-furyl)-4-methylpryazole for 4-methyl-3-phenylpryazole and 2-bromo-N,N-dimethylbutyramide for 2-chloro-N,N-dimethylpropionamide there was obtained α-ethyl-3-(2-furyl)-N,N,4-trimethylpryazole-1-acetamide having a melting point of 115°–117° C.

Analysis: Calc'd. for $C_{14}H_{19}N_3O_2$: C, 64.34; H, 7.33; N, 16.08. Found: C, 64.46; H, 7.26; N, 15.89.

EXAMPLE 36

3-(2-Furyl)-N,N,4-trimethyl-α-propylpyrazole-1-acetamide

Following the procedure of Example 1, but substituting 3-(2-furyl)-4-methylpyrazole for 4-methyl-3-phenylpyrazole and 2-bromo-N,N-dimethylvaleramide for 2-chloro-N,N-dimethylpropionamide there was obtained 3-(2-furyl)-N,N,4-trimethyl-α-propylpyrazole-1-acetamide having a melting point of 107°–109° C.

Analysis: Calc'd. for $C_{15}H_{21}N_3O$: C, 65,43; H, 7.69; N, 15.26. Found: C, 65.61; H, 7.78; N, 15.21.

EXAMPLE 37

N,N,α,α,4-Pentamethyl-5-phenylpyrazole-1-propionamide and
N,N,α,α,4-pentamethyl-3-phenylpyrazole-1-propionamide Following the procedure of Example 1, but substituting 3-chloro-N,N,2,2-tetramethylpropionamide for 2-chloro-N,N-dimethylpropionamide there were obtained N,Nα,α,4-pentamethyl-5-phenylpyrazole-1-propionamide having a melting point of 59°–60° C.

Analysis: Calc'd. for $C_{17}H_{23}N_3O$: C, 71.54; H, 8.12; N, 14.73. Found: C, 71.61; H, 8.31; N, 14.65.
and N,N,α,α,4-pentamethyl-3-phenylpyrazole-1-propionamide having a boiling point of 175°/0.03 mm.

Analysis: Calc'd. for $C_{17}H_{23}N_3O$: C, 71.54; H, 8.12; N, 14.73. Found: C, 71.43; H, 8.45; N, 14.79.

EXAMPLE 38

N,N,α-Trimethyl-3-(o-nitrophenyl)pyrazole-1-acetamide

Following the procedure of Example 1, but substituting 3-(o-nitrophenyl)pyrazole for 4-methyl-3-phenylpyrazole there was obtained N,N,α-trimethyl-3-(o-nitrophenyl)pyrazole-1-acetamide, as a brown liquid.

EXAMPLE 39

3-(o-Chlorophenyl)-α-ethyl-N,N-dimethylpyrazole-1-acetamide

Following the procedure of Example 1, but substituting 3-(o-chlorophenyl)pyrazole for 4-methyl-3-phenylpyrazole and 2-bromo-N,N-dimethylbutyramide for 2-chloro-N,N-dimethylpropionamide there was obtained 3-(o-chlorophenyl)-α-ethyl-N,N-dimethylpyrazole-1-acetamide having a melting point of 38.5°–40° C.

Analysis: Calc'd. for $C_{15}H_{18}ClN_3O$: C, 61.74; H, 6.22; N, 14.40; Cl, 12.15. Found: C, 61.99; H, 6.22; N, 14.38; Cl, 12.31.

EXAMPLE 40

α-Ethyl-N,N-dimethyl-3-(o-tolyl)pyrazole-1-acetamide

Following the procedure of Example 1, but substituting 3-(o-tolyl)pyrazole for 4-methyl-3-phenylpyrazole and 2-bromo-N,N-dimethylbutyramide for 2-chloro-N,N-dimethylpropionamide there was obtained α-ethyl-N,N-dimethyl-3-(o-tolyl)-pyrazole-1-acetamide having a melting point of 48°–51° C.

Analysis: Calc'd. for $C_{16}H_{21}N_3O$: C, 70.82; H, 7.80; N, 15.49. Found: C, 70.66; H, 7.74; N, 15.32.

EXAMPLE 41

3-(o-Chlorophenyl)-α-ethyl-N,N,4-trimethylpyrazole-1-acetamide

Following the procedure of Example 1, but substituting 3-(o-chlorophenyl)-4-methylpyrazole for 4-methyl-3-phenylpyrazole and 2-bromo-N,N-dimethylbutyramide for 2-chloro-N,N-dimethylpropionamide there was obtained 3-(o-chlorophenyl)-α-ethyl-N,N,4-trimethylpyrazole-1-acetamide having a boiling point of 180°/0.15 mm.

Analysis: Calc'd. for $C_{16}H_{20}ClN_3O$: C, 62.84; H, 6.59; N, 13.74; Cl, 11.59. Found: C, 62.69; H, 6.81; N, 13.73; Cl, 11.52.

EXAMPLE 42

α-(3-Bromopropyl)-N,N,4-trimethyl-3-phenylpyrazole-1-acetamide

Following the procedure of Example 1, but substituting 2,5-dibromo-N,N-dimethylvaleramide for 2-chloro-N,N-dimethylpropionamide there was obtained α-(3-bromopropyl)-N,N,4-trimethyl-3-phenylpyrazole-1-acetamide as a liquid.

EXAMPLE 43

α-(4-Bromobutyl)-N,N,4-trimethyl-3-phenylpyrazole-1-acetamide

Following the procedure of Example 1, but substituting 2,6-dibromo-N,N-dimethylcaproamide for 2-chloro-N,N-dimethylpropionamide there was obtained α-(4-bromobutyl)-N,N,4-trimethyl-3-phenylpyrazole-1-acetamide as a liquid.

EXAMPLE 44

α-Ethyl-N,N,4-trimethyl-3-(o-tolyl)pyrazole-1-acetamide

Following the procedure of Example 1, but substituting 4-methyl-3-(o-tolyl)pyrazole for 4-methyl-3-phenylpyrazole and 2-bromo-N,N-dimethylbutyramide for 2-chloro-N,N-dimethylpropionamide there was obtained α-ethyl-N,N,4-trimethyl-3-(o-tolyl)pyrazole-1-acetamide having a boiling point of 155°–157°/0.05 mm.

Analysis: Calc'd. for $C_{17}H_{23}N_3O$: C, 71.55; H, 8.12; N, 14.72. Found: C, 71.18; H, 8.27; N, 14.65.

EXAMPLE 45

α-(2-Chloroethyl)-N,N,4-trimethyl-3-phenylpyrazole-1-acetamide

Following the procedure of Example 1, but substituting 2-bromo-4-chloro-N,N-dimethylbutyramide for 2-chloro-N,N-dimethylpropionamide there was obtained α-(2-chloroethyl)-N,N,4-trimethyl-3-phenylpyrazole-1-acetamide as a liquid.

EXAMPLE 46

α-Cyclohexyl-N,N,4-trimethyl-3-phenylpyrazole-1-acetamide

Following the procedure of Example 1, but substituting α-bromo-N,N-dimethyl-1-cyclohexaneacetamide for 2-chloro-N,N-dimethylpropionamide there was obtained α-cyclohexyl-N,N,4-trimethyl-3-phenylpyrazole-1-acetamide having a melting point 102.5°–104.5° C.

Analysis: Calc'd. for $C_{20}H_{27}N_3O$: C, 73.81; H, 8.36; N, 12.91. Found: C, 73.70; H, 8.44; N, 12.69.

EXAMPLE 47

α-Cyclohexyl-N,N-dimethyl-3-phenylpyrazole-1-acetamide

Following the procedure of Example 1, but substituting α-bromo-N,N-dimethyl-1-cyclohexaneacetamide for 2-chloro N,N-dimethylpropionamide and 3-phenylpyrazole for 4-methyl-3-phenylpyrazole there was obtained α-cyclohexyl-N,N-dimethyl-3-phenylpyrazole-1-acetamide having a melting point of 87.5°–90° C.

Analysis: Calc'd. for $C_{19}H_{25}N_3O$: C, 73.28; H, 8.09; N, 13.49. Found: C, 73.36; H, 8.08; N, 13.39.

EXAMPLE 48

α-Butyl-N,N,4-trimethyl-3-phenylpyrazole-1-acetamide

Following the procedure of Example 1, but substituting 2-bromo-N,N-dimethylcaproamide for 2-chloro-N,N-dimethylpropionamide there was obtained α-butyl-N,N,4-trimethyl-3-phenylpyrazole-1-acetamide having a boiling point of 189°/0.1 mm.

Analysis: Calc'd. for $C_{18}H_{25}N_3O$: C, 72.20; H, 8.42; N, 14.04. Found: C, 71.76; H, 8.30; N, 13.89.

EXAMPLE 49

N,α,α,4-Tetramethyl-3-phenylpyrazole-1-acetamide, N,α,α,4-tetramethyl-5-phenylpyrazole-1-acetamide, and N,α,4-trimethyl-3-phenylpyrazole-1-propionamide Sodium hydride (25.0 g. of 57% dispersion in oil, 0.6 mole) was added to a stirred solution of 4-methyl-3-phenylpyrazole (79.0 g., 0.5 mole) in tetrahydrofuran. Ethyl-2-bromoisobutyrate (136.0 g., 0.7 mole) was added and the solution was refluxed for 4 hours. The solvent was removed by evaporation and the residual ester mixture was hydrolyzed by refluxing with methanolic sodium hydroxide solution (40 g. sodium hydroxide in 600 ml. of 30% methanol-water). After cooling, the alkaline reaction solution was extracted with ether and the aqueous phase was acidified with concentrated hydrochloric acid. The solution was extracted with chloroform, and the chloroform layer was evaporated to give a crude acid mixture in which α,α,4-trimethyl-3-phenylpyrazole-1-acetic acid was the major isomer.

The crude acid was dissolved in benzene (1 liter), and thionyl chloride (59.5 g., 0.5 mole) was added and the solution was refluxed for 3 hours. After cooling, the solution was added slowly to a stirred solution of 40% aqueous methylamine (200 ml.) containing ice (500 g.). After 10 minutes, the benzene layer was separated, washed with water, and evaporated to afford 100 g. of mixed methylamides.

Chromatography on silica gel afforded 64 g. of N,αλ,α,4-tetramethyl-3-phenylpyrazole-1-acetamide, which was recrystallized from cyclohexane; m.p. 84°–88° C.

Analysis: Calc'd. for $C_{15}H_{19}N_3O$: C, 70.00; H, 7.44; N, 16.33. Found: C, 69.95; H, 7.61; N, 16.40.

Further elution of the column afforded 4.1 g. of N,αλ,α,4-tetramethyl-5-phenylpyrazole-1-acetamide, which was recrystallized twice from ethyl acetate for analysis; m.p. 119°–120° C.

Analysis: Calc'd. for $C_{15}H_{19}N_3O$: C, 70.00; H, 7.44; N, 16.33. Found: C, 70.25; H, 7.64; N, 16.55.

Further elution of the column afforded 6.6 g. of N,α,4-trimethyl-3-phenylpyrazole-1-propionamide, which was recrystallized twice from ethyl acetate for analysis; m.p. 123°–124° C.

Analysis: Calc'd. for $C_{15}H_{19}N_3O$: C, 70.00; H, 7.44; N, 16.33. Found: C, 70.18; H, 7.41; N, 16.52.

EXAMPLE 50

α,α,4-Trimethyl-3-phenylpyrazole-1-acetamide

Following the procedure of Example 49, but substituting aqueous ammonia for aqueous methylamine there was obtained α,α,4-trimethyl-3-phenylpyrazole-1-acetamide having a melting point of 105°–106° C.

Analysis: Calc'd. for $C_{14}H_{17}N_3O$: C, 69.11; H, 7.04; N, 17.27. Found: C, 69.01; H, 7.02; N, 17.37.

EXAMPLE 51

N-Ethyl-α,α,4-trimethyl-3-phenylpyrazole-1-acetamide and N-ethyl-α,4-dimethyl-3-phenylpyrazole-1-propionamide Following the procedure of Example 49, but substituting aqueous ethylamine for aqueous methylamine there was obtained N-ethyl-α,α,4-trimethyl-3-phenylpyrazole-1-acetamide having a boiling point of 150°/0.2 mm.

Analysis: Calc'd. for $C_{16}H_{21}N_3O$: C, 70.82; H, 7.80; N, 15.49; Found: C, 70.66; H, 7.80; N, 15.30.

and N-ethyl-α,4-dimethyl-3-phenylpyrazole-1-propionamide having a melting point of 110.5°–112.5° C.

Analysis: Calc'd. for $C_{16}H_{21}N_3O$: C, 70.82; H, 7.80; N, 15.49. Found: C, 70.33; H, 7.64; N, 15.32.

EXAMPLE 52

α,α,4-Trimethyl-3-phenyl-N-isopropylpyrazole-1acetamide and α,4-dimethyl-3-phenyl-N-isopropylpyrazole-1-propionamide Following the procedure of Example 49, but substituting isopropylamine for aqueous methylamine there were obtained α,α,4-trimethyl-3-phenyl-N-isopropylpyrazole-1-acetamide having a boiling point of 160°/0.25 mm.

Analysis: Calc'd. for $C_{17}H_{23}N_3O$: C, 71.54; H, 8.12; N, 14.73. Found: C, 71.73; H, 8.20; N, 14.74.

and α,4-dimethyl-3-phenyl-N-isopropylpyrazole-1-propionamide having a melting point of 104°–107° C.

Analysis: Calc'd. for $C_{17}H_{23}N_3O$: C, 71.54; H, 8.12; N, 14.73. Found: C, 70.69; H, 7.79; N, 14.38.

EXAMPLE 53

α,α,4-Trimethyl-3-phenyl-N-propylpyrazole-1-acetamide and
α,4-dimethyl-3-phenyl-N-propylpyrazole-1-propionamide Following the procedure of Example 49, but substituting propylamine for aqueous methylamine there were obtained α,α,4-trimethyl-3-phenyl-N-propylpyrazole-1-acetamide having a melting point of 47°–50° C.

Analysis: Calc'd. for $C_{17}H_{23}N_3O$: C, 71.54; H, 8.12; N, 14.73. Found: C, 71.62; H, 8.03; N, 14.37.

and α,4-dimethyl-3-phenyl-N-propylpyrazole-1-propionamide having a melting point of 96°–98° C.

Analysis: Calc'd. for $C_{17}H_{23}N_3O$: C, 71.54; H, 8.12; N, 14.73. Found: C, 71.51; H, 7.97; N, 14.39.

EXAMPLE 54

N-Butyl-α,α,4-trimethyl-3-phenylpyrazole-1-acetamide

Following the procedure of Example 49, but substituting butylamine for aqueous methylamine there was obtained N-butyl-α,α,4-trimethyl-3-phenylpyrazole-1-acetamide having a melting point of 53°–57° C.

Analysis: Calc'd. for $C_{18}H_{25}N_3O$: C, 72.20; H, 8.42; N, 14.04. Found: C, 72.47; H, 8.62; N, 14.26.

EXAMPLE 55

N-tert-Butyl-α,α,4-trimethyl-3-phenylpyrazole-1-acetamide

Following the procedure of Example 49, but substituting tert-butylamine for methylamine, there was obtained N-tert-butyl-α,α,4-trimethyl-3-phenylpyrazole-1-acetamide having a melting point of 71°–75° C.

Analysis: Calc'd. for $C_{18}H_{25}N_3O$: C, 72.20; H, 8.42; N, 14.04. Found: C, 71.99; H, 8.78; N, 13.82.

EXAMPLE 56

α,α,4-Trimethyl-3-phenylpyrazole-1-acetanilide

Following Example 49, but substituting aniline for aqueous methylamine there was obtained α,α,4-trimethyl-3-phenylpyrazole-1-acetanilide having a melting point of 116°–119° C.

Analysis: Calc'd. for $C_{20}H_{21}N_3O$: C, 75.21; H, 6.63; N, 13.16. Found: C, 75.04; H, 6.54; N, 13.04.

EXAMPLE 57

N,α,α,4-Tetramethyl-3-phenylpyrazole-1-acetanilide

Following the procedure of Example 49, but substituting N-methylaniline for aqueous methylamine there was obtained N,α,α,4-tetramethyl-3-phenylpyrazole-1-acetanilide having a melting point of 152°–154° C.

Analysis: Calc'd. for $C_{21}H_{23}N_3O$: C, 75.64; H, 6.95; N, 12.60. Found: C, 75.66; H, 7.09; N, 12.79.

EXAMPLE 58

N-Benzyl-α,α,4-trimethyl-3-phenylpyrazole-1-acetamide

Following the procedure of Example 49, but substituting benzylaminde for aqueous methylamine there was obtained N-benzyl-α,α,4-trimethyl-3-phenylpyrazole-1-acetamide having a melting point of 87°–90° 1 C.

Analysis: Calc'd. for $C_{21}H_{23}N_3O$: C, 75.64; H, 6.95; N, 12.60. Found: C, 75.40; H, 6.96; N, 12.28.

EXAMPLE 59

N,N,α,α,4-Pentamethyl-3-phenylpyrazole-1-acetamide and
N,N,α,4-tetramethyl-3-phenylpyrazole-1-propionamide Following the procedure of Example 49, but substituting aqueous dimethylamine for aqueous methylamine, there were obtained N,N,α,α,4-pentamethyl-3-phenylpyrazole-1-acetamide having a melting point of 107°–109° C.

Analysis: Calc'd. for $C_{16}H_{21}N_3O$: C, 70.82; H, 7.80; N, 15.49. Found: C, 70.98; H, 7.90; N, 15.73.

and N,N,α,4-tetramethyl-3-phenylpyrazole-1-propionamide having a melting point of 51°–54° C.

Analysis: Calc'd. for $C_{16}H_{21}N_3O$: C, 70.82; H, 7.80; N, 15.49. Found: C, 71.08; H, 7.79; N, 15.42.

Alternate Synthesis of N,N,α,α,4-pentamethyl-3-phenylpyrazole-1-acetamide

Sodium methoxide powder (65 g., 1.2 mole) was added slowly to a stirred mixture of 4-methyl-3-phenylpyrazole (158 g., 1.0 mole) and ethyl-2-bromoisobutyrate (238 g., 1.2 mole) at 100° C. After addition was complete the reaction was cooled slightly, 80 g. sodium hydroxide in 400 ml. of water, 100 ml. ethanol was added, and the solution was heated under reflux for 1 hour. After cooling the solution was extracted with ether to remove the unchanged 4-methyl-3-phenylpyrazole (ca 20 g.). The aqueous phase was carefully acidified with concentrated hydrochloric acid and the pyrazole acid was extracted into chloroform.

The chloroform was removed under reduced pressure, the residue was dissolved in benzene (500 ml.), thionyl chloride (140 g., 1.1 mole) added, and the mixture was stirred under reflux for 3 hours. After cooling the solution was added to a stirred solution of 25% aqueous dimethylamine (600 ml.) containing ice, the temperature was held below 30° C. during the addition. The benzene layer was separated, washed with water and evaporated. The dark brown residual oil was crystallized from methanol (ca 200 ml.) at −10° C. and then from benzene:Skellysolve B to give 110 g. of N,N,α,α,4-pentamethyl-3-phenylpyrazole-1-acetamide, m.p. 109°–111° C.

Additional product was obtained by chromatography of the mother liquors.

EXAMPLE 60

N,N-Diethyl-α,α,4-trimethyl-3-phenylpyrazole-1-acetamide

Following the procedure of Example 49, but substituting diethylamine for aqueous methylamine, there was obtained N,N-diethyl-α,α,4-trimethyl-3-phenylpyrazole-1-acetamide having melting point of 50°–52° C.

Analysis: Calc'd. for $C_{18}H_{25}N_3O$: C, 72.20; H, 8.42; N, 14.04. Found: C, 72.28; H, 8.44; N, 14.07.

EXAMPLE 61

N,α,α,4-Tetramethyl-N-octyl-3-phenylpyrazole-1-acetamide

Following the procedure of Example 49, but substituting N-methyloctylamine for aqueous methylamine, there was obtained N,α,α,4-tetramethyl-N-octyl-3-phenylpyrazole-1-acetamide having a melting point of 75°–78° C.

Analysis: Calc'd. for $C_{23}H_{35}N_3O$: C, 74.75; H, 9.55; N, 11.37. Found: C, 74.74; H, 9.43; N, 11.12.

EXAMPLE 62

N,N,α,α-Tetramethyl-3-phenylpyrazole-1-acetamide and N,N,α-trimethyl-3-phenylpyrazole-1-propionamide Following the procedure of Example 49, but substituting 3-phenylpyrazole for 4-methyl-3-phenylpyrazole and aqueous dimethylamine for aqueous methylamine there were obtained N,N,α,α-tetramethyl-3-phenylpyrazole-1-acetamide having a melting point of 99.5°–102° C.

Analysis: Calc'd. for $C_{15}H_{19}N_3O$: C, 70.00; H, 7.44; N, 16.33. Found: C, 69.83; H, 7.47; N, 16.16.
and N,N,α-trimethyl-3-phenylpyrazole-1-propionamide having a melting point of 69°–71.5° C.

Analysis: Calc'd. for $C_{15}H_{19}N_3O$: C, 70.00; H, 7.44; N, 16.33. Found: C, 69.97; H, 7.55; N, 15.90.

EXAMPLE 63

N,N-Diethyl-3-(2-furyl)-α,α,4-trimethylpyrazole-1-acetamide

Following the procedure of Example 49, but substituting 3-(2-furyl)-4-methylpyrazole for 4-methyl-3-phenylpyrazole and diethylamine for aqueous methylamine there was obtained N,N-diethyl-3-(2-furyl)-αα,4-trimethylpyrazole-1-acetamide having a melting point of 73°–76° C.

Analysis: Calc'd. for $C_{16}H_{23}N_3O_2$: C, 66.41; H, 8.01; N, 14.52. Found: C, 66.19; H, 7.83; N, 14.24.

EXAMPLE 64

3-(2-Furyl)-N,α,α,4-tetramethylpyrazole-1-acetamide

Following the procedure of Example 49, but substituting 3-(2-furyl)-4-methylpyrazole for 4-methyl-3-phenypyazole there was obtained 3-(2-furyl)-N-α,α,4-tetramethylpyrazole-1-acetamide having a melting point of 101°–103° C.

Analysis: Calc'd. for $C_{13}H_{17}N_3O_2$: C, 63.14; H, 6.93; N, 16.99. Found: C, 61.58; H, 6.69; N, 16.48.

EXAMPLE 65

3-(o-Chlorophenyl)-N,N,α,α,-tetramethylpyrazole-1-acetamide

Following the procedure of Example 49, but substituting 3-(o-chlorophenyl)pyrazole for 4-methyl-3-phenylpyrazole and dimethylamine for aqueous methylamine there was obtained 3-(o-chlorophenyl)-N,N,αα-tetramethylpyrazole-1-acetamide having a melting point of 79°–80.5° C.

Analysis: Calc'd. for $C_{15}H_{18}ClN_3O$: C, 61.74; H, 6.22; N, 14.40; Cl, 12.15. Found: C, 62.00; H, 6.45; N, 14.46; Cl, 12.06.

EXAMPLE 66

N,N,α,α,Tetramethyl-3-(o-tolyl)pyrazole-1-acetamide

Following the procedure of Example 49, but substituting 3-(o-tolyl)pyrazole for 4-methyl-3-phenylpyrazole and dimethylamine for aqueous methylamine there was obtained N,N,α,α-tetramethyl-3-(o-tolyl)-pyrazole-1-acetamide having a melting point of 78.5°–81° C.

Analysis: Calc'd. for $C_{16}H_{21}N_3O$: C, 70.82; H, 7.80; N, 15.49. Found: C, 70.62; H, 7.88; N, 15.69.

EXAMPLE 67

N,N,α,α,4-Pentamethyl-3-(o-tolyl)pyrazole-1-acetamide

Following the procedure of Example 49, but substituting 4-methyl-3-(o-tolyl)pyrazole for 4-methyl-3-phenylpyrazole and dimethylamine for methylamine there was obtained N,N,α,α,4-pentamethyl-3-(o-tolyl)-pyrazole-1-acetamide having a melting point of 145°–147° C.

Analysis: Calc'd. for $C_{17}H_{23}N_3O$: C, 71.54; H, 8.12; N, 14.73. Found: C, 71.51; H, 8.50; N, 14.83.

EXAMPLE 68

Part A — α,4-Dimethyl-3-phenylpyrazole-1-acetic acid

Sodium hydride (50.0 g., 57% in oil, 1.2 mole) was added over 20 minutes to a stirred solution of 4-methyl-3-phenylpyrazole (158 g., 1.0 mole) in THF (1.0 l.) maintained at 10°–20° C. Ethyl 2-bromopropionate (235 g., 1.3 mole) was added and the solution stirred for 18 hours, after which time ethanol was added and the solvent was removed by evaporation at reduced pressure. The residue was treated at 90° C. with sodium hydroxide (100 g., 2.5 mole) in 800 ml. 60% aqueous methanol for 30 minutes. After cooling, the solution was extracted with ether (3 × 200 ml.), and the aqueous phase was acidified with concentrated hydrochloric acid to give 148 g. of crude α,4-dimethyl-3-phenyl-pyrazole-1-acetic acid, m.p. 151°–162° C. Recrystallization from aqueous methanol gave 111 g. of product, m.p. 168°–172° C. The analytical sample was recrystallized from ethyl acetate, m.p. 170°–172° C.

Analysis: Calc'd for $C_{13}H_{14}N_2O_2$: C, 67.81; H, 6.13; N, 12.17. Found: C, 68.32; H, 6.14; N, 12.06.

Part B — α,4-Dimethyl-3-phenylpyrazole-1-acetamide

A mixture of α,4-dimethyl-3-phenylpyrazole-1-acetic acid (11.5 g., 0.05 mole), thionyl chloride (7.5 g., 0.06 mole) and benzene (300 ml.) was heated under reflux for 1 hour and cooled. Ammonia (30 ml. of 25% aqueous solution) was added rapidly with stirring to one-half of the above solution. The benzene layer was separated, washed with water, and the benzene evaporated. The residual oil (8.3 g.) was recrystallized twice from benzene:Skellysolve B to give 4.2 g. of α,4-dimethyl-3-phenylpyrazole-1-acetamide, m.p. 99°–101° C.

Analysis: Calc'd for $C_{13}H_{15}N_3O$: C, 68.10; H, 6.59; N, 18.33. Found: C, 69.09; H, 6.74; N, 18.47.

EXAMPLE 69

N,α,4-Trimethyl-3-phenylpyrazole-1-acetamide

Following the procedure of Example 68, but substituting aqueous methylamine for aqueous ammonia, there was obtained N,α,4-trimethyl-3-phenylpyrazole-1-acetamide having a melting point of 111°–112° C.

Analysis: Calc'd for $C_{14}H_{17}N_3O$: C, 69.11; H, 7.04; N, 17.27. Found: C, 69.10; H, 7.37; N, 17.29.

EXAMPLE 70

N-Ethyl-α,4-dimethyl-3-phenylpyrazole-1-acetamide

Following the procedure of Example 68, but substituting aqueous ethylamine for aqueous ammonia, there was obtained N-ethyl-α,4-dimethyl-3-phenylpyrazole-1-acetamide having a melting point of 78°–79° C.

Analysis: Calc'd for $C_{15}H_{19}N_3O$: C, 70.00; H, 7.44; N, 16.33. Found: C, 70.14; H, 7.30; N, 16.49.

Example 71

N-Butyl-α,4-dimethyl-3-phenylpyrazole-1-acetamide

Following the procedure of Example 68, but substituting butylamine for aqueous ammonia, there was obtained N-butyl-α,4-dimethyl-3-phenylpyrazole-1-acetamide having a melting point of 82°–84° C.

Analysis: Calc'd for $C_{17}H_{23}N_3O$: C, 71.54; H, 8.12; N, 14.73. Found: C, 72.42; H, 8.01; N, 14.91.

EXAMPLE 72

N-Ethyl-N,α,4-trimethyl-3-phenylpyrazole-1-acetamide

Following the procedure of Example 68, but substituting N-methyl ethylamide for aqueous ammonia, there was obtained N-ethyl-N,α,4-trimethyl-3-phenylpyrazole-1-acetamide having a melting point of 59°–61° C.

Analysis: Calc'd for $C_{16}H_{21}N_3O$: C, 70.82; H, 7.80; N, 15.49. Found: C, 71.15; H, 7.46; N. 15.71.

EXAMPLE 73

N,N-Diethyl-α,4-dimethyl-3-phenylpyrazole-1-acetamide

Following the procedure of Example 68, but substituting diethylamine for aqueous ammonia there was obtained N,N-diethyl-α,4-dimethyl-3-phenylpyrazole-1-acetamide having a melting point of 55°–57° C.

Analysis: Calc'd for $C_{17}H_{23}N_3O$: C, 71.54; H, 8.12; N, 14.73. Found: C, 71.54; H, 8.07; N, 14.82.

EXAMPLE 74

α,4Dimethyl-3-phenylpyrazole-1-acetanilide

Following the procedure of Example 68, but substituting aniline for aqueous ammonia, there was obtained α,4-dimethyl-3-phenylpyrazole-1-acetanilide having a melting point of 79°–82° C.

Analysis: Calc'd for $C_{19}H_{19}N_3O$: C, 74.73; H, 6.27; N, 13.76. Found: C, 75.97; H, 6.39; N, 13.17.

EXAMPLE 75

N,α,4-Trimethyl-3-phenylpyrazole-1-acetanilide

Following the procedure of Example 68, but substituting N-methylaniline for aqueous ammonia, there was obtained N,α,4-trimethyl-3-phenylpyrazole-1-acetanilide having a melting point of 111.5°–114.5° C.

Analysis: Calc'd for $C_{20}H_{21}N_3O$: C, 75.21; H, 6.63; N, 13.16. Found: C, 75.45; H, 6.50; N, 13.29.

EXAMPLE 76

[2-(4-Methyl-3-phenylpyrazol-1-yl)propionyl]-pyrrolidine

Following the procedure of Example 68, but substituting pyrrolidine for aqueous ammonia, there was obtained 1-[2-(4-methyl-3-phenylpyrazol-1-yl)propionyl]-pyrrolidine having a melting point of 72°–74° C.

Analysis: Calc'd for $C_{17}H_{21}N_3O$: C, 72.05; H, 7.47; N, 14.83. Found: C, 72.37; H, 7.62; N, 14.68.

EXAMPLE 77

4-[2-(4-Methyl-3-phenylpyrazol-1-yl)propionyl]-morpholine

Following the procedure of Example 68, but substituting morpholine for aqueous ammonia, there was obtained 4-[2-(4-methyl-3-phenylpyrazol-1-yl)propionyl]morpholine having a melting point of 84°–96° C.

Analysis: Calc'd for $C_{17}H_{21}N_3O_2$: C, 68.20; H, 7.07; N, 14.04. Found: C, 67.78; H, 7.11; N, 13.69.

EXAMPLE 78

α,4-Dimethyl-3-phenyl-N,N-dipropylpyrazole-1-acetamide

Following the procedure of Example 68, but substituting dipropylamine for aqueous ammonia, there was obtained α,4-dimethyl-3-phenyl-N,N-dipropylpyrazole-1-acetamide having a boiling point of 176°/0.6 mm.

Analysis: Calc'd for $C_{19}H_{27}N_3O$: C, 72.80; H, 8.68; N, 13.41. Found: C, 72.80; H, 8.75; N, 13.32.

EXAMPLE 79

4-Methyl-3-phenyl-α-propylpyrazole-1-acetamide

Following the procedure of Example 68, but substituting 4-methyl-3-phenyl-α-propylpyrazole-1-acetic acid for α,4-dimethyl-3-phenylpyrazole-1-acetic acid, there was obtained 4-methyl-3-phenyl-α-propylpyrazole-1-acetamide having a melting point of 116°–118° C.

Analysis: Calc'd. for $C_{15}H_{19}N_3O$: C, 70.00; H, 7.44; N, 16.33. Found: C, 70.11; H, 7.71; N, 16.60.

EXAMPLE 80

N,4-Dimethyl-3-phenyl-α-propylpyrazole-1-acetamide

Following the procedure of Example 68, but substituting aqueous methylamine for aqueous ammonia, and 4-methyl-3-phenyl-α-propylpyrazole-1-acetic acid for α,4-dimethyl-3-phenylpyrazole-1-acetic acid, there was obtained N,4-dimethyl-3-phenyl-α-propylpyrazole-1-acetamide having a melting point of 84°–86° C.

Analysis: Calc'd. for $C_{16}H_{21}N_3O$: C, 70.82; H, 7.80; N, 15.49. Found: C, 70.42; H, 7.98; N, 15.52.

EXAMPLE 81

N,N,4-Trimethyl-3-phenyl-α-propylpyrazole-1-acetamide

Following the procedure of Example 68, but substituting dimethylamine for aqueous ammonia and 4-methyl-3-phenyl-α-propylpyrazole-1-acetic acid for α,4-dimethyl-3-phenylpyrazole-1-acetic acid, there was obtained N,N,4-trimethyl-3-phenyl-α-propylpyrazole-1-acetamide having a melting point of 84°–86° C.

Analysis: Calc'd. for $C_{17}H_{23}N_3O$: C, 71.54; H, L8.12; N, 14.73. Found: C, 71.47; H, 8.22; N,14,91.

EXAMPLE 82

N,N-Diethyl-4-methyl-3-phenyl-α-propylpyrazole-1-acetamide

Following the procedure of Example 68, but substituting diethylamine for aqueous ammonia and 4-methyl-3-phenyl-α-propylpyrazole-1-acetic acid for α,4-dimethyl-3-phenylpyrazole-1-acetic acid, there was obtained N,N-diethyl-4-methyl-3-phenyl-α-propylpyrazole-1acetamide having a melting point of 65°–67° C.

Analysis: Calc'd. for $C_{19}H_{27}N_3O$: C, 72.80; H, 8.68; N, 13.41. Found: C, 73.00; H, 8.73; N, 13.59.

EXAMPLE 83

N,N-Diethyl-α-methyl-3-phenylpyrazole-1-acetamide

Following the procedure of Example 68, but substituting α-methyl-3-phenylpyrazole-1-acetic acid for α,4-dimethyl-3-phenylpyrazole-1-acetic acid, and diethylamine for aqueous ammonia there was obtained N,N-diethyl-α-methyl-3-phenylpyrazole-1-acetamide having a boiling point of 178°/0.2 mm.

Analysis: Calc'd. for $C_{16}H_{21}N_3O$: C, 70.82; H, 7.80; N, 15.49. Found: C, 70.60; H, 7.74; N, 15.51.

EXAMPLE 84

α-Methyl-3-phenyl-N,N-dipropylpyrazole-1-acetamide

Following the procedure of Example 68, but substituting dipropylamine for aqueous ammonia and α-methyl-3-phenylpyrazole-1-acetic acid for α,4-dimethyl-3-phenylpyrazole-1-acetic acid, there was obtained α-methyl-3-phenyl-N,N-dipropylpyrazole-1-acetamide having a boiling point of 181°/0.4 mm.

Analysis: Calc'd. for $C_{18}H_{25}N_3O$: C, 72.20; H, 8.42; N, 14.04. Found: C, 72.03; H, 8.69; N, 13.90.

EXAMPLE 85

α-Ethyl-N,N-dimethyl-3-phenylpyrazole-1-acetamide

Following the procedure of Example 68, but substituting α-ethyl-3-phenylpyrazole-1-acetic acid for α,4-dimethyl-3-phenylpyrazole-1-acetic acid, and dimethylamine for aqueous ammonia, there was obtained α-ethyl-N,N-dimethyl-3-phenylpyrazole-1-acetamide having a melting point of 101°-103° C.

Analysis: Calc'd. for $C_{15}H_{19}N_3O$: C, 70.00; H, 7.44; N, 16.33. Found: C, 70.16; H, 7.48; N, 16.14.

EXAMPLE 86

N,N,α-Triethyl-3-phenylpyrazole-1-acetamide

Following the procedure of Example 68, but substituting α-ethyl-3-phenylpyrazole-1-acetic acid for α,4-dimethyl-3-phenylpyrazole-1-acetic acid, and diethylamine for aqueous ammonia, there was obtained N,N,α-triethyl-3-phenylpyrazole-1-acetamide having a melting point of 63°-66° C.

Analysis: Calc'd. for $C_{17}H_{23}N_3O$: C, 71.54; H, 8.12; N, 14.73. Found: C, 71.85; H, 8.12; N, 14.71.

EXAMPLE 87

N,N,α-Triethyl-4-methyl-3-phenylpyrazole-1-acetamide

Following the procedure of Example 68, but substituting α-ethyl-4-methyl-3-phenylpyrazole-1-acetic acid for α,4-dimethyl-3-phenylpyrazole-1-acetic acid, and diethylamine for aqueous ammonia, there was obtained N,N,α-triethyl-4-methyl-3-phenylpyrazole-1-acetamide having a melting point of 80°-82° C.

Analysis: Calc'd. for $C_{18}H_{25}N_3O$: C, 72.20; H, 8.42; N, 14.01. Found: C, 73.34; H, 8.73; N, 14.47.

EXAMPLE 88

α-Isopropyl-N,N,4-trimethyl-3-phenylpyrazole-1-acetamide

Following the procedure of Example 68, but substituting α-isopropyl-4-methyl-3-phenylpyrazole-1-acetic acid for α,4-dimethyl-3-phenylpyrazole-1-acetic acid, and dimethylamine for aqueous ammonia, there was obtained α-isopropyl-N,N,4-trimethyl-3-phenylpyrazole-1-acetamide having a melting point of 66.5°-68.5° C.

Analysis: Calc'd. for $C_{17}H_{23}N_3O$: C, 71.54; H, 8.12; N, 14.73. Found: C, 71.67; H, 8.15; N, 14.63.

EXAMPLE 89

4-Chloro-α-ethyl-N,N-dimethyl-3-phenylpyrazole-1-acetamide

Following the procedure of Example 68, but substituting 4-chloro-α-ethyl-3-phenylpyrazole-1-acetic acid for α,4-dimethyl-3-phenylpyrazole-1-acetic acid, and dimethylamine for aqueous ammonia, there was obtained 4-chloro-α-ethyl-N,N-dimethyl-3-phenylpyrazole-1-acetamide having a melting point of 94°-96.5° C.

Analysis: Calc'd. for $C_{15}H_{18}ClN_3O$: C, 61.74; H, 6.22; N, 14.40; Cl, 12.15. Found: C, 62.22; H, 6.26; N, 14.29; Cl, 12.07.

Alternate Synthesis of 4-chloro-α-ethyl-N,N-dimethyl-3-phenylpyrazole-1-acetamide α-Ethyl-N,N-dimethyl-3-phenylpyrazole-1-acetamide (51.4 g., 0.2 mole) was dissolved in chloroform (200 ml.). A solution of potassium carbonate (28.0 g.) in water (100 ml.) was added. The two-phase reaction mixture was stirred vigorously at 10° C during the addition of chlorine (10 ml., 14.7 g., 0.2 mole). After addition was complete, the organic phase was separated, washed with water, and the solvents were removed under reduced pressure. The residue was dissolved in benzene (60 ml.) and Skellysolve B (300 ml.) was added. The solution was cooled to −10° C. and filtered to afford 56.7 g. of 4-chloro-α-ethyl-N,N-dimethyl-3-phenylpyrazole-1-acetamide, m.p. 95°-97° C.

EXAMPLE 90

4-Chloro-N,N,α-triethyl-3-phenylpyrazole-1-acetamide

Following the procedure of Example 68, but substituting 4-chloro-α-ethyl-3-phenylpyrazole-1-acetic acid for α,4-dimethyl-3-phenylpyrazole-1-acetic acid and diethylamine for aqueous ammonia there was obtained 4-chloro-N,N,α-triethyl-3-phenylpyrazole-1-acetamide having a melting point of 47°-49° C.

Analysis: Calc'd. for $C_{17}H_{22}ClN_3O$: C, 63.84; H, 6.93; N, 13.14; Cl, 11.09. Found: C, 63.97; H, 6.97; N, 12.94; Cl, 11.01.

EXAMPLE 91

4-Chloro-α-ethyl-3-phenyl-N,N-dipropylpyrazole-1-acetamide

Following the procedure of Example 68, but substituting 4-chloro-α-ethyl-3-phenylpyrazole-1-acetic acid for α,4-dimethyl-3-phenylpyrazole-1-acetic acid, and dipropylamine for aqueous ammonia, there was obtained 4-chloro-α-ethyl-3-phenyl-N,N-dipropylpyrazole-1-acetamide having a boiling point of 184°/0.25 mm.

Analysis: Calc'd. for $C_{19}H_{26}ClN_3O$: C, 65.59; H, 7.53; N, 12.08; Cl, 10.19. Found: C, 66.56; H, 7.99; N, 12.25; Cl, 10.52.

EXAMPLE 92

N,N-Dimethyl-3-phenyl-α-propylpyrazole-1-acetamide

Following the procedure of Example 68, but substituting 3-phenyl-α-propylpyrazole-1-acetic acid for α,4- dimethyl-3-phenylpyrazole-1-acetic acid and aqueous dimethylamine for aqueous ammonia there was obtained N,N,-dimethyl-3-phenyl-α-propylpyrazole-1-acetamide having a boiling point of 180°–181°/0.1 mm.

Analysis: Calc'd. for $C_{16}H_{21}N_3O$: C, 70.82; H, 7.80; N, 15.49. Found: C, 70.53; H, 7.86; N, 15.67.

EXAMPLE 93

N,N,4-Trimethyl-α,3-diphenylpyrazole-1-acetamide

Following the procedure of Example 68, but substituting 4-methyl-α,3-diphenylpyrazole-1-acetic acid for α,4-dimethyl-3-phenylpyrazole-1-acetic acid and dimethylamine for aqueous ammonia, there was obtained N,N,4-trimethyl-α,3-diphenylpyrazole-1-acetamide having a melting point of 135.5°–138° C.

Analysis: Calc'd. for $C_{20}H_{21}N_3O$: C, 75.21; H, 6.63; N, 13.16. Found: C, 75.37; N, 6.76; N, 13.28.

EXAMPLE 94

4-Cyano-N,N,α-trimethyl-3-phenylpyrazole-1-acetamide

A mixture of 4-bromo-N,N,α-trimethyl-3-phenylpyrazole-1-acetamide (8.0 g., 0.025 mole) cuprous cyanide (25.0 g., 0.28 mole) and dimethylformamide (200 ml.) was heated under reflux for 18 hours. Water was added and the solution was repeatedly extracted with chloroform. Evaporation of the chloroform gave a residue (7.5 g.), which was recyrstallized from benzene:Skellysolve B to give 6.5 g. of 4-cyano-N,N,α-trimethyl-3-phenylpyrazole-1-acetamide, m.p. 143°–146° C. Two recrystallizations from ethyl acetate gave the analytical sample, m.p. 144°–146° C.

Analysis: Calc'd. for $C_{15}H_{16}N_4O$: C, 67.14; H, 6.01; N, 20.88. Found: C, 67.12; H, 6.12; N, 21.18.

EXAMPLE 95

α-Ethyl-N,N,α,4-tetramethyl-3-phenylpyrazole-1-acetamide n-Butyl lithium (40 ml. of 1.6 M solution in hexane, 0.06 mole) was added under nitrogen to a stirred solution of N,N,α,4-tetramethyl-3-phenylpyrazole-1-acetamide (12.8 g., 0.05 mole) in THF (150 ml.). Ethyl iodide (30 g.) was added. The solvent was removed after 30 minutes and the residue was partitioned between chloroform and water. The chloroform was evaporated and the residual oil was chromatographed on silica gel using benzene:ethyl acetate (9:1) as eluant. α-Ethyl-N,Nα,4-tetramethyl-3-phenylpyrazole-1-acetamide (4.9 g.) was the second major band to be eluted from the column. Recrystallization from methanol followed by cyclohexane gave the analytical sample, m.p. 102°–104° C.

Analysis: Calc'd. for $C_{17}H_{23}N_3O$: C, 71.54; H, 8.12; N, 14.73. Found: C, 71.59; H, 7.75; N, 14.91.

EXAMPLE 96

N,N,α,4-Tetramethyl-3-phenyl-α-propylpyrazole-1-acetamide

Following the procedure of Example 95, but substituting propyl bromide for ethyl iodide, there was obtained N,N,α,4-tetramethyl-3-phenyl-α-propylpyrazole-1-acetamide having a melting point of 90°–92° C.

Analysis: Calc'd. for $C_{18}H_{25}N_3O$: C, 72.20; H, 8.42; N, 1401. Found: C: C, 72.17; H, 8.39; N, 13.97.

EXAMPLE 97

α,α-Diethyl-N,N,4-trimethyl-3-phenylpyrazole-1-acetamide

Following the procedure of Example 95, but substituting α-ethyl-N,N,4-trimethyl-3-phenylpyrazole-1-acetamide for N,N,α,4-tetramethyl-3-phenylpyrazole-1-acetamide, there was obtained α,α-diethyl-N,N,4-trimethyl-3-phenylpyrazole-1-acetamide having a melting point of 135°–136.5° C.

Analysis: Calc'd. for $C_{18}H_{25}N_3O$: C, 72.20; H, 8.42; N, 14.01. Found: C, 72.40; H, 8.27; N, 14.17.

EXAMPLE 98

α-Ethyl-N,N,4-trimethyl-3-phenyl-α-propylpyrazole-1-acetamide

Following the procedure of Example 95, but substituting α-ethyl-N,N,4-trimethyl-3-phenylpyrazole-1-acetamide for N,N,α,4-tetramethyl-3-phenylpyrazole-1-acetamide and propyl bromide for ethyl iodide, there was obtained α-ethyl-N,N,4-trimethyl-3-phenyl-α-propylpyrazole-1-acetamide having a melting point of 147°–148° C.

Analysis: Calc'd. for $C_{19}H_{27}N_3O$: C, 72.80; H, 8.68; N, 13.41. Found: C, 72.85; H, 8.44; N, 13.75.

EXAMPLE 99

N,N,α,α,4-Pentamethyl-5-phenylpyrazole-1-acetamide

Following the procedure of Example 95, but substituting N,N,α,4-tetramethyl-5-phenylpyrazole-1-acetamide for N,N,α,4-tetramethyl-3-phenylpyrazole-1-acetamide and methyl iodide for ethyl iodide, there was obtained N,N,α,α,4-pentamethyl-5-phenylpyrazole-1-acetamide having a melting point of 136°–139° C.

Analysis: Calc'd. for $C_{16}H_{21}H_3O$: C, 70.82; H, 7.80; N, 15.49. Found: C, 71.03; H, 7.98; N, 15.74.

EXAMPLE 100

N,N,α,4-Tetramethyl-α,3-diphenylpyrazole-1-acetamide

Following the procedure of Example 95, but substituting N,N,4-trimethyl-α,3-diphenylpyrazole-1-acetamide for N,N,α,4-tetramethyl-3-phenylpyrazole-1-acetamide and methyl iodide for ethyl iodide, there was obtained N,N,α,4-tetramethyl-α,3-diphenylpyrazole-1-acetamide having a melting point of 107°–109° C.

Analysis: Calc'd. for $C_{21}H_{23}N_3O$: C, 75.64; H, 6.95; N, 12.60. Found: C, 75.61; H, 7.08; N, 12.46.

EXAMPLE 101

N,N,α,α,4-Pentamethyl-3-(2-thienyl)pyrazole-1-acetamide

Following the procedure of Example 95, but substituting N,N,α,4-tetramethyl-3-(2-thienyl)pyrazole-1-acetamide for N,N,α,4-tetramethyl-3-phenylpyrazole-1-acetamide and methyl iodide for ethyl iodide there was obtained N,N,α,α,4-pentamethyl-3-(2-thienyl)pyrazole-1-acetamide having a melting point of 116°–119° C.

Analysis: Calc'd. for $C_{14}H_{19}N_3OS$: C, 60.62; H 6.90; N, 15.15; S, 11.56. Found: C, 60.82; H, 6.88; N, 14.92; S, 11.78.

EXAMPLE 102

3-(2-Furyl)-N,N,α,α,4-pentamethylpyrazole-1-acetamide

Following the procedure of Example 95, but substituting 3-(2-furyl)-N,N,α,4-tetramethylpyrazole-1-acetamide for N,N,α,4-tetramethyl-3-phenylpyrazole-1-acetamide and methyl iodiode for ethyl iodide there was obtained 3-(2-furyl)N,N,α,α,4-pentamethylpyrazole-1-acetamide having a melting point of 131°–134° C.

Analysis: Calc'd. for $C_{14}H_{19}N_3O_2$: C, 64.34; H, 7.33; N, 16.08. Found: C, 62.90; H, 7.03; N, 15.87.

EXAMPLE 103

N,N-Dimethyl-1-(4-methyl-3-phenylpyrazol-1-yl)cyclopropanecarboxamide

Following the procedure of Example 95, but substituting α-(2-chloroethyl)-N,N,4-trimethyl-3-phenylpyrazole-1-acetamide (prepared in Example 45) for N,N,α,4-tetramethyl-3-phenylpyrazole-1-acetamide and without addition of ethyl iodide there was obtained N,N-dimethyl-1-(4-methyl-3-phenylpyrazol-1-yl)cyclopropanecarboxamide, m.p. 52°–55° C.

Analysis: Calc'd, for $C_{16}H_{19}N_3O$: C, 71.34; H, 7.11; N, 15.60. Found: C, 71.23; H, 7.13; N, 15.67.

EXAMPLE 104

N,N-Dimethyl-1-(4-methyl-3-phenylpyrazol-1-yl)cyclobutanecarboxamide

Following the procedure of Example 95, but substituting α-(3-bromopropyl)-N,N,4-trimethyl-3-phenylpyrazole-1-acetamide for N,N,α,4-tetramethyl-3-phenylpyrazole-1-acetamide and without the addition of ethyl iodide there was obtained N,N-dimethyl-1-(4-methyl-3-phenylpyrazol-1-yl)cyclobutanecarboxamide having a melting point of 87°–89° C.

Analysis: Calc'd. for $C_{17}H_{21}N_3O$: C, 72.05; H, 7.47; N, 14.83. Found: C, 71.83; H, 7.82; N, 14.89.

EXAMPLE 105

N,N-Dimethyl-1-(4-methyl-3-phenylpyrazol-1-yl)cyclopentanecarboxamide

Following the procedure of Example 95, but substituting α-(4-bromobutyl)-N,N,4-trimethyl-3-phenylpyrazole-1-acetamide (prepared in Example 43) for N,N,α,4-tetramethyl-3-phenylpyrazole-1-acetamide and without addition of ethyl iodide there was obtained N,N-dimethyl-1-(4-methyl-3-phenylpyrazol-1-yl)cyclopentanecarboxamide

EXAMPLE 106

N,N-Dimethyl-1-(3-phenylpyrazol-1-yl)cyclopropanecarboxamide

Following the procedure of Example 95, but substituting α-(2-chloroethyl)-N,N-dimethyl-3-phenylpyrazole-1-acetamide for N,N,α,4-tetramethyl-3-phenylpyrazole-1-acetamide and without addition of ethyl iodide there was obtained N,N-dimethyl-1-(3-phenylpyrazol-1-yl)cyclopropanecarboxamide having a melting point of 96°–99° C.

Analysis: Calc'd. for $C_{15}H_{17}N_3O$: C, 70.56; H, 6.71; N, 16.48. Found: C, 70.19; H, 6.68; N, 16.46.

EXAMPLE 107

N,N-Dimethyl-1-(3-phenylpyrazol-1-yl)cyclobutanecarboxamide

Following the procedure of Example 95, but substituting α-(3-bromopropyl)-N,N-dimethyl-3-phenylpyrazole-1-acetamide for N,N,α,4-tetramethyl-3-phenylpyrazole-1-acetamide and without addition of ethyl iodide there was obtained N,N-dimethyl-1-(3-phenylpyrazol-1-yl)cyclobutanecarboxamide having a boiling point of 170°/0.1 mm.

Analysis: Calc'd. for $C_{16}H_{19}N_3O$: C, 71.34; H, 7.11; N, 15.60. Found: C, 71.42; H, 7.19; N, 14.63.

EXAMPLE 108

4-Bromo-N,Nα,5-tetramethyl-3-phenylpyrazole-1-acetamide

Bromine (3.68 g., .023 mole) was added to a solution of N,N,α,5-tetramethyl-3-phenylpyrazole-1-acetamide (5.0 g., .019 mole) in acetic acid. After 1 hour, the solution was diluted with water to give 6.3 g. of 4-bromo-N,N,α,4-tetramethyl-3-phenylpyrazole-1-acetamide, m.p. 88°–89.5° C. Recrystallization from benzene-Skellysolve B and finally ether gave the analytical sample, m.p. 88°–89.5° C.

Analysis: Calc'd. for $C_{15}H_{18}BrN_3O$: C, 53.58; H, 5.40; Br, 23.77; N, 12.50. Found: C, 53.69; H, 5.54; Br, 23.69; N, 12.30.

EXAMPLE 109

4-Bromo-α-ethyl-N,N-dimethyl-3-phenylpyrazole-1-acetamide

Following the procedure of Example 108, but substituting α-ethyl-N,N-dimethyl-3-phenylpyrazole-1-acetamide for N,N,α,5-tetramethyl-3-phenylpyrazole-1-acetamide, there was obtained 4-bromo-α-ethyl-N,N-dimethylpyrazole-1-acetamide having a melting point of 97°–100° C.

Analysis: Calc'd. for $C_{15}H_{18}BrN_3O$: C, 53.58; H, 5.40; N, 12.48; Br, 23.77. Found: C, 53.75; H, 5.45; N, 12.68; Br, 23.75.

EXAMPLE 110

4-Chloro-3-(p-chlorophenyl)-N,N,α-trimethylpyrazole-1-acetamide

Following the procedure of Example 108, but substituting 3-(p-chlorophenyl)-N,N,α-trimethylpyrazole-1-acetamide for N,N,α,5-tetramethyl-3-phenylpyrazole-1-acetamide and sulfuryl chloride for bromine, there was obtained 4-chloro-3-(p-chlorophenyl)-N,N,α-trimethylpyrazole-1-acetamide having a melting point of 92°–93.5° C.

Analysis: Calc'd. for $C_{14}H_{15}Cl_2N_3O$: C, 53.86; H, 4.84; N, 13.46; Cl, 22.71. Found: C, 54.00; H, 4.88; N, 13.41; Cl, 22.74.

EXAMPLE 111

4-Chloro-3-(o-chlorophenyl)-N,N,α-trimethylpyrazole-1-acetamide

Following the procedure of Example 108, but substituting 3-(o-chlorophenyl)-N,N,α-trimethylpyrazole-1-acetamide for N,N,α,5-tetramethyl-3-phenylpyrazole-1-acetamide, tert-butyl hypochlorite for bromine, and carbon tetrachloride for acetic acid as the reaction solvent, there was obtained 4-chloro-3-(o-chlorophenyl)-

N,N,α-trimethylpyrazole-1-acetamide having a melting point of 108°-111° C.

Analysis: Calc'd. for $C_{14}H_{15}Cl_2N_3O$: C, 53.86; H, 4.84; N, 22.71; Cl, 13.46. Found: C, 53.77; H, 4.89; N, 22.87; Cl, 13.29.

EXAMPLE 112

4-Chloro-N,N,α-trimethyl-3-(o-tolyl)pyrazole-1-acetamide

Following the procedure of Example 108, but substituting N,N,α-trimethyl-3-(o-tolyl)pyrazole-1-acetamide for N,N,α,5-tetramethyl-3-phenylpyrazole-1-acetamide, tert-butyl hypochlorite for bromine, and carbon tetrachloride for acetic acid as the reaction solvent, there was obtained 4-chloro-N,N,α-trimethyl-3-(o-tolyl)pyrazole-1-acetamide having a melting point of 69°-71.5° C.

Analysis: Calc'd. for $C_{15}H_{18}ClN_3O$: C, 61.74; H, 6.22; H, 14.40; Cl, 12.15. Found: C, 61.59; H, 6.32; N, 14.32; Cl, 12.17.

EXAMPLE 113

4-Chloro-N,N,α-trimethyl-3-(o-methoxyphenyl)-pyrazole-1-acetamide

Following the procedure of Example 108, but substituting N,N,α-trimethyl-3-(o-methoxyphenyl)pyrazole-1-acetamide for N,N,α,5-tetramethyl-3-phenylpyrazole-1-acetamide, tert-butyl hypochlorite for bromine, and carbon tetrachloride for acetic acid as the reaction solvent, there was obtained 4-chloro-N,N,α-trimethyl-3-(o-methoxyphenyl)pyrazole-1-acetamide having a melting point of 74°-77° C.

Analysis: Calc'd. for $C_{15}H_{18}ClN_3O_2$: C, 58.53; H, 5.89; N, 11.52; Cl, 13.65. Found: C, 58.70; H, 5.95; N, 11.48; Cl, 13.88.

EXAMPLE 114

4-Chloro-N,N,α,α-tetramethyl-3-phenylpyrazole-1-acetamide

Following the procedure of Example 108, but substituting N,N,α,α-tetramethyl-3-phenylpyrazole-1-acetamide for N,N,α,5-tetramethyl-3-phenylpyrazole-1-acetamide, tert-butyl hypochlorite for bromine, and carbon tetrachloride for acetic acid as the reaction solvent, there was obtained 4-chloro-N,N,α,α-tetramethyl-3-phenylpyrazole-1-acetamide having a melting point of 117°-119° C.

Analysis: Calc'd. for $C_{15}H_{18}ClN_3O$: C, 61.74; H, 6.22; N, 14.40; Cl, 12.15. Found: C, 61.53; H, 6.33; N, 14.36; Cl, 12.15.

EXAMPLE 115

4-Chloro-N,N-dimethyl-3-phenyl-α-propylpyrazole-1-acetamide

Following the procedure of Example 108, but substituting N,N-dimethyl-3-phenyl-α-propylpyrazole-1-acetamide for N,N,α,5-tetramethyl-3-phenylpyrazole-1-acetamide, tert-butyl hypochlorite for bromine, and carbon tetrachloride for acetic acid as the reaction solvent, there was obtained 4-chloro-N,N-dimethyl-3-phenyl-α-propylpyrazole-1-acetamide having a melting point of 85°-87° C.

Analysis: Calc'd. for $C_{16}H_{20}ClN_3O$: C, 62.84; H, 6.59; N, 13.74; Cl, 11.59. Found: C, 62.95; H, 6.84; N, 13.83; Cl, 11.68.

EXAMPLE 116

4-Chloro-N,N,α-trimethyl-3-(2,6-dichlorophenyl)-pyrazole-1-acetamide

Following the procedure of Example 108, but substituting N,N,α-trimethyl-3-(2,6-dichlorophenyl)-pyrazole-1-acetamide for N,N,α,5-tetramethyl-3-phenylpyrazole-1-acetamide, tert-butyl hyprochlorite for bromine, and carbon tetrachloride for acetic acid as the reaction solvent, there was obtained 4-chloro-N,N,α-trimethyl-3-(2,6-dichlorophenyl)pyrazole-1-acetamide having a melting point of 126°-128° C.

Analysis: Calc'd. for $C_{14}H_{14}Cl_3N_3O$: C, 48.51; H, 4.07; N, 12.12; Cl, 30.69. Found: C, 49.06; H, 4.15; N, 12.09; Cl, 30.59.

EXAMPLE 117

4-Chloro-N,N,α-trimethyl-3-phenylpyrazole-1-propionamide

Following the procedure of Example 108, but substituting N,N,α-trimethyl-3-phenylpyrazole-1-propionamide for N,N,α,5-tetramethyl-3-phenylpyrazole-1-acetamide, and tert-butyl hypochlorite for bromine, there was obtained 4-chloro-N,N,α-trimethyl-3-phenylpyrazole-1-propionamide having a boiling point of 190°/0.3 mm.

Analysis: Calc'd. for $C_{15}H_{18}ClN_3O$: C, 61.74; H, 6.22; N, 14.40; Cl, 12.15. Found: C, 61.82; H, 6.48; N, 14.57; Cl, 12.39.

EXAMPLE 118

4-Chloro-3-(o-chlorophenyl)-α-ethyl-N,N-dimethyl-pyrazole-1-acetamide

Following the procedure of Example 108, but substituting 3-(o-chlorophenyl)-α-ethyl-N,N-dimethyl-pyrazole-1-acetamide for N,N,α,5-tetramethyl-3-phenylpyrazole-1-acetamide, and tert-butyl hypochlorite for bromine, there was obtained 4-chloro-3-(o-chlorophenyl)-α-ethyl-N,N-dimethylpyrazole-1-acetamide.

Analysis: Calc'd. for $C_{15}H_{17}Cl_2N_3O$: C, 55.22; H, 5.26; N, 12.88; Cl, 21.74. Found: C, 55.23; H, 5.26; N, 12.93; Cl, 21.44.

EXAMPLE 119

4-Chloro-3-(o-chlorophenyl)-N,N,α,α-tetramethyl-pyrazole-1-acetamide

Following the procedure of Example 108, but substituting 3-(o-chlorophenyl)-N,N,α,α-tetramethyl-pyrazole-1-acetamide for N,N,α,5-tetramethyl-3-phenylpyrazole-1-acetamide, and tert-butyl hypochlorite for bromine, there was obtained 4-chloro-3-(o-chlorophenyl)-N,N,αα-tetramethylpyrazole-1-acetamide.

EXAMPLE 120

4-Chloro-N,N,α,α-tetramethyl-3-(o-tolyl)pyrazole-1-acetamide

Following the procedure of Example 108, but substituting N,N,α,α-tetramethyl-3-(o-tolyl)pyrazole-1-acetamide for N,N,α,5-tetramethyl-3-phenylpyrazole-1-acetamide and tert-butyl hypochlorite for bromine, there was obtained 4-chloro-N,N,α,α-tetramethyl-3-(o-tolyl)pyrazole-1-acetamide having a melting point of 134.5°-136° C.

Analysis: Calc'd. for $C_{16}H_{20}ClN_3O$: C, 62.84; H, 6.59; N, 13.74; Cl, 11.59. Found: C, 62.77; H, 6.73; N, 13.67; Cl, 11.58.

EXAMPLE 121

Alternate synthesis for
N,N,α-trimethyl-3-phenylpyrazole-1-propionamide

A mixture of 14.4 g. (0.1 mole of 3-phenylpyrazole, 20.8 g. (0.15 mole) of anhydrous potassium carbonate and 29.1 g. (0.15 mole) of 2-bromo-N,N,2-trimethylpropionamide was stirred at 140° C. for 1.5 hour. The mixture was diluted with water and extracted with benzene. Evaporation of the benzene gave an oil which was crystallized from cyclohexane to give 7.8 g. of N,N,α-trimethyl-3-phenylpyrazole-1-propionamide, m.p. 68°-71° C.

EXAMPLE 122

N,N,β,4-Tetramethyl-3-phenylpyrazole-1-propionamide

Following the procedure of Example 121, but substituting 2-bromo-N,N-dimethylbutyramide for 2-bromo-N,N,2-trimethylpropionamide, and 4-methyl-3-phenylpyrazole for 3-phenylpyrazole, there were obtained the already described α-ethyl-N,N,4-trimethyl-3-phenylpyrazole-1-acetamide and N,N,β,4-tetramethyl-3-phenylpyrazole-1-propionamide having a boiling point of 170°/0.2 mm.

Analysis: Calc'd. for $C_{16}H_{21}N_3O$: C, 70.82; H, 7.80; N, 15.49. Found: C, 70.87; H, 7.92; N, 15.84.

EXAMPLE 123

β-Ethyl-N,N-dimethyl-3-phenylpyrazole-1-propionamide

Following the procedure of Example 121, but substituting 2-bromo-N,N-dimethylvaleramide for 2-bromo-N,N,2-trimethyopropionamide, there were obtained the already described N,N-dimethyl-3-phenyl-α-propylpyrazole-1-acetamide and β-ethyl-N,N-dimethyl-3-phenylpyrazole-1-propionamide having a melting point of 97°-99° C.

Analysis: Calc'd. for $C_{15}H_{21}N_3O$: C, 70.82, H, 7.80; N, 15.49. Found: C, 70.75; H, 7.84; N, 15.56.

EXAMPLE 124

N,N-Dimethyl-3-phenylpyrazole-1-propionamide

Following the procedure of Example 121, but substituting 2-bromo-N,N-dimethylpropionamide for 2-bromo-N,N,2-trimethylpropionamide there were obtained the already described N,N,α-trimethyl-3-phenylpyrazole-1-acetamide and N,N-dimethyl-3-phenylpyrazole-1-propionamide having a melting point of 103°-105° C.

Analysis: Calc'd. for $C_{14}H_{17}N_3O$: C, 69.11; H, 7.04; N, 17.27. Found: C, 68.98; H, 6.92; N, 17.00.

EXAMPLE 125

N,N,β-Trimethyl-3-phenylpyrazole-1-propionamide

Following the procedure of Example 121, but substituting 2bromo-N,N-dimethylbutyramide for 2-bromo-N,N,2-trimethylpropionamide there was obtained the already described α-ethyl-N,N-dimethyl-3-phenyl-pyrazole-1-acetamide and N,N,β-trimethyl-3-phenylpyrazole-1-propionamide having a melting point of 65°-67° C.

Analysis: Calc'd. for $C_{15}H_{19}N_3O$: C, 70.00; H, 7.44; N, 16.33. Found: C, 69.94; H, 7.47; N, 16.56.

EXAMPLE 126

α-Bromo-N,N,4-trimethyl-3-phenylpyrazole-1-propionamide

Following the procedure of Example 121, but substituting 2,3-dibromo-N,N-dimethylpropionamide for 2-bromo-N,N,2-trimethylpropionamide and 4-methyl-3-phenylpyrazole for 3-phenylpyrazole there was obtained α-bromo-N,N,4-trimethyl-3-phenylpyrazole-1-propionamide having a melting point of 104°-107° C.

Analysis: Calc'd. for $C_{15}H_{18}BrN_3O$: C, 53.58; H, 5.39; N, 12.50; Br, 23.77. Found: C, 53.99; H, 5.51; N, 12.63; Br, 23.43.

EXAMPLE 127

N,N,α,α,4-Pentamethyl-3-phenylpyrazole-1-thioacetamide

N,N,α,α,4-Pentamethyl-3-phenylpyrazole-1-acetamide (2.71 g., 0.01 mole) was dissolved in 10 ml. of pyridine with stirring. To this solution was added phosphorous pentasulfide (3.33 g., 0.015 mole) and the mixture heated at reflux for one hour. The reaction mixture was partitioned in water-benzene, the benzene layer separated and washed with water. Evaporation of the benzene gave 2.75 g. of crude material which was chromatographed on silica gel. Elution with 10% ethyl acetate in benzene gave 2.65 gm. of N,N,α,α,4-pentamethyl-3-phenylpyrazole-1-thioacetamide which was recrystallized from ethyl acetate:Skellysolve B to give 2.0 g. having a melting point of 115°-117° C.

Analysis: Calc'd. for $C_{16}H_{21}N_3S$: C, 66.86; H, 7.37; N, 14.62; S, 11.15. Found: C, 66.82; H, 7.58; N, 14.53; S 11.27.

EXAMPLE 128

α-(n-Butyl)-N,N,4-trimethyl-3-phenylpyrazole-1-thioacetamide

Following the procedure of Example 127, but substituting α-(n-butyl)-N,N,4-trimethyl-3-phenylpyrazole-1-acetamide for N,N,α,α,4-pentamethyl-3-phenylpyrazole-1-acetamide there was obtained α-(n-butyl)-N,N,4-trimethyl-3-phenylpyrazole-1-thioacetamide having a melting point of 93°-95° C.

Analysis: Calc'd. for $C_{18}H_{25}N_3S$: C, 68.53; H, 7.99; N, 13.32; S, 10.16. Found: C, 68.31; H, 8.27; N, 13.39; S, 10.24.

EXAMPLE 129

N,N,α,α-Tetramethyl-3-phenylpyrazole-1-thioacetamide

Following the procedure of Example 127, but substituting N,N,α,α-tetramethyl-3-phenylpyrazole-1-acetamide for N,N,α,α,4-pentamethyl-3-phenylpyrazole-1-acetamide there was obtained N,N,α,α-tetramethyl-3-phenylpyrazole-1-thioacetamide having a melting point of 124°-127° C.

Analysis: Calc'd. for $C_{15}H_{19}N_3S$: C, 65.90; H, 7.00; N, 15.37; S, 11.73. Found: C, 65.70; H, 7.17; N, 15.45; S, 11.68.

EXAMPLE 130

N,N-Diethyl-α,4-dimethyl-3-phenylpyrazole-1-thioacetamide

Following the procedure of Example 127, but substituting N,N-diethyl-α,4-dimethyl-3-phenylpyrazole-1-acetamide for N,N,α,α,4-pentamethyl-3-phenylpyrazole-1-acetamide there was obtained N,N-diethyl-α,4-dimethyl-3-phenylpyrazole-1-thioacetamide having a melting point of 76°–79° C.

Analysis: Calc'd. for $C_{17}H_{23}N_3S$: C, 67.73; H, 7.69; N, 13.94; S, 10.64. Found: C, 67.54; H, 7.59; N, 14.16; S, 11.61.

EXAMPLE 131

α-Ethyl-N,N,4-trimethyl-3-phenylpyrazole-1-thioacetamide

Following the procedure of Example 127, but substituting α-ethyl-N,N,4-trimethyl-3-phenylpyrazole-1-acetamide for N,N,α,α,4-pentamethyl-3-phenylpyrazole-1-acetamide there was obtained α-ethyl-N,N,4-trimethyl-3-phenylpyrazole-1-thioacetamide having a melting point of 107°–110° C.

Analysis: Calc'd. for $C_{16}H_{21}N_3S$: C, 66.85; H, 7.37; N, 14.62; S, 11.15. Found: C, 66.76; H, 7.56; N, 14.70; S, 11.02.

EXAMPLE 132

4-Chloro-N,N,α-trimethyl-3-phenylpyrazole-1-thioacetamide

Following the procedure of Example 127, but substituting 4-chloro-N,N,α-trimethyl-3-phenylpyrazole-1-acetamide for N,N,α,α,4-pentamethyl-3-phenylpyrazole-1acetamide there was obtained 4-chloro-N,N,α-trimethyl-3-phenylpyrazole-1-thioacetamide having a melting point of 80°–83° C.

Analysis: Calc'd. for $C_{14}H_{16}ClN_3S$: C, 57.23; H, 5.47; N, 14.30; Cl, 12.07; S, 10.91. Found: C, 57.13; H, 5.60; N, 14.44; Cl, 12.14; S, 11.03.

EXAMPLE 133

N,N,α-Trimethyl-3-phenylpyrazole-1-thioacetamide

Following the procedure of Example 127, but substituting N,N,α-trimethyl-3-phenylpyrazole-1-acetamide for N,N,α,α,4-pentamethyl-3-phenylpyrazole-1-acetamide there was obtained N,N,α-trimethyl-3-phenylpyrazole-1-thioacetamide having a melting point of 56°–58° C.

Analysis: Calc'd. for $C_{14}H_{17}N_3S$: C, 64.83; H, 6.61; N, 16.21; S, 12.36. Found: C, 64.76; H, 6.72; N, 16.32; S. 12.50.

EXAMPLE 134

N,N,α,4-Tetramethyl-3-phenylpyrazole-1-thioacetamide

Following the procedure of Example 127, but substituting N,N,α,4-tetramethyl-3-phenylpyrazole-1-acetamide for N,N,α,α,4-pentamethyl-3-phenylpyrazole-1-acetamide there was obtained N,N,α,4-tetramethyl-3-phenylpyrazole-1-thioacetamide having a melting point of 87°–89° C.

Analysis: Calc'd. for $C_{15}H_{19}N_3S$: C, 65.90; H, 7.00; N, 15.38; S, 11.73. Found: C, 65.68; H, 7.10; N, 15.05; S. 11.93.

EXAMPLE 135

3-(o-Chlorophenyl)-N,N,α-trimethylpyrazole-1-thioacetamide

Following the procedure of Example 127, but substituting 3-(o-chlorophenyl)-N,N,α-trimethylpyrazole-1-acetamide for N,N,α,α,4-pentamethyl-3-phenylpyrazole-1-acetamide there was obtained 3-(o-chlorophenyl)-N,N,α-trimethylpyrazole-1-thioacetamide having a melting point of 68°–69.5° C.

Analysis: Calc'd. for $C_{14}H_{16}ClN_3S$: C, 57.23; H, 5.49; Cl, 12.07; N, 14.30; S, 10.91 Found: C, 57.27; H, 5.53; Cl, 12.00; N, 14.50; S. 11.09

EXAMPLE 136

N,α,4-Trimethyl-3-phenylpyrazole-1-thioacetamide

Following the procedure of Example 127, but substituting N,α,4-trimethyl-3-phenylpyrazole-1-acetamide for N,N,α,α,4-pentamethyl-3-phenylpyrazole-1-acetamide there was obtained N,α,4-trimethyl-3-phenylpyrazole-1-thioacetamide having a melting point of 97°–99° C.

Analysis: Calc'd. for $C_{14}H_{17}N_3S$: C, 64.83; H, 6.61; N, 16.20; S, 12.36. Found: C, 64.72; H, 6.74; N, 16.23; S. 12.64.

EXAMPLE 137

N,α,α,4-Tetramethyl-3-phenylpyrazole-1-thioacetamide

Following the procedure of Example 127, but substituting N,α,α,4-tetramethyl-3-phenylpyrazole-1-acetamide for N,N,α,α,4-pentamethyl-3-phenylpyrazole-1-acetamide there was obtained N,α,α,4-tetramethyl-3-phenylpyrazole-1-thioacetamide having a melting point of 75°–77° C.

Analysis: Calc'd. for $C_{15}H_{19}N_3S$: C, 65.90; H, 7.00; N, 15.37; S. 11.73. Found: C, 65.55; H, 7.02; N, 15.11; S, 11.64.

EXAMPLE 138

N,N,4-Trimethyl-3-phenylpyrazole-1-propionamide

Following the procedure of Example 1, but substituting 3-chloro-N,N-dimethylpropionamide for 2-chloro-N,N-dimethylpropionamide there was obtained N,N,4-trimethyl-3-phenylpyrazole-1-propionamide having a melting point of 60°–63° C.

Analysis: Calc'd. for $C_{15}H_{19}N_3O$: C, 70.00; H, 7.44; N, 16.33. Found: C, 70.01; H, 7.45; N, 16.52.

EXAMPLE 139

3-(o-Ethoxyphenyl)-N,N,α,4-tetramethylpyrazole-1-acetamide

Following the procedure of Example 1, but substituting 3-(o-ethoxyphenyl)pyrazole for 4-methyl-3-phenylpyrazole there was obtained 3-(o-ethoxyphenyl)-N,N,α,4-tetramethylpyrazole-1-acetamide having a melting point of 96°–97.5° C.

Analysis: Calc'd. $C_{17}H_{23}N_3O_2$: C, 67.75; H, 7.69; N, 13.94. Found: C, 67.74; H, 7.66; N, 13.71.

EXAMPLE 140

4-Iodo-N,N,α-trimethyl-3-phenylpyrazole-1-acetamide

Following the procedure of Example 1, but substituting 4-iodo-3-phenylpyrazole for 4-methyl-3-phenylpyrazole there was obtained 4-iodo-N,N,αtrimethyl-3- phenylpyrazole-1-acetamide having a melting point of 108°-111° C.

Analysis: Calc'd. for $C_{14}H_{16}IN_3O$: C, 45.54; H, 4.37; N, 11.38; I, 34.37. Found: C, 45.93; H, 4.92; N, 11.02; I, 34.51.

EXAMPLE 141

α-Ethyl-N,N,5-trimethyl-3-phenylpyrazole-1-acetamide

Following the procedure of Example 1, but substituting 3-methyl-5-phenylpyrazole for 4-methyl-3-phenylpyrazole and 2-bromo-N,N-dimethylbutyramide for 2-chloro-N,N-dimethylpropionamide there was obtained α-ethyl-N,N,5-trimethyl-3-phenylpyrazole-1-acetamide having a melting point of 117°-119.5° C.

Analysis: Calc'd. for $C_{16}H_{21}N_3O$: C, 70.82; H, 7,80; N, 15.49. Found: C, 70.61; H, 7.57; N, 15.64.

EXAMPLE 142

Following the procedure of Example 1, but substituting
3-(o-fluorophenyl)pyrazole,
3-(o-bromophenyl)pyrazole,
3-(o-trifluoromethylphenyl)pyrazole,
3-(o-trifluoromethylphenyl)-4-methylpyrazole, and
3-(o-ethylphenyl)pyrazole for 4-methyl-3-phenylpyrazole
there were obtained
N,N,α-trimethyl-3-(o-fluorophenyl)pyrazole-1-acetamide,
N,N,α-trimethyl-3-(o-bromophenyl)pyrazole-1-acetamide,
N,N,α-trimethyl-3-(o-trifluoromethylphenyl)pyrazole-1-acetamide,
N,N,α,4-tetramethyl-3-(o-trifluoromethylphenyl)-pyrazole-1-acetamide, and
3-(o-ethylphenyl)-N,N,α-trimethylpyrazole-1-acetamide.

EXAMPLE 143

N,N,α,4-Tetramethyl-5-nitro-3-phenylpyrazole-1-acetamide

Following the procedure of Example 1, but substituting 4-methyl-5-nitro-3-phenylpyrazole for 4-methyl-3-phenylpyrazole there is obtained the title compound having a melting point of 141°-143° C.

Analysis: Calc'd. for $C_{15}H_{18}N_4O_3$: C, 59.59; H, 6.00; N, 18.53. Found: C, 59.62; H, 6.02; H, 18.53.

EXAMPLE 144

3-(o-Chlorophenyl)-N,N,α,α,4-pentamethylpyrazole-1-acetamide

Following the procedure of Example 49, but substituting 3-(o-chlorophenyl)-4-methylpyrazole for 4-methyl-3-phenylpyrazole and dimethylamine for aqueous methylamine there was obtained 3-(o-chlorophenyl)-N,N,α,α,4-pentamethylpyrazole-1-acetamide having a melting point of 175°-176° C.

Analysis: Calc'd. for $C_{16}H_{20}ClN_3O$: C, 62.84; H, 6.59; Cl, 11.60; N, 13.74. Found: C, 62.90; H, 6.52; Cl, 11.66; N, 13.54.

EXAMPLE 145

N,N,α,α,5-Pentamethyl-3-phenylpyrazole-1-acetamide

Following the procedure of Example 49, but substituting 3-methyl-5-phenylpyrazole for 4-methyl-3-phenylpyrazole and aqueous dimethylamine for aqueous methylamine there was obtained N,N,α,α,5-pentamethyl-3-phenylpyrazole-1-acetamide having a melting point of 123°-125° C.

Analysis: Calc'd. for $C_{16}H_{21}N_3O$: C, 70.82; H, 7.80; N, 15.49. Found: C, 71.01; H, 7.76; N, 15.74.

EXAMPLE 146

4-Chloro-α-ethyl-N,N-dimethyl-3-(o-tolyl)pyrazole-1-acetamide

Following the procedure of Example 108, but substituting α-ethyl-N,N-dimethyl-3-(o-tolyl)pyrazole-1-acetamide for N,N,α,5-tetramethyl-3-phenylpyrazole-1-acetamide and tertbutyl hypochlorite for bromine there was obtained 4-chloro-α-ethyl-N,N-dimethyl-3-(o-tolyl)pyrazole-1-acetamide having a melting point of 49.5°-52° C.

Analysis: Calc'd. for $C_{16}H_{20}ClN_3O$: C, 62.84; H, 6.59; Cl, 11.59; N, 13.74. Found: C, 62.90; H, 6.64; Cl, 11.82; N, 13.88.

EXAMPLE 147

5-Chloro-N,N,α,α,4-pentamethyl-3-phenylpyrazole-1-acetamide

Following the procedure of Example 108, but substituting N,N,α,α,4-pentamethyl-3-phenylpyrazole-1-acetamide for N,N,α,5-tetramethyl-3-phenylpyrazole-1-acetamide and tertbutyl hypochlorite for bromine there was obtained 5-chloro-N,N,α,α,4-pentamethyl-3-phenylpyrazole-1-acetamide having a melting point of 96°-99° C.

Analysis: Calc'd. for $C_{16}H_{20}ClN_3O$: C, 62.84; H, 6.59; Cl, 11.59; N, 13.74. Found C, 63.00; H, 6.64; Cl, 11.74; N, 13.98.

EXAMPLE 148

4-Fluoro-N,N,α,α,-tetramethyl-3-phenylpyrazole-1-acetamide

Following the procedure of Example 108, but substituting N,N,α,α,-tetramethyl-3-phenylpyrazole-1-acetamide for N,N,α,5-tetramethyl-3-phenylpyrazole-1-acetamide, trifluoromethyl hypofluorite for bromine, and carbon tetrachloride for acetic acid as the reaction solvent there was obtained 4-fluoro-N,N,α,α-tetramethyl-3-phenylpyrazole-1-acetamide.

EXAMPLE 149

α-Bromo-N,N-dimethyl-3-phenylpyrazole-1-propionamide

Following the procedure of Example 121, but substituting 2,3-dibromo-N,N-dimethylpropionamide for 2-bromo-N,N,2-trimethylpropionamide there was obtained α-bromo-N,N-dimethyl-3-phenylpyrazole-1-propionamide having a melting point of 93°-94° C.

Analysis: Calc'd. for $C_{14}H_{16}BrN_3O$: C, 52.18; H, 5.01; Br, 24.80; N, 13.04. Found C, 52.34; H, 5.10; Br, 24.59; N, 13.20.

EXAMPLE 150

Hydrochloride salt of N,N,α,4-tetramethyl-3-phenylpyrazole-1-acetamide

Hydrogen chloride was passed into a stirred solution of N,N,α,4-tetramethyl-3-phenylpyrazole-1-acetamide (2.53 g., 0.01 mole) in carbon tetrachloride (50 ml.). The precipitated salt was filtered off and was recrystallized from ethyl acetate; m.p. 170°-172° C.

EXAMPLE 151 p-Toluenesulfonate salt of
N,N,α,4-tetramethyl-3-phenylpyrazole-1-acetamide

A solution of p-toluenesulfonic acid (1.9 g., 0.01 mole) in chloroform was added to a solution of N,N,α,4-tetramethyl-3-phenylpyrazole-1-acetamide (2.5 g., 0.01 mole) in chloroform. Evaporation of the chloroform gave the p-toluenesulfonate salt of N,N,α,4-tetramethyl-3-phenylpyrazole having a melting point of 131°–134° C.

EXAMPLE 152

A dispersible powder concentrate having the following percentage composition:

| | |
|---|---|
| N,N,α,4-tetramethyl-3-phenyl-pyrazole-1-acetamide | 45.8% |
| Polymerized sodium salt of substituted benzoid long-chain sulfonic acid (Daxad 27) | 9.2% |
| Kaolinite | 45.0% | was prepared by mixing 250 g. of N,N,α,4-tetramethyl-3-phenylpyrazole-1-acetamide, 50 g. of a polymerized sodium salt of substituted benzoid long-chain sulfonic acid (Daxad 27), and 245 g. of kaolinite. The mixture was milled to a particle size averaging 5 to 30 microns. It was suspended in 10 gals. of water, giving an aqueous spray containing about 6500 parts per million of active ingredient.

EXAMPLE 153

A fine granular formulation having the following percentage composition:

| | |
|---|---|
| N,N,α,4-tetramethyl-3-phenyl-pyrazole-1-acetamide | 3.7% |
| Vermiculite (30/60 mesh) | 96.3% | was prepared by spraying a solution of 220 g. of N,N,α,4-tetramethyl-3-phenylpyrazole-1-acetamide in 1000 ml. of chloroform onto 5780 g. of vermiculite (30 to 60 mesh) while the vermiculite was being tumbled and stirred so as to assure even distribution. The chloroform was then evaporated, leaving the active compound adsorbed on the vermiculite, and the vermiculite was pulverized.

EXAMPLE 154

An emulsifiable concentrate having the following percentage composition:

| | |
|---|---|
| N,N,α,4-tetramethyl-3-phenyl-pyrazole-1-acetamide | 15.0% |
| Technical alkyl naphthalene boiling at 238° to 293° C. (Velsicol AR50) | 19.7% |
| Xylene | 17.4% |
| Acetone | 17.4% |
| Ethylene dichloride | 25.4% |
| Blend of alkyl aryl sulfonates and alkylphenoxy polyethoxy ethanols (Triton X-151) | 5.1% | was prepared by mixing 15.0 lbs. of N,N,α,4-tetramethyl-3-phenylpyrazole-1-acetamide, 19.7 lbs. of Velsicol AR50, 17.4 lbs. of xylene, 17.4 lbs. of acetone, 25.4 lbs. of ethylene dichloride, and 5.1 lbs. of Triton X-151. 6.67 Lbs. of the concentrate mixed with 10 gals. of water gave a spray emulsion containing about 11,000 ppm of active ingredient.

EXAMPLE 155

An emulsifiable concentrate having the following percentage composition:

| | |
|---|---|
| N,N,α,4-tetramethyl-3-phenyl-pyrazole-1-acetamide | 40.0% |
| Technical alkyl naphthalene boiling at 238° to 293° C. (Velsicol AR50) | 13.7% |
| Xylene | 12.3% |
| Acetone | 11.3% |
| Ethylene dichloride | 17.7% |
| Blend of alkyl aryl sulfonates and alkylphenoxy polyethoxy ethanols (Triton X-151) | 5.0% | was prepared by mixing 40.0 lbs. of N,N,α,4-tetramethyl-3-phenylpyrazole-1-acetamide, 13.7 lbs. of Velsicol AR50, 12.3 lbs. of xylene, 11.3 lbs. of acetone, 17.7 lbs. of ethylene dichloride, and 5.0 lbs. of Triton X-151. 1.67 Lbs. of the concentrate mixed with 10 gals. of water gave a spray emulsion containing about 8,000 ppm of active ingredient.

EXAMPLE 156

A dispersible powder concentrate having the following percentage composition:

| | |
|---|---|
| N,N,α,4-tetramethyl-3-phenyl-pyrazole-1-acetamide | 50% |
| Kaolinite Clay (finely divided) | 46% |
| Sodium salt of condensed mono-naphthalene sulfonic acid (Lomar D) | 4% | was prepared by mixing 50 g. of N,N,α,4-tetramethyl-3-phenylpyrazole-1-acetamide, 46 g. of the kaolinite clay, and 4 g. of Lomar D. The mixture was milled to an average particle size of 5 to 30 microns.

EXAMPLE 157

A granular formulation having the following percentages composition:

| | |
|---|---|
| N,N,α,4-tetramethyl-3-phenyl-pyrazole-1-acetamide | 1% |
| Pyrophyllite (30/60 mesh) | 99% | was prepared by dissolving 1.0 lb. of the N,N,α,4-tetramethyl-3-phenylpyrazole-1-acetamide, in 10.0 l. of ethylene dichloride and spraying the solution on 99.0 lbs. of pyrophyllite. The granules were dried and then packaged for use.

EXAMPLE 158

An emulsifiable concentrate having the following percentage composition:

| | |
|---|---|
| N,N,α,4-tetramethyl-3-phenyl-pyrazole-1-acetamide | 25% |
| Tridecylsulfonic acid | 25% |
| Xylene | 50% | was prepared by mixing 250 g. of N,N,α,4-tetramethyl-3-phenylpyrazole-1-acetamide, 250 g. of tridecylsulfonic acid, and 500 g. of xylene. The emulsifiable concentrate containing the tridecylsulfonate salt of N,N,α,4-tetramethyl-3-phenylpyrazole-1-acetamide was mixed with 10 gals. of water to give a spray emulsion containing about 6500 ppm of active ingredient.

EXAMPLE 159

Following the procedure of the preceding Examples 152 through 157, inclusive, compositions are similarly prepared substituting each of the compounds prepared in Example 2 through 151, inclusive, for the N,N,α,4-tetramethyl-3-penylpyrazole-1-acetamide.

EXAMPLE 160

N,N,α,α-Tetramethyl-3,4-diphenylpyrazole-1-acetamide

Following the procedure of Example 95, but substituting N,N,α-trimethyl-3,4-diphenylpyrazole-1-acetamide for N,N,α,4-tetramethyl-3-phenylpyrazole-1-acetamide and methyl iodide for ethyl iodide, there was obtained N,N,α,α-tetramethyl-3,4-diphenylpyrazole-1-acetamide, having a melting point of 148°–150° C.

Analysis: Calc'd. for $C_{21}H_{23}N_3O$: C, 75.64; H, 6.95; N, 12.60. Found: C, 75.57; H, 6.91; N, 12.68.

EXAMPLE 161

3-Chloro-N,N,α,α,4-pentamethyl-5-phenylpyrazole-1-acetamide

Following the procedure of Example 108, but substituting N,N,α,α,4-pentamethyl-5-phenylpyrazole-1-acetamide for N,N,α,5-tetramethyl-3-phenylpyrazole-1-acetamide, tert-butyl hypochlorite for bromine, and carbon tetrachloride for acetic acid as the reaction solvent, there was obtained 3-chloro-N,N,α,α,4-pentamethyl-5-phenylpyrazole-1-acetamide, having a melting point of 134.5°–136° C.

Analysis: Calc'd. for $C_{16}H_{20}ClN_3O$: C, 62.84; H, 6.59; Cl, 11.59; N, 13.74. Found: C, 63.11; H, 6.89; Cl, 11.58; N, 13.66.

EXAMPLE 162

N,N-Dimethyl-1-(4-methyl-3-phenylpyrazol-1-yl)-cyclopentanecarboxamide

Following the procedure of Example 95, but substituting α-(4-bromobutyl)-N,N,4-trimethyl-3-phenylpyrazole-1-acetamide (Example 43) for N,N,α,4-tetramethyl-3-phenylpyrazole-1-acetamide and without addition of ethyl iodide there is obtained N,N-dimethyl-1-(4-methyl-3-phenylpyrazol-1-yl)cyclopentanecarboxamide, m.p. 99°–101° C.

Analysis: Calc'd. for $C_{18}H_{23}N_3O$: C, 72.69; H, 7.80; N, 14.13. Found: C, 72,67; H, 7.65; N, 14.21.

EXAMPLE 163

α-Ethyl-N,N,4,5-tetramethyl-3-phenylpyrazole-1-acetamide

Using the procedure of Example 1, but substituting 2-bromo-N,N-dimethylbutyramide for 2-chloro-N,N-dimethylpropionamide and 4,5-dimethyl-3-phenylpyrazole for 4-methyl-3-phenylpyrazole there was obtained α-ethyl-N,N,4,5-tetramethyl-3-phenylpyrazole-1-acetamide, m.p. 119°–121° C.

Analysis: Calc'd. for $C_{17}H_{23}N_3O$: C, 71.55; H, 8.12; N, 14.72. Found: C, 71.49; H, 8.11; N, 14.62.

EXAMPLE 164

α,4-Diethyl-N,N-dimethyl-3-phenylpyrazole-1-acetamide

Using the procedure of Example 1, but substituting 2-bromo-N,N-dimethylbutyramide for 2-chloro-N,N-dimethylpropionamide and 4-ethyl-3-phenylpyrazole for 4-methyl-3-phenylpyrazole, there was obtained α,4-diethyl-N,N-dimethyl-3-phenylpyrazole-1-acetamide, m.p. 77.5°–79° C.

Analysis: Calc'd. for $C_{17}H_{23}N_3O$: C, 71.54; H, 8.12; N, 14.73. Found: C, 71.53; H, 8.03; N, 14.78.

EXAMPLE 165

(o-Chlorophenyl)-4-ethyl-N,N,α-trimethylpyrazole-1-acetamide

Using the procedure of Example 1, but substituting 3-(o-chlorophenyl)-4-ethylpyrazole for 4-methyl-3-phenylpyrazole, there was obtained 3-(o-chlorophenyl)-4-ethyl-N,N,α-trimethylpyrazole-1-acetamide, m.p. 74°–76° C.

Analysis: Calc'd. for $C_{16}H_{20}ClN_3O$: C, 62.84; H, 6.54; Cl, 11.60; N, 13.74. Found: C, 62.71; H, 6.67; Cl, 11.63; N, 13.86.

EXAMPLE 166

3-(o-Chlorophenyl-α,4-diethyl-N,N-dimethylpyrazole-1-acetamide

Using the procedure for Example 1, but substituting 2-bromo-N,N-dimethylbutyramide for 2-chloro-N,N-dimethylpropionamide and 3-(o-chlorophenyl)-4-ethylpyrazole for 4-methyl-3-phenylpyrazole, there was obtained 3-(o-chlorophenyl)-α,4-diethyl-N,N-dimethylpyrazole-1-acetamide, m.p. 60°–63° C.

Analysis: Calc'd. for $C_{17}H_{22}ClN_3O$: C, 63.84; H, 6.93; Cl, 11.09; N, 13.14. Found: C, 64.10; H, 7.06; Cl, 11.63; N, 13.21.

EXAMPLE 167

α-Ethyl-3-(o-fluorophenyl)-N,N,4-trimethylpyrazole-1-acetamide

Using the procedure of Example 1, but substituting 2-bromo-N,N-dimethylbutyramide for 2-chloro-N,N-dimethylpropionamide and 3-(o-fluorophenyl)-4-methylpyrazole for 4-methyl-3-phenylpyrazole, there was obtained α-ethyl-3-(o-fluorophenyl)-N,N,4-trimethylpyrazole-1-acetamide, b.p. 171°–173° C./0.15 mm.

Analysis: Calc'd. for $C_{16}H_{20}FN_3O$: C, 66.41; H, 6.97; F, 6.57; N, 14.52. Found: C, 65.73; H, 7.04; F, 6.52; N, 14.42.

EXAMPLE 168

3-(o-Fluorophenyl)-N,N,α,4-tetramethylpyrazole-1-acetamide

Following the procedure of Example 1, but substituting 3-(o-fluorophenyl)-4-methylpyrazole for 4-methyl-3-phenylpyrazole, there was obtained 3-(o-fluorophenyl)-N,N,α,4-tetramethylpyrazole-1-acetamide, having a boiling points of 154°–156° C./0.07 mm.

Analysis: Calc'd. for $C_{15}H_{18}FN_3O$: C, 65.44; H, 6.59; F, 6.90; N, 15.26. Found: C, 65.29; H, 6.58; F, 7.09; N, 15.13.

EXAMPLE 169

3-(o-Bromophenyl)-N,N-diethyl-α,4-dimethylpyrazole-1-acetamide

Using the procedure of Example 1, but substituting 2-chloro-N,N-diethylpropionamide for 2-chloro-N,N-dimethylpropionamide and 3-(o-bromophenyl)-4-methylpyrazole for 4-methyl-3-phenylpyrazole, there is obtained 3-(o-bromophenyl)-N,N-diethyl-α,4-dimethylpyrazole-1-acetamide, b.p. 187°–190° C./0.15 mm.

Analysis: Calc'd. for $C_{17}H_{22}BrN_3O$: C, 56.05; H, 6.09; Br, 21.94; N, 11.53. Found: C, 56.42; H, 6.45; Br, 21.85; N, 11.57.

EXAMPLE 170

3-(o-Bromophenyl)-α-ethyl-N,N,4-trimethylpyrazole-1-acetamide

Using the procedure of Example 1, but substituting 2-bromo-N,N-dimethylbutyramide for 2-chloro-N,N-dimethylpropionamide and 3-(o-bromophenyl)-4-methylpyrazole for 4-methyl-3-phenylpyrazole, there was obtained 3-(o-bromophenyl)-α-ethyl-N,N,4-trimethylpyrazole-1acetamide, b.p. 188°–190° C./0.12 mm.

Analysis: Calc'd. for $C_{16}H_{20}BrN_3O$: C, 54.86; H, 5.76; Br, 22.82; N, 12.00. Found: C, 54.73; H, 6.06; Br, 22.63; N, 12.20.

EXAMPLE 171

α-Ethyl-N,N-dimethyl-3-phenyl-4-isopropylpyrazole-1-acetamide

Using the procedure of Example 1, but substituting 2-bromo-N,N-dimethylbutyramide for 2-chloro-N,N-dimethylpropionamide and 3-phenyl-4-isopropylpyrazole for 4-methyl-3-phenylpyrazole, there was obtained α-ethyl-N,N-dimethyl-3-phenyl-4-isopropylpyrazole-1-acetamide, m.p. 89°–90° C.

Analysis: Calc'd. for $C_{18}H_{25}N_3O$: C, 72.20; H, 8.42; N, 14.04. Found: C, 72.21; H, 8.42; N, 14.24.

EXAMPLE 172

N,N,α-Trimethyl-3-phenyl-4-isopropylpyrazole-1-acetamide

Following the procedure of Example 1, but substituting 3-phenyl-4-isopropylpyrazole for 4-methyl-3-phenylpyrazole, there was obtained N,Nα-trimethyl-3-phenyl-4-isopropylpyrazole-1-acetamide, m.p. 102°–105° C.

Analysis: Calc'd. for $C_{17}H_{23}N_3O$: C, 71.54; H, 8.12; N, 14.73. Found: C, 71.61; H, 8.33; N, 14.76.

EXAMPLE 173

N,Nα-Trimethyl-3-phenyl-4-propylpyrazole-1-acetamide

Following the procedure of Example 1, but substituting 3-phenyl-4-propylpyrazole for 4-methyl-3-phenylpyrazole, there was obtained N,Nα-trimethyl-3-phenyl-4-propylpyrazole-1-acetamide, m.p. 82.5°–85° C.

Analysis: Calc'd. for $C_{17}H_{23}N_3O$: C, 71.54; H, 8.12; N, 14.73. Found: C, 71.56; H, 8.16; N, 14.85.

EXAMPLE 174

α-Ethyl-N,N-dimethyl-3-phenyl-4-isopylpyrazole-1-acetamide

Using the procedure of Example 1, but substituting 2-bromo-N,N-dimethylbutyramide for 2-chloro-N,N-dimethylpropionamide and 3-phenyl-4-propylpyrazole for 4-methyl-3-phenylpyrazole, there was obtained α-ethyl-N,N-dimethyl-3-phenyl-4-propylpyrazole-1-acetamide, m.p. 63°–65.5° C.

Analysis: Calc'd. for $C_{15}H_{18}N_3O$: C, 72.20; H, 8.42; N, 14.04. Found: C, 72.33; H, 8.42; N, 14.03.

EXAMPLE 175

3-(2,4-Dichlorophenyl)-N,N,α,4-tetramethylpyrazole-1-acetamide

Following the procedure of Example 1, but substituting 3-(2,4-dichlorophenyl)-4-methylpyrazole for 4-methyl-3-phenylpyrazole, there was obtained 3-(2,4-dichlorophenyl)-N,N,α,4-tetramethylpyrazole-1-acetamide, b.p. 170° C./0.1 mm.

Analysis: Calc'd. for $C_{15}H_{17}Cl_2N_3O$: C, 55.22; H, 5.25; Cl, 21.74; N, 12.88. Found: C, 54.84; H, 5.38; Cl, 21.88; N, 12.71.

EXAMPLE 176

3-(2,5-Dichlorophenyl)-N,N,α,4-tetramethylpyrazole-1-acetamide

Following the procedure of Example 1, but substituting 3-(2,5-dichlorophenyl)-4-methylpyrazole for 4-methyl-3-phenylpyrazole, there was obtained 3-(2,5-dichlorophenyl)-N,N,α,4-tetramethylpyrazole-1-acetamide, b.p. 170° C./0.1 mm.

Analysis: Calc'd. for $C_{15}H_{17}Cl_2N_3O$: C, 55.22; H, 5.25; Cl, 21.74; N, 12.88. Found: C, 55.08; H, 5.05; Cl, 22.37; N, 12.64.

EXAMPLE 177

3-(3,4-Dichlorophenyl)-N,N,α,4-tetramethylpyrazole-1-acetamide

Following the procedure of Example 1, but substituting 3-(3,4-dichlorophenyl)-4-methylpyrazole for 4-methyl-3-phenylpyrazole, there was obtained 3-(3,4-dichlorophenyl)-N,N,α,4-tetramethylpyrazole-1-acetamide, m.p. 109°–110° C.

Analysis: Calc'd. for $C_{15}H_{17}Cl_2N_3O$: C, 55.22; H, 5.25; Cl, 21.74; N, 12.88. Found: C, 55.39; H, 5.31; Cl, 21.80; N, 13.17.

EXAMPLE 178

N,N,α,α,4,5-Hexamethyl-3-phenylpyrazole-1-acetamide

Following the procedure of Example 95, but substituting N,N,α,4,5-pentamethyl-3-phenylpyrazole-1-acetamide for N,N,α,4-tetramethyl-3-phenylpyrazole-1-acetamide and methyl iodide for ethyl iodide, there was obtained N,N,α,α,4,5-hexamethyl-3-phenylpyrazole-1-acetamide, m.p. 115°–117° C.

Analysis: Calc'd. for $C_{17}H_{23}N_3O$: C, 71.54; H, 8.12; N, 14.73. Found: C, 70.77; H, 8.05; N, 14.43.

EXAMPLE 179

4-Ethyl-N,N,α,α,-tetramethyl-3-phenylpyrazole-1-acetamide

Following the procedure of Example 95, but substituting 4-ethyl-N,N,α-trimethyl-3-phenylpyrazole-1-acetamide for N,N,α,4-tetramethyl-3-phenylpyrazole-1-acetamide and methyl iodide for ethyl iodide, there was obtained 4-ethyl-N,N,α,α-tetramethyl-3-phenylpyrazole-1-acetamide, m.p. 108.5°–111° C.

Analysis: Calc'd. for $C_{17}H_{23}N_3O$: C, 71.54; H, 8.12; N, 14.73. Found: C, 71.31; H, 7.96; N, 14.69.

EXAMPLE 180

3-(o-Chlorophenyl)-N,N,α,α,5-pentamethylpyrazole-1-acetamide

Following the procedure of Example 95, but substituting 3-(o-Chlorophenyl)-N,N,α,5-tetramethylpyrazole-1-acetamide for N,N,α,4-tetramethyl-3-phenylpyrazole-1-acetamide and methyl iodide for ethyl iodide, there was obtained 3-(o-chlorophenyl)-N,N,α,α,5-pentamethylpyrazole-1-acetamide, m.p. 104°–106° C.

Analysis: Calc'd. for $C_{16}H_{20}ClN_3O$: C, 62.84; H, 6.59; N, 13.74; Cl, 11.60. Found: C, 63.06; H, 6.63; N, 14.04; Cl, 11.80.

EXAMPLE 181

3-(o-Chlorophenyl)-4-ethyl-N,N,α,α-tetramethylpyrazole-1-acetamide

Following the procedure of Example 95, but substituting 3-(o-Chlorophenyl)-4-ethyl-N,N,α-trimethylpyrazole-1-acetamide for N,N,α,4-tetramethyl-3-phenylpyrazole-1-acetamide and methyl iodide for ethyl iodide, there was obtained 3-(o-chlorophenyl)-4-ethyl-N,N,α,α-tetramethylpyrazole-1-acetamide, m.p. 101.5°–104.5° C.

Analysis: Calc'd. for $C_{17}H_{22}ClN_3O$: C, 63.84; H, 6.93; Cl, 11.09; N, 13.14. Found: C, 63.83; H, 7.03; Cl, 10.92; N, 13.01.

EXAMPLE 182

3-(m-Chlorophenyl)-N,N,α,α,4-pentamethylpyrazole-1-acetamide

Following the procedure of Example 95, but substituting 3-(m-chlorophenyl)-N,N,α,4-tetramethylpyrazole-1-acetamide for N,N,α,4-tetramethyl-3-phenylpyrazole-1-acetamide and methyl iodide for ethyl iodide, there was obtained 3-(m-chlorophenyl)-N,N,α,α,4-pentamethylpyrazole-1-acetamide, m.p. 144°–146.5° C.

Analysis: Calc'd. for $C_{16}H_{20}ClN_3O$: C, 62.84; H, 6.59; Cl, 11.60; N, 13.74. Found: C, 62.94; H, 6.54; Cl, 11.71; N, 13.87.

EXAMPLE 183

3-(p-Chlorophenyl)-N,N,α,α,4-pentamethylpyrazole-1-acetamide

Following the procedure of Example 95, but substituting 3-(p-Chlorophenyl)-N,N,α,4-tetramethylpyrazole-1-acetamide for N,N,α,4-tetramethyl-3-phenylpyrazole-1-acetamide and methyl iodide for ethyl iodide, there was obtained 3-(p-Chlorophenyl)-N,N,α,α,4-pentamethylpyrazole-1-acetamide, m.p. 121.5°–123.5° C.

Analysis: Calc'd. for $C_{16}H_{20}ClN_3O$: C, 62.84; H, 6.59; Cl, 11.60; N, 13.74. Found: C, 62.62; H, 6.57; Cl, 11.62; N, 13.76.

EXAMPLE 184

4-Bromo-N,N,α,α-tetramethyl-3-phenylpyrazole-1-acetamide

Following the procedure of Example 95, but substituting 4-bromo-N,N,α-trimethyl-3-phenylpyrazole-1-acetamide for N,N,α,4-tetramethyl-3-phenylpyrazole-1-acetamide and methyl iodide for ethyl iodide, there was obtained 4-bromo-N,N,α,α-tetramethyl-3-phenylpyrazole-1-acetamide, m.p. 122.5°–124° C.

Analysis: Calc'd. for $C_{15}H_{18}BrN_3O$: C, 53.58; H, 5.39; Br, 23.77; N, 12.50.
Found: C, 53.79; H, 5.45; Br, 23.54; N, 12.51.

EXAMPLE 185

3-(o-Bromophenyl)-N,N,α,α,4-pentamethylpyrazole-1-acetamide

Following the procedure of Example 95, but substituting 3-(o-bromophenyl)-N,N,α,4-tetramethylpyrazole-1-acetamide for N,N,α,4-tetramethyl-3-phenylpyrazole-1-acetamide and methyl iodide for ethyl iodide, there was obtained 3-(o-bromophenyl)-N,N,α,α,4-pentamethylpyrazole-1-acetamide, m.p. 191.5°–194° C.

Analysis: Calc'd. for $C_{16}H_{20}BrN_3O$: C, 54.86; H, 5.76; Br, 22.82; N, 12.00. Found: C, 55.14; H, 5.86; Br, 22.74; N, 12.05.

EXAMPLE 186

4-Cyano-N,N,α,α-tetramethyl-3-phenylpyrazole-1-acetamide

Following the procedure of Example 95, but substituting 4-cyano-N,N,α-trimethyl-3-phenylpyrazole-1-acetamide for N,N,α,4-tetramethyl-3-phenylpyrazole-1-acetamide and methyl iodide for ethyl iodide, there was obtained 4-cyano-N,N,α,α-tetramethyl-3-phenylpyrazole-1-acetamide, m.p. 116.5°–119° C.

Analysis: Calc'd. for $C_{16}H_{18}N_4O$: C, 68.08; H, 6.43; N, 19.85. Found: C, 67.84; H, 6.44; N, 20.01.

EXAMPLE 187

3-(o-Methoxyphenyl)-N,N,α,α-tetramethylpyrazole-1-acetamide

Following the procedure of Example 95, but substituting 3-(o-methoxyphenyl)-N,N,α-trimethylpyrazole-1-acetamide for N,N,α,4-tetramethyl-3-phenylpyrazole-1-acetamide and methyl iodide for ethyl iodide, there was obtained 3-(o-methoxyphenyl)-N,N,α,α-tetramethylpyrazole-1-acetamide, b.p. 174°–176° C./0.04 mm.

Analysis: Calc'd. for $C_{16}H_{21}N_3O_2$: C, 66.87; H, 7.37; N, 14.63. Found: C, 66.87; H, 7.45; N, 14.36.

EXAMPLE 188

3-(2,5-Dichlorophenyl)-N,N,α,α-tetramethylpyrazole-1-acetamide

Following the procedure of Example 95, but substituting 3-(2,5-dichlorophenyl)-N,N,α-trimethylpyrazole-1-acetamide for N,N,α,4-tetramethyl-3-phenylpyrazole-1-acetamide and methyl iodide for ethyl iodide, there was obtained 3-(2,5-dichlorophenyl)-N,N,α,α-tetramethylpyrazole-1-acetamide, m.p. 94°–96° C.

Analysis: Calc'd. for $C_{15}H_{17}Cl_2N_3O$: C, 55.22; H, 5.25; Cl, 21.74; N, 12.88. Found: C, 55.08; H, 5.30; Cl, 21.80; N, 12.83.

EXAMPLE 189

N,N,α,α-tetramethyl-3-phenyl-4-isopropylpyrazole-1-acetamide

Following the procedure of Example 95, but substituting N,N,α-trimethyl-3-phenyl-4-isopropylpyrazole-1-acetamide for N,N,α,4-tetramethyl-3-phenylpyrazole-1-acetamide and methyl iodide for ethyl iodide, there was obtained N,N,α,α-tetramethyl-3-phenyl-4-isopropylpyrazole-1-acetamide, m.p. 80.5°–82.5° C.

EXAMPLE 190

N,N,α,α-tetramethyl-3-phenyl-4-propylpyrazole-1-acetamide

Following the procedure of Example 95, but substituting N,N,α-trimethyl-3-phenyl-4-propylpyrazole-1-acetamide for N,N,α,4-tetramethyl-3-phenypyrazole-1-acetamide and methyl iodide for ethyl iodide, there was obtained N,N,α,α-tetramethyl-3-phenyl-4-propylpyrazole-1-acetamide, m.p. 98.5°–101° C.

Analysis: Calc'd. for $C_{18}H_{25}N_3O$: C, 72.20; H, 8.42; N, 14.04. Found: C, 72.23; H, 8.37; N, 14.03.

EXAMPLE 191

3-(2,4-Dichlorophenyl)-N,N,α,α,4-pentamethylpyrazole-1-acetamide

Following the procedure of Example 95, but substituting 3-(2,4-dichlorophenyl)-N,N,α,4-phenylpyrazole-1-acetamide for N,N,α,4-tetramethyl-3-phenylpyrazole-1-acetamide and methyl iodide for ethyl iodide, there was obtained 3-(2,4-dichlorophenyl)-N,N,α,α,4-pentamethylpyrazole-1-acetamide, m.p. 110°–111° C.

Analysis: Calc'd. for $C_{16}H_{19}Cl_2N_3O$: C, 56.60; H, 5.64; Cl, 20.89; N, 12.38. Found: C, 56.49; H, 5.74; Cl, 21.08; N, 12.41.

EXAMPLE 192

3-(3,4-Dichlorophenyl)-N,N,α,α,4-pentamethylpyrazole-1-acetamide

Following the procedure of Example 95, but substituting 3-(3,4-dichlorophenyl)-N,N,α,4-tetramethyl-pyrazole-1-acetamide for N,N,α,4-tetramethyl-3-phenylpyrazole-1-acetamide for N,N,α,4-tetramethyl-3-phenylpyrazole-1-acetamide and methyl iodide for ethyl iodide, there was obtained 3-(3,4-dichlorophenyl)-N,N,α,α,4-pentamethylpyrazole-1-acetamide, m.p. 141.5°–142.5° C.

Analysis: Calc'd. for $C_{16}H_{19}Cl_2N_3O$: C, 56.60; H, 5.64; Cl, 20.89; N, 12.38. Found: C, 56.44; H, 5.74; Cl, 20.93; N, 12.40.

EXAMPLE 193

3-(2,5-Dichlorophenyl)-N,N,α,α,4-pentamethylpyrazole-1-acetamide

Following the procedure of Example 95, but substituting 3-(2,5-dichlorophenyl)-N,N,α,4-tetramethyl-pyrazole-1-acetamide for N,N,α,4-tetramethyl-3-phenylpyrazole-1-acetamide and methyl iodide for ethyl iodide, there was obtained 3-(2,5-dichlorophenyl)-N,N,α,α,4-pentamethylpyrazole-1-acetamide, m.p. 129.5°–130.5° C.

Analysis: Calc'd. for $C_{16}H_{19}Cl_2N_3O$: C, 56.60; H, 5.64; Cl, 20.89; N, 12.38. Found: C, 56.86; H, 5.57; Cl, 20.20; N, 12.36.

EXAMPLE 194

3-(o-Cyanophenyl)-N,N,α,α,4-pentamethylpyrazole-1-acetamide

Following the procedure of Example 95, but substituting 3-(o-cyanophenyl)-N,N,α,4-tetramethyl-pyrazole-1-acetamide for N,N,α,4-tetramethyl-3-phenylpyrazole-1-acetamide and methyl iodide for ethyl iodide, there was obtained 3-(o-cyanophenyl)-N,N,α,α,4-pentamethylpyrazole-1-acetamide, m.p. 124.5°–126° C.

Analysis: Calc'd. for $C_{17}H_{20}N_4O$: C, 68.89; H, 6.80; N, 18.91. Found: C, 69.06; H, 7.16; N, 18.91.

EXAMPLE 195

3-(o-Bromophenyl)-N,N,α,4-tetramethylpyrazole-1-acetamide

Following the procedure of Example 68, but substituting 3-(o-bromophenyl)-α,4-dimethylpyrazole-1-acetic acid for α,4-dimethyl-3-phenylpyrazole-1-acetic acid, and dimethyl amine for aqueous ammonia, there was obtained 3-(o-bromophenyl)-N,N,α,4-tetramethyl-pyrazole-1-acetamide, m.p. 101.5°–104° C.

Analysis: Calc'd. for $C_{15}H_{18}BrN_3O$: C, 53.58; H, 5.39; Br, 23.77; N, 12.50. Found: C, 53.65; H, 5.47; Br, 23.79; N, 12.31.

EXAMPLE 196

3-(o-Fluorophenyl)-N,N,α,α,4-pentamethylpyrazole-1-acetamide

Following the procedure of Example 68, but substituting 3-(o-fluorophenyl)-α,α,4-trimethylpyrazole-1-acetic acid for α,4-dimethyl-3-phenylpyrazole-1-acetic acid, and dimethylamine for aqueous ammonia, there was obtained 3-(o-fluorophenyl)-N,N,α,α,4-pentamethylpyrazole-1-acetamide, m.p. 112.5°–114° C.

Analysis: Calc'd. for $C_{16}H_{20}FN_3O$: C, 66.41; H, 6.97; F, 6.57; N, 14.52. Found: C, 66.52; H, 6.92; F, 6.58; N, 14.64.

EXAMPLE 197

3-(o-Chlorophenyl)-N,N,α,α,4-pentamethylpyrazole-1-thioacetamide

Following the procedure of Example 127, but substituting 3-(o-chlorophenyl)-N,N,α,α,4-pentamethylpyrazole-1-acetamide for N,N,α,α,4-pentamethyl-3-phenylpyrazole-1-acetamide, there was obtained 3-(o-chlorophenyl)-N,N,α, α,4-pentamethylpyrazole-1-thioacetamide, m.p. 146.5°–148° C.

Analysis: Calc'd. for $C_{16}H_{20}ClN_2S$: C, 59.70; H, 6.26; Cl, 11.01; N, 13.05; S, 9.99. Found: C, 59.68; H, 6.16; Cl, 11.31; N, 13.03; S, 10.11.

EXAMPLE 198

4-Chloro-3-(o-chlorophenyl)-N,N,α,α-tetramethylpyrazole-1-acetamide

Following the procedure of Example 108, but substituting 3-(o-chlorophenyl)-N,N,α,α-tetramethyl-pyrazole-1-acetamide for N,N,α,5-tetramethyl-3-phenylpyrazole-1-acetamide, tertbutyl hypochlorite for bromine, and carbon tetrachloride for acetic acid as the reaction solvent, there was obtained 4-chloro-3-(o-chlorophenyl)-N,N,α,α-tetramethylpyrazole-1-acetamide, m.p. 161°–163° C.

Analysis: Calc'd. for $C_{15}H_{17}Cl_2N_3O$: C, 55.22; H, 5.25; Cl, 21.74; N, 12.88. Found: C, 54.95; H, 5.07; Cl, 21.23; N, 12.76.

EXAMPLE 199

3-(o-Cyanophenyl)-N,N,α,4-tetramethylpyrazole-1-acetamide

Following the procedure of Example 94, but substituting 3-(o-bromophenyl)-N,N,α,4-tetramethyl-pyrazole-1-acetamide for 4-bromo-N,N,α,-trimethyl-3-phenylpyrazole-1-acetamide, there was obtained 3-(o- cyanophenyl)-N,N,α,4-tetramethylpyrazole-1-acetamide, m.p. 105.5°-108° C.

Analysis: Calc'd. for $C_{16}H_{18}N_4O$: C, 68.06; H, 6.43; N, 19.85. Found: C, 68.05; H, 6.38; N, 19.72.

EXAMPLE 200

4-Ethylthio-N,N,α-trimethyl-3-phenylpyrazole-1-acetamide

Following the procedure of Example 1, but substituting 4-ethylthio-3-phenylpyrazole for 4-methyl-3-phenylpyrazole, there was obtained 4-ethylthio-N,N,α-trimethyl-3-phenylpyrazole-1-acetamide, m.p. 70°-72° C.

Analysis: Calc'd. for $C_{16}H_{21}N_3OS$: C, 63.33; H, 6.98; N, 13.85; S, 10.57. Found: C, 63.71; H, 7.04; N, 13.72; S, 10.53.

EXAMPLE 201

4-Ethylthio-N,N,α,α,-tetramethyl-3-phenylpyrazole-1-acetamide

Following the procedure of Example 95, but substituting 4-ethylthio-N,N,α-trimethyl-3-phenylpyrazole-1-acetamide for N,N,α,4-tetramethyl-3-phenylpyrazole-1-acetamide and methyl iodide for ethyl iodide, there was obtained 4-ethylthio-N,N,α,α,tetramethyl-3-phenylpyrazole-1-acetamide, m.p. 66°-88° C.

Analysis: Calc'd. for $C_{17}H_{23}N_3OS$: C, 64.32; H, 7.30; N, 13.24; S, 10.10. Found: C, 64.19; H, 7.40; N, 13.09; S, 10.24.

EXAMPLE 202

4-Ethyl-N,N,α,-trimethyl-3-phenylpyrazole-1-propionamide

Following the procedure of Example 121, but substituting 4-ethyl-3-phenylpyrazole for 3-phenylpyrazole there is obtained 4-ethyl-N,N,α,-trimethyl-3-phenylpyrazole-1-propionamide, b.p. 175°-180° C./0.04 mm.

Analysis: Calc'd. for $C_{17}H_{23}N_3O$: C, 71.54; H, 8.12; N, 14.73. Found: C, 70.62; H, 8.21; N, 14.63.

EXAMPLE 203

3-(o-Chlorophenyl)-N,N,α,-trimethylpyrazole-1-propionamide

Following the procedure of Example 121, but substituting 3-(o-chlorophenyl)pyrazole for 3-phenylpyrazole there is obtained 3-(o-chlorophenyl)-N,N,α-trimethyl-pyrazole-1-propionamide, m.p. 87°-88° C.

Analysis: Calc'd. for $C_{15}H_{18}ClN_3O$: C, 61.74; H, 6.21; Cl, 12.15; N, 14.40. Found: C, 61.81; H, 6.16; Cl, 12.37; N, 14.59.

EXAMPLE 204

4-Chloro-3-(o-chlorophenyl)-N,N,α-trimethylpyrazole-1-propionamide

Following the procedure of Example 108, but substituting 3-(o-chlorophenyl)-N,N,α-trimethylpyrazole-1-propionamide for N,N,α,4-tetramethyl-3-phenyl-pyrazole-1-acetamide and chlorine for bromine there is obtained 4-chloro-3-(o-chlorophenyl)-N,N,α-trimethyl-pyrazole-1-propionamide, m.p. 91°-92° C.

Analysis: Calc'd. for $C_{15}H_{17}Cl_2N_3O$: C, 55.22; H, 5.25; Cl, 21.74; N, 12.88. Found: C, 55.15; H, 5.35; Cl, 21.96; N, 12.77.

EXAMPLE 205

α,4-Dimethyl-3-phenylpyrazole-1-thioacetamide

Following the procedure of Example 127, but substituting α,4-di-methyl-3-phenylpyrazole-1-acetamide for N,N,α,α,4-pentamethyl-3-phenylpyrazole-1-acetamide there is obtained α,4-dimethyl-3-phenylpyrazole-1-thioacetamide, m.p. 97°-99° C.

Analysis: Calc'd. for $C_{13}H_{15}N_3S$: C, 63.64; H, 6.16; N, 17.13; S, 13.07. Found: C, 63.85; H, 6.21; N, 17.29; S, 13.04.

EXAMPLE 206

3-(o-Chlorophenyl)-N,N,α-tetramethyl-4-isopropyl-pyrazole-1-acetamide

Following the procedure of Example 49, but substituting 3-(o-chlorophenyl)-4-isopropylpyrazole for 4-methyl-3-phenylpyrazole and aqueous dimethylamine for aqueous methylamine there is obtained 3-(o-chlorophenyl)-N,N,α,α-tetramethyl-4-isopropylpyrazole-1-acetamide, m.p. 86°-88° C.

Analysis: Calc'd. for $C_{18}H_{24}ClN_3O$: C, 64.75; H, 7.25; Cl, 10.62; N, 12.59. Found: C, 64.99; H, 7.28; Cl, 10.73; N, 12.98.

EXAMPLE 207

3-(o-Chlorophenyl)-N,N,α,α-tetramethyl-4-propyl-pyrazole-1-acetamide

Following the procedure of Example 49, but substituting 3-(o-chlorophenyl)-4-propylpyrazole for 4-methyl-3-phenylpyrazole and aqueous dimethylamine for aqueous methylamine there is obtained 3-(o-chlorophenyl)-N,N,α,α-tetramethyl-4-propylpyrazole-1-acetamide, m.p. 64°-66° C.

Analysis: Calc'd. for $C_{18}H_{24}ClN_3O$: C, 64.75; H, 7.25; Cl, 10.62; N, 12.59. Found: C, 64.63; H, 7.25; Cl, 10.54; N, 12.75.

EXAMPLE 208

3-(o-Chlorophenyl)-N,α,α,4-tetramethylpyrazole-1-acetamide

Following the procedure of Example 49, but substituting 3-(o-chlorophenyl)-4-methylpyrazole for 4-methyl-3-phenylpyrazole there is obtained 3-(o-chlorophenyl)-N,α,α,4-tetramethylpyrazole-1-acetamide, m.p. 87°-90.5° C.

Analysis: Calc'd. for $C_{15}H_{18}ClN_3O$: C, 61.74; H, 6.22; Cl, 12.15; N, 14.40. Found: C, 61.74; H, 6.31; Cl, 12.30; N, 14.51.

EXAMPLE 209

3-(o-Chlorophenyl)-N,N-diethyl-α,α,4-trimethyl-pyrazole-1-acetamide

Following the procedure of Example 49, but substituting 3-(o-chlorophenyl)-4-methylpyrazole for 4-methyl-3-phenylpyrazole and diethylamine for aqueous methylamine there is obtained 3-(o-chlorophenyl)-N,N,-diethyl-α,α,4-trimethylpyrazole-1-acetamide, m.p. 73°-76° C.

Analysis: Calc'd. for $C_{18}H_{24}ClN_3O$: C, 64.75; H, 7.25; Cl, 10.62; N, 12.59. Found: C, 64.75; H, 7.40; Cl, 10.56; N, 12.63.

EXAMPLE 210

5-chloro-N,N,α-trimethyl-3-phenylpyrazole-1-acetamide

Following the procedure of Example 1, but substituting 3-chloro-5-phenylpyrazole for 4-methyl-3-phenylpyrazole there is obtained 5-N,N,α-trimethyl-3-phenylpyrazole-1-acetamide, m.p. 97°–98° C.

Analysis: Calc'd. for $C_{14}H_{16}ClN_3O$: C, 60.54; H, 5.81; Cl, 12.77, N, 15.13. Found: C, 60.62; H, 5.87; Cl, 12.66; N, 15.02.

EXAMPLE 211

4,5-Dichloro-N,N,α-trimethyl-3-phenylpyrazole-1-acetamide

Following the procedure of Example 108, but substituting 5-chloro-N,N,α-trimethyl-3-phenylpyrazole-1-acetamide for N,N,α,5-tetramethyl-3-phenylpyrazole-1-acetamide and chlorine for bromine there is obtained 4,5-dichloro-N,N,α-trimethyl-3-phenylpyrazole-1-acetamide, m.p. 102°–103° C.

Analysis: Calc'd. for $C_{14}H_{15}Cl_2N_3O$: C, 53.86; H, 4.84; N, 13.46; Cl, 22.71. Found: C, 53.77; H, 4.89; N, 13.57; Cl, 22.99.

EXAMPLE 212

4-Methoxy-N,N,α,α-tetramethyl-3-phenylpyrazole-1-acetamide

Following the procedure of Example 95, but substituting 4-methoxy-N,N,α-trimethyl-3-phenylpyrazole-1-acetamide for N,N,α,4-tetramethyl-3-phenylpyrazole-1-acetamide and methyl iodide for ethyl iodide, there is obtained 4-methoxy-N,N,α,α-tetramethyl-3-phenylpyrazole-1-acetamide, m.p. 114°–116° C.

Analysis: Calc'd. for $C_{16}H_{21}N_3O_2$: C, 66.87; H, 7.37; N, 14.62. Found: C, 67.16; H, 7.60; N, 14.44.

EXAMPLE 213

4-Methoxy-N,N,α-trimethyl-3-phenylpyrazole-1-acetamide

Following the procedure of Example 1, but substituting 4-methoxy-3-phenylpyrazole for 4-methyl-3-phenylpyrazole there is obtained 4-methoxy-N,N,α-trimethyl-3-phenylpyrazole-1-acetamide, m.p. 96.5°–98° C.

Analysis: Calc'd. for $C_{15}H_{19}N_3O_2$: C, 65.91; H, 7.01; N, 15.37. Found: C, 66.35; H, 7.14; N, 15.28.

EXAMPLE 214

3-(o-Chlorophenyl)-N,N-diethyl-α,α,4-trimethylpyrazole-1-thioacetamide

Following the procedure of Example 127, but substituting 3-(o-chlorophenyl)-N,N-diethyl-α,α,4-trimethylpyrazole-1-acetamide for N,N,α,α,4-pentamethyl-3-phenylpyrazole-1-acetamide there is obtained 3-(o-chlorophenyl)-N,N-diethyl-α,α,4-trimethylpyrazole-1-thioacetamide, m.p. 53°–56° C.

Analysis: Calc'd. for $C_{18}H_{24}ClN_3S$: C, 61.78; H, 6.91; Cl, 10.13; N, 12.01; S, 9.16. Found: C, 61.90; H, 6.78; Cl, 10.38; N, 12.13; S, 9.26.

EXAMPLE 215

3-(o-Chlorophenyl)-N,α,α,4-tetramethylpyrazole-1-thioacetamide

Following the procedure of Example 127 but substituting 3-(o-chlorophenyl)-N,α,α,4-tetramethylpyrazole-1-acetamide for N,N,α,α,4-pentamethyl-3-phenylpyrazole-1-acetamide there is obtained 3-(o-chlorophenyl)-N,α,α,4-tetramethylpyrazole-1-thioacetamide, m.p. 71.5°–74.5° C.

Analysis: Calc'd. for $C_{15}H_{18}ClN_3S$: C, 58.52; H, 5.89; Cl, 11.52; N, 13.65; S, 10.42. Found: C, 58.61; H, 5.81; Cl, 11.82; N, 13.80; S, 10.47.

EXAMPLE 216

α-Ethyl-N,N,4-trimethyl-3-(2,5-dimethylphenyl)-pyrazole-1-acetamide

Using the procedure of Example 1, but substituting 2-bromo-N,N-dimethylbutyramide for 2-chloro-N,N-dimethylpropionamide and 4-methyl-3-(2,5-dimethylphenyl)pyrazole for 4-methyl-3-phenylpyrazole there is obtained α-ethyl-N,N,4-trimethyl-3-(2,5-dimethylphenyl)pyrazole-1-acetamide isolated as an oil.

Analysis: Calc'd. for $C_{18}H_{25}N_3O$: C, 72.21; H, 8.42; N, 14.03. Found: C, 71.74; H, 8.52; N, 13.73.

EXAMPLE 217

N,N,α,α,4-Pentamethyl-3-(2,5-dimethylphenyl)-pyrazole-1-acetamide

Following the procedure of Example 49, but substituting 4-methyl-3-(2,5-dimethylphenyl)pyrazole for 4-methyl-3-phenylpyrazole and aqueous dimethylamine for aqueous methylamine there is obtained N,N,α,α,4-pentamethyl-3-(2,5-dimethylphenyl)pyrazole-1-acetamide, m.p. 93°–95° C.

Analysis: Calc'd. for $C_{18}H_{25}N_3O$: C, 72.21; H, 8.42; N, 14.03. Found: C, 72.21; H, 8.39; N, 13.98.

EXAMPLE 218

N,N,α,4-Tetramethyl-(3-(2,4-dimethylphenyl)pyrazole-1-acetamide

Following the procedure of Example 1, but substituting 4-methyl-3-(2,4-dimethylphenyl)pyrazole for 4-methyl-3-phenylpyrazole, there is obtained N,N,α,4-tetramethyl-3-(2,4-dimethylphenyl)pyrazole-1-acetamide isolated as an oil.

Analysis: Calc'd. for $C_{17}H_{23}N_3O$: C, 71.55; H, 8.12; N, 14.72. Found: C, 70.83; H, 8.26; N, 14.46.

EXAMPLE 219

α-Ethyl-N,N,4-trimethyl-3-(2,4-dimethylphenyl)-pyrazole-1-acetamide

Using the procedure of Example 1, but substituting 2-bromo-N,N-dimethylbutyramide for 2-chloro-N,N-dimethylpropionamide and 4-methyl-3-(2,4-dimethylphenyl)pyrazole for 4-methyl-3-phenylpyrazole there is obtained α-ethyl-N,N,4-trimethyl-3-(2,4-dimethylphenyl)pyrazole-1-acetamide isolated as an oil.

Analysis: Calc'd. for $C_{18}H_{25}N_3O$: C, 72.21; H, 8.42; N, 14.03. Found: C, 72.22; H, 8.58; N, 13.82.

EXAMPLE 220

3-(o-Methoxyphenyl)-N,N,α,α,4-pentamethylpyrazole-1-acetamide

Following the procedure of Example 49, but substituting 3-(o-methoxyphenyl)-4-methylpyrazole for 4-methyl-3-phenylpyrazole and aqueous dimethylamine for aqueous methylamine there is obtained 3-(o-methoxyphenyl)-N,N,α,α,4-pentamethylpyrazole-1-acetamide, m.p. 146°–148° C.

Analysis: Calc'd. for $C_{17}H_{23}N_3O_2$: C, 67.75; H, 7.69; N, 13.94. Found: C, 67.93; H, 7.76; N, 14.11.

EXAMPLE 221

α-Ethyl-3-(o-methoxyphenyl)-N,N,4-trimethyl-pyrazole-1-acetamide

Using the procedure of Example 1, but substituting 2-bromo-N,N-dimethylbutyramide for 2-chloro-N,N-dimethylpropionamide and 3-(o-methoxyphenyl)-4-methylpyrazole for 4-methyl-3-phenylpyrazole there is obtained α-ethyl-3-(o-methoxyphenyl)-N,N,4-trimethylpyrazole-1-acetamide, m.p. 79°–81° C.

Analysis: Calc'd. for $C_{17}H_{23}N_3O_2$: C, 67.75; H, 7.69; N, 13.94. Found: C, 67.67; H, 7.76; N, 14.00.

EXAMPLE 222

3-(o-Chlorophenyl)-N,N-diethyl-α,4-dimethylpyrazole-1-acetamide

Using the procedure of Example 1, but substituting 2-chloro-N,N-diethylpropionamide for 2-chloro-N,N-dimethylpropionamide and 3-(o-chlorophenyl)-4-methylpyrazole for 4-methyl-3-phenylpyrazole there is obtained 3-(o-chlorophenyl)-N,N-diethyl-α,4-dimethylpyrazole-1-acetamide, b.p. 178°–182° C./0.4 mm.

Analysis: Calc'd. for $C_{17}H_{22}ClN_3O$: C, 64.04; H, 6.64; Cl, 11.12; N, 13.18. Found: C, 64.02; H, 6.76; Cl, 11.10; N, 12.91.

EXAMPLE 223

N,N,α,4-Tetramethyl-3-(2,5-dimethylphenyl)pyrazole-1-acetamide

Following the procedure of Example 1, but substituting 4-methyl-3-(2,5-dimethylphenyl)pyrazole for 4-methyl-3-phenylpyrazole there is obtained N,N,α,4-tetramethyl-3-(2,5-dimethylphenyl)pyrazole-1-acetamide isolated as an oil.

Analysis: Calc'd. for $C_{17}H_{23}N_3O$: C, 71.55; H, 8.12; N, 14.72. Found: C, 71.47; H, 8.22; N, 14.51.

EXAMPLE 224

N,N,α,α,4-Pentamethyl-3-(2,4-dimethylphenyl)-pyrazole-1-acetamide

Following the procedure of Example 49, but substituting 4-methyl-3-(2,4-dimethylphenyl)pyrazole for 4-methyl-3-phenylpyrazole and aqueous dimethylamine for aqueous methylamine there is obtained N,N,α,α,4-pentamethyl-3-(2,4-dimethylphenyl)pyrazole-1-acetamide, m.p. 110°–111.5° C.

Analysis: Calc'd. for $C_{18}H_{25}N_3O$: C, 72.21; H, 8.42; N, 14.03. Found: C, 72.33; H, 8.48; N, 14.17.

EXAMPLE 225

3-(2-Chloro-5-methylphenyl)-N,N,α,4-tetramethyl-pyrazole-1-acetamide

Following the procedure of Example 1, but substituting 3-(2-chloro-5-methylphenyl)-4-methylpyrazole for 4-methyl-3-phenylpyrazole there is obtained 3-(2-chloro-5-methylphenyl)-N,N,α,4-tetramethylpyrazole-1-acetamide isolated as an oil.

Analysis: Calc'd. for $C_{16}H_{20}ClN_3O$: C, 62.84; H, 6.59; N, 13.74. Found: C, 62.55; H, 6.65; N, 13.92.

EXAMPLE 226

3-(2-chloro-5-methylphenyl)-α-ethyl-N,N,4-trimethyl-pyrazole-1-acetamide

Using the procedure of Example 1, but substituting 2-bromo-N,N-dimethylbutyramide for 2-chloro-N,N-dimethylpropionamide and 3-(2-chloro-5-methylphenyl)-4-methylpyrazole for 4-methyl-3-phenylpyrazole there is obtained 3-(2-chloro-5-methylphenyl)-α-ethyl-N,N,4-trimethylpyrazole-1-acetamide isolated as an oil.

Analysis: Calc'd. for $C_{17}H_{22}ClN_3O$: C, 63.84; H, 6.93; N, 13.14. Found: C, 63.69; H, 6.69; N, 12.96.

EXAMPLE 227

3-(2-Chloro-5-methylphenyl)-N,N,α,α,4-pentamethyl-pyrazole-1-acetamide

Following the procedure of Example 49, but substituting 3-(2-chloro-5-methylphenyl)-4-methylpyrazole for 4-methyl-3-phenylpyrazole and aqueous dimethylamine for aqueous methylamine there is obtained 3-(2-chloro-5-methylphenyl)-N,N,α,α,4-pentamethyl-pyrazole-1-acetamide, m.p. 106°–107.5° C.

Analysis: Calc'd. for $C_{17}H_{22}ClN_3O$: C, 63.84; H, 6.93; N, 13.14. Found: C, 63.62; H, 6.92; N, 13.06.

EXAMPLE 228

3-(4-Chloro-2-methylphenyl)-N,N,α,4-tetramethyl-pyrazole-1-acetamide

Following the procedure of Example 1, but substituting 3-(4-chloro-2-methylphenyl)-4-methylpyrazole for 4-methyl-3-phenylpyrazole, there is obtained 3-(4-chloro-2-methylphenyl)-N,N,α,4-tetramethylpyrazole-1-acetamide isolated as an oil.

Analysis: Calc'd. for $C_{16}H_{20}ClN_3O$: C, 62.84; H, 6.59; N, 13.74. Found: C, 62.59; H, 6.81; N, 13.62.

EXAMPLE 229

3-(4-Chloro-2-methylphenyl)-α-ethyl-N,N,4-trimethyl-pyrazole-1-acetamide

Using the procedure of Example 1, but substituting 2-bromo-N,N-dimethylbutyramide for 2-chloro-N,N-dimethylpropionamide and 3-(4-chloro-2-methylphenyl)-4-methylpyrazole for 4-methyl-3-phenylpyrazole there is obtained 3-(4-chloro-2-methylphenyl)-α-ethyl-N,N,4-trimethylpyrazole-1-acetamide, m.p. 89°–92° C.

Analysis: Calc'd. for $C_{17}H_{22}ClN_3O$: C, 63.84; H, 6.93; N, 13.14. Found: C, 63.96; H, 7.07; N, 13.29.

EXAMPLE 230

3-(4-Chloro-2-methylphenyl)-N,N,α,α,4-pentamethyl-pyrazole-1-acetamide

Following the procedure for Example 49, but substituting 3-(4-chloro-2-methylphenyl)-4-methylpyrazole for 4-methyl 3-phenylpyrazole and aqueous dimethylamine for aqueous methylamine there is obtained 3-(4-chloro-2-methylphenyl)N,N,α,α,4-pentamethyl-pyrazole-1-acetamide, m.p. 99°–100° C.

Analysis: Calc'd. for $C_{17}H_{22}ClN_3O$: C, 63.84; H, 6.93; N, 13.14. Found: C, 63.63; H, 7.10; N, 13.38.

EXAMPLE 231

3-(2-Chloro-4-methylphenyl)-N,N,α,4-tetramethylpyrazole-1-acetamide

Following the procedure of Example 1, but substituting 3-(2-chloro-4-methylphenyl)-4-methylpyrazole for 4-methyl 3-phenylpyrazole there is obtained 3-(2-chloro-4-methylphenyl)-N,N,α,4-tetramethylpyrazole-1-acetamide isolated as an oil.

Analysis: Calc'd. for $C_{16}H_{20}ClN_3O$: C, 63.84; H, 6.59; N, 13.74. Found: C, 63.10; H, 6.34; N, 13.45.

EXAMPLE 232

3-(2-Chloro-4-methylphenyl)-α-ethyl-N,N,4-trimethylpyrazole-1-acetamide

Using the procedure of Example 1, but substituting 2-bromo-N,N-dimethylbutyramide for 2-chloro-N,N-dimethylpropionamide and 3-(2-chloro-4-methylphenyl)-4-methylpyrazole for 4-methyl-3-phenylpyrazole there is obtained 3-(2-chloro-4-methylphenyl)-α-ethyl-N,N,4-trimethylpyrazole-1-acetamide isolated as an oil.

Analysis: Calc'd. for $C_{17}H_{22}ClN_3O$: C, 63.84; H, 6.93; N, 13.14. Found: C, 63.89; H, 7.00; N, 13.19.

EXAMPLE 233

N,N,α-Trimethyl-α,3-diphenylpyrazole-1-acetamide

Following the procedure of Example 95, but substituting N,N-dimethyl-α,3-diphenylpyrazole-1-acetamide for N,N,α,4-tetramethyl-3-phenylpyrazole-1-acetamide and methyl iodide for ethyl iodide, there is obtained N,N,α-trimethyl-α,3-diphenylpyrazole-1-acetamide, m.p. 129°–131.5° C.

Analysis: Calc'd. for $C_{20}H_{21}N_3O$: C, 75.24; H, 6.58; N, 13.16. Found: C, 75.25; H, 6.65; N, 13.19.

EXAMPLE 234

3-(o-Chlorophenyl)-N,N,α,4-tetramethyl-α-phenylpyrazole-1-acetamide

Following the procedure of Example 95, but substituting 3-(o-chlorophenyl)-N,N,4-trimethyl-α-phenylpyrazole-1-acetamide for N,N,α,4-tetramethyl-3-phenylpyrazole-1-acetamide and methyl iodide for ethyl iodide, there is obtained 3-(o-chlorophenyl)-N,N,α,4-tetramethyl-α-phenylpyrazole-1-acetamide, m.p. 96°–99° C.

Analysis: Calc'd. for $C_{21}H_{22}ClN_3O$: C, 68.66; H, 5.99; Cl, 9.67; N, 11.44. Found: C, 68.62; H, 5.99; Cl, 9.65; N, 11.77.

EXAMPLE 235

3-(2-Chloro-4-methylphenyl)-N,N,α,α,4-pentamethylpyrazole-1-acetamide

Following the procedure of Example 49, but substituting 3-(2-chloro-4-methylphenyl)-4-methylpyrazole for 4-methyl-3-phenylpyrazole and aqueous dimethylamine for aqueous methylamine there is obtained 3-(2-chloro-4-methylphenyl)-N,N,α,α,4-pentamethylpyrazole-1-acetamide, m.p. 126°–128° C.

Analysis: Calc'd. for $C_{17}H_{22}ClN_3O$: C, 63.84; H, 6.93; N, 13.14. Found: C, 64,01; H, 7.18; N, 13.33.

EXAMPLE 236

3-(2,6-Dichlorophenyl)-N,N,α,4-tetramethylpyrazole-1-acetamide

Following the procedure of Example 1, but substituting 3-(2,6-dichlorophenyl)-4-methylpyrazole for 4-methyl-3-phenylpyrazole there is obtained 3-(2,6-dichlorophenyl)-N,N,α,4-tetramethylpyrazole-1-acetamide.

EXAMPLE 237

3-(2,6-Dichlorophenyl)-N,N,α,α,4-pentamethylpyrazole-1-acetamide

Following the procedure of Example 49, but substituting 3-(2,6-dichlorophenyl)-4-methylpyrazole for 4-methyl-3-phenylpyrazole and aqueous dimethylamine for aqueous methylamine there is obtained 3-(2,6-dichlorophenyl)-N,N,α,α,4-pentamethylpyrazole-1-acetamide.

EXAMPLE 238

3-(o-Iodiphenyl)-N,N,α,4-tetramethylpyrazole-1-acetamide

Following the procedure of Example 1, but substituting 3-(o-iodophenyl)-4-methylpyrazole for 4-methyl-3-phenylpyrazole there is obtained 3-(o-iodophenyl)-N,N,α,4-tetramethylpyrazole-1-acetamide.

EXAMPLE 239

3-(o-Bromophenyl)-4-ethyl-N,N,α-trimethylpyrazole-1-acetamide

Following the procedure of Example 1, but substituting 3-(o-bromophenyl)-4-ethylpyrazole for 4-methyl-3-phenylpyrazole there is obtained 3-(o-bromophenyl)-4-ethyl-N,N,α-trimethylpyrazole-1-acetamide.

EXAMPLE 240

3-(o-Bromophenyl)-4-ethyl-N,N,α,α-tetramethylpyrazole-1-acetamide

Following the procedure of Example 49, but substituting 3-(o-bromophenyl)-4-ethylpyrazole for 4-methyl-3-phenylpyrazole and aqueous dimethylamine for aqueous methylamine there is obtained 3-(o-bromophenyl)-4-ethyl-N,N,α,α-tetramethylpyrazole-1-acetamide.

EXAMPLE 241

4-Ethyl-3-(o-fluorophenyl)-N,N,α,α-tetramethylpyrazole-1-acetamide

Following the procedure of Example 49, but substituting 4-ethyl-3-(o-fluorophenyl)pyrazole for 4-methyl-3-phenylpyrazole and aqueous dimethylamine for aqueous methylamine there is obtained 4-ethyl-3-(o-fluorophenyl)-N,N,α,α-tetramethylpyrazole-1-acetamide.

EXAMPLE 242

N,N,-Dimethyl-1-[(3-o-chlorophenyl)-4-methylpyrazol-1-yl]cyclopropanecarboxamide Following the procedure of Example 95, but substituting α-2-bromoethyl-3-(o-chlorophenyl)-N,N,4-trimethylpyrazole-1-acetamide for N,N,α,4-tetramethyl-3-phenylpyrazole-1-acetamide and without addition of ethyl iodide there is obtained N,N-dimethyl-1-[(3-o-chlorophenyl)-4-methylpyrazol-1-yl]cyclopropanecarboxamide.

EXAMPLE 243

N,N-Dimethyl-1-]3-o-(chlorophenyl)-4-ethylpyrazol-1-yl]cyclopropanecarboxamide

Following the procedure of Example 95, but substituting α-2-bromoethyl-3-(o-chlorophenyl)-4-ethyl-N,N-dimethylpyrazole-1-acetamide for N,N,α,4-tetramethyl-3-phenylpyrazole-1-acetamide and without addition of ethyl iodide there is obtained N,N-dimethyl-1-[3-o-(chlorophenyl)-4-ethylpyrazol-1-yl]cyclopropanecarboxamide.

EXAMPLE 244

3-(o-Ethylphenyl)-N,N,α,4-tetramethylpyrazole-1-acetamide

Following the procedure of Example 1, but substituting 3-(o-ethylphenyl)-4-methylpyrazole for 4-methyl-3-phenylpyrazole there is obtained 3-(o-ethylphenyl)-N,N,α,4-tetramethylpyrazole-1-acetamide.

EXAMPLE 245

3-(o-Ethylphenyl)-N,N,α,α,4-pentamethylpyrazole-1-acetamide

Following the procedure of Example 49, but substituting 3-(o-ethylphenyl)-4-methylpyrazole for 4-methyl-3-phenylpyrazole and aqueous dimethylamine for aqueous methylamine there is obtained 3-(o-ethylphenyl)-N,N,α,α,4-pentamethylpyrazole-1-acetamide.

EXAMPLE 246

N,N,α,4-Tetramethyl-3-(o-isopropylphenyl)pyrazole-1-acetamide

Following the procedure of Example 1, but substituting 3-(o-isopropylphenyl)-4-methylpyrazole for 4-methyl-3-phenylpyrazole there is obtained N,N,α,4-tetramethyl-3-(o-isopropylphenyl)pyrazole-1-acetamide.

EXAMPLE 247

N,N,α,α,4-Pentamethyl-3-(o-isopropylphenyl)-pyrazole-1-acetamide

Following the procedure of Example 49, but substituting 3-(o-isopropylphenyl)-4-methylpyrazole for 4-methyl-3-phenylpyrazole and aqueous dimethylamine for aqueous methylamine there is obtained N,N,α,α,4-pentamethyl-3-(o-isopropylphenyl)pyrazole-1-acetamide.

EXAMPLE 248

3-(o-Iodophenyl)-N,N,α,α,4-pentamethylpyrazole-1-acetamide

Following the procedure of Example 49, but substituting 3-(o-iodophenyl)-4-methylpyrazole for 4-methyl-3-phenylpyrazole and aqueous dimethylamine for aqueous methylamine there is obtained 3-(o-iodophenyl)-N,N,α,α,4-pentamethylpyrazole-1-acetamide.

EXAMPLE 249

N,N,α,4-Tetramethyl-3-(o-phenylphenyl)pyrazole-1-acetamide

Following the procedure of Example 1, but substituting 4-methyl-3-(o-phenylphenyl)pyrazole for 4-methyl-3-phenylpyrazole there is obtained N,N,α,4-tetramethyl-3-(o-phenylphenyl)pyrazole-1-acetamide.

EXAMPLE 250

N,N,α,α,4-Pentamethyl-3-(o-phenylphenyl)pyrazole-1-acetamide

Following the procedure of Example 49, but substituting 4-methyl-3-(o-phenylphenyl)pyrazole for 4-methyl-3-phenylpyrazole and aqueous dimethylamine for aqueous methylamine there is obtained N,N,α,α,4-pentamethyl-3-(o-phenylphenyl)pyrazole-1-acetamide.

EXAMPLE 251

N,N,α,4-Tetramethyl-3-(o-benzylphenyl)pyrazole-1-acetamide

Following the procedure of Example 1, but substituting 3-(o-benzylphenyl)-4-methylpyrazole for 4-methyl-3-phenylpyrazole there is obtained N,N,α,4-tetramethyl-3-(o-benzylphenyl)pyrazole-1-acetamide.

EXAMPLE 252

N,N,α,α,4-Pentamethyl-3-(o-benzylphenyl)pyrazole-1-acetamide

Following the procedure of Example 49, but substituting 3-(o-benzylphenyl)-4-methylpyrazole for 4-methyl-3-phenylpyrazole and aqueous dimethylamine for aqueous methylamine there is obtained N,N,α,α,4-pentamethyl-3-(o-benzylphenyl)pyrazole-1-acetamide.

EXAMPLE 253

N,N,α,4-Tetramethyl-3-[o-(2-phenylethyl)phenyl]-pyrazole-1-acetamide

Following the procedure of Example 1, but substituting 3-[o-(2-phenylethyl)phenyl]-4-methylpyrazole for 4-methyl-3-phenylpyrazole there is obtained N,N,α,4-tetramethyl-3-[o-(2-phenylethyl)phenyl]pyrazole-1-acetamide.

EXAMPLE 254

N,N,α,α,4-Pentamethyl-3-[o-(2-phenylethyl)phenyl]-pyrazole-1-acetamide

Following the procedure of Example 49, but substituting 4-methyl-3-[o-(2-phenylethyl)phenyl]pyrazole for 4-methyl-3-phenylpyrazole and aqueous dimethylamine for aqueous methylamine there is obtained N,N,α,α,4-pentamethyl-3-[o-(2-phenylethyl)phenyl]-pyrazole-1-acetamide.

EXAMPLE 255

3-(o-acetylphenyl)-N,N,α,α,4-pentamethylpyrazole-1-acetamide

Following the procedure of Example 49, but substituting 3-(o-acetyphenyl)-4-methylpyrazole for 4-methyl-3-phenylpyrazole and aqueous dimethylamine for aqueous methylamine there is obtained 3-(o-acetylphenyl)-N,N,α,α,4-pentamethylpyrazole-1-acetamide.

EXAMPLE 256

3-[o-(carbomethoxy)phenyl]-N,N,α,α,4-pentamethyl-pyrazole-1-acetamide

Following the procedure of Example 49, but substituting 3-(o-carbomethoxyphenyl)-4-methylpyrazole for 4-methyl-3-phenylpyrazole and aqueous dimethylamine for aqueous methylamine there is obtained 3-[o-(carbomethoxy)phenyl]N,N,α,α,4-pentamethylpyrazole-1-acetamide.

EXAMPLE 257

3-[o-(dimethylcarbamoyl)phenyl]-N,N,α,α,4-pentamethylpyrazole-1-acetamide

Following the procedure of Example 49, but substituting 3-(o-dimethylcarbamoyl)phenyl-4-methylpyrazole for 4-methyl-3-phenylpyrazole and aqueous dimethylamine for aqueous methylamine there is obtained 3-[o-(dimethylcarbamoyl)phenyl]N,N,α,α,4-pentamethylpyrazole-1-acetamide.

EXAMPLE 258

4-Ethyl-N,N,α,α-tetramethyl-3-(o-phenylphenyl)-pyrazole-1-acetamide

Following the procedure of Example 49, but substituting 4-ethyl-3-o-phenylphenylpyrazole for 4-methyl-3-phenylpyrazole and aqueous dimethylamine for aqueous methylamine there is obtained 4-ethyl-N,N,α,α-tetramethyl-3-(o-phenylphenyl)pyrazole-1-acetamide.

EXAMPLE 259

3-(o-Benzylphenyl)-4-ethyl-N,N,α,α-tetramethylphenylacetamide

Following the procedure of Example 49, but substituting 3-(o-benzylphenyl)-4-ethylpyrazole for 4-methyl-3-phenylpyrazole and aqueous dimethylamine for aqueous methylamine there is obtained 3-(o-benzylphenyl)-4-ethyl-N,N,α,α-tetramethylphenylacetamide.

EXAMPLE 260

4-Ethyl-N,N,α,α-tetramethyl-3-[o-(2-phenylethyl)-phenyl]pyrazole-1-acetamide

Following the procedure of Example 49, but substituting 4-ethyl-3-[o-(2-phenylethyl)phenyl]pyrazole for 4-methyl-3-phenylpyrazole and aqueous dimethylamine for aqueous methylamine there is obtained 4-ethyl-N,N,α,α-tetramethyl-3-[o-(2-phenylethyl)phenyl]-pyrazole-1-acetamide.

EXAMPLE 261

4-Ethyl-3-(o-ethylphenyl)-N,N,α,α-tetramethyl-pyrazole-1-acetamide

Following the procedure of Example 49, but substituting 4-ethyl-3-(o-ethylphenyl)pyrazole for 4-methyl-3-phenylpyrazole and aqueous dimethylamine for aqueous methylamine there is obtained 4-ethyl-3-(o-ethylphenyl)-N,N,α,α-tetramethylpyrazole-1-acetamide.

We claim:
1. A compound of the formula:

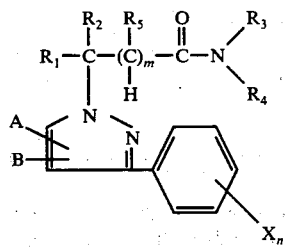

where $R_1$ is hydrogen, alkyl of 1 to 7 carbon atoms, inclusive, haloalkyl of 1 to 7 carbon atoms, inclusive, phenyl, benzyl or cycloalkyl of 3 to 6 carbon atoms, inclusive, with the proviso that when $R_1$ is benzyl or cycloalkyl, $m = 0$; $R_2$ and $R_5$ are the same or different and are hydrogen, halogen, alkyl of 1 to 6 carbon atoms, inclusive, haloalkyl of 1 to 6 carbon atoms, inclusive, or phenyl; $R_1$ and $R_2$ together with the attached carbon atom can be cycloalkyl of 3 to 6 carbon atoms, inclusive, when $m = O$; $m$ is O or 1 provided that when $m = O$, $R_1$ is not hydrogen and when $m = 1$ at least one of $R_2$ or $R_5$ is hydrogen; $R_3$ is hydrogen, alkyl of from 1 to 8 carbon atoms, inclusive, phenyl or benzyl; $R_4$ is hydrogen, or alkyl of from 1 to 6 carbon atoms, inclusive, and $R_3$ and $R_4$ can be joined together to form a heterocyclic ring selected from the group consisting of pyrrolidine and piperidine; A and B are the same or different and are hydrogen, alkyl of from 1 to 6 carbon atoms, inclusive, phenyl, halogen, cyano, haloalkyl of 1 to 6 carbon atoms, inclusive, alkoxy or alkylthio in which the alkyl group is from 1 to 3 carbon atoms, inclusive or trifluoromethyl and when adjacent can be joined to form a ring of from 5 to 7 carbon atoms, inclusive; X is halogen, nitro, cyano, acetyl, dimethylcarbamoyl, alkyl, haloalkyl, alkoxy or carboalkoxy in which the alkyl group is from 1 to 3 carbon atoms, inclusive, phenyl, benzyl, 2-phenylethyl and $n$ is 0, 1, or 2; or an acid addition salt thereof.

2. A compound according to claim 1 which is N,N,α,4-tetramethyl-3-phenylpyrazole-1-acetamide.

3. A compound according to claim 1 which is N,N,α-trimethyl-3-phenylpyrazole-1-acetamide.

4. A compound according to claim 1 which is 4-bromo-N,N,α-trimethyl-3-phenylpyrazole-1-acetamide.

5. A compound according to claim 1 which is 4-chloro-N,N,α-trimethyl-3-phenylpyrazole-1-acetamide.

6. A compound according to claim 1 which is 4-ethyl-N,N,α-trimethyl-3-phenylpyrazole-1-acetamide.

7. A compound according to claim 1 which is N,N,α,4,5-pentamethyl-3-phenylpyrazole-1-acetamide.

8. A compound according to claim 1 which is N,N,α-trimethyl-3-(o-tolyl)pyrazole-1-acetamide.

9. A compound according to claim 1 which is N,N,α,4-tetramethyl-3-(o-methoxyphenyl)pyrazole-1-acetamide.

10. A compound according to claim 1 which is 3-(o-chlorophenyl)-N,N,α-trimethylpyrazole-1-acetamide.

11. A compound according to claim 1 which is 3-(o-methoxyphenyl)-N,N,α-trimethylpyrazole-1-acetamide.

12. A compound according to claim 1 which is 3-(o-chlorophenyl)-N,N,α,4-tetramethylpyrazole-1-acetamide.

13. A compound according to claim 1 which is N,N,α,4-tetramethyl-3-(o-tolyl)pyrazole-1-acetamide.

14. A compound according to claim 1 which is N,N,α-trimethyl-3-(2,6-dichlorophenyl)pyrazole-1-acetamide.

15. A compound according to claim 1 which is 4-chloro-N,N-diethyl-α-methyl-3-phenylpyrazole-1-acetamide.

16. A compound according to claim 1 which is α-ethyl-N,N,4-trimethyl-3-phenylpyrazole-1-acetamide.

17. A compound according to claim 1 which is 3-(o-chlorophenyl)-α-ethyl-N,N-dimethylpyrazle-1-acetamide.

18. A compound according to claim 1 which is α-ethyl-N,N-dimethyl-3-(o-tolyl)pyrazole-1-acetamide.

19. A compound according to claim 1 which is 3-(o-chlorophenyl)-α-ethyl-N,N,4-trimethylpyrazole-1-acetamide.

20. A compound according to claim 1 which is α-ethyl-N,N,4-trimethyl-3-(o-tolyl)pyrazole-1-acetamide.

21. A compound according to claim 1 which is α-butyl-N,N,4-trimethyl-3-phenylpyrazole-1-acetamide.

22. A compound according to claim 1 which is N,αλ,α,4-tetramethyl-3-phenylpyrazole-1-acetamide.

23. A compound according to claim 1 which is N-ethyl-α,α,4-trimethyl-3-phenylpyrazole-1-acetamide.

24. A compound according to claim 1 which is α,α,4-trimethyl-3-phenyl-N-isopropylpyrazole-1-acetamide.

25. A compound according to claim 1 which is α,α,4-trimethyl-3-phenyl-N-propylpyrazole-1-acetamide.

26. A compound according to claim 1 which is N-butyl-α,α,4-trimethyl-3-phenylpyrazole-1-acetamide.

27. A compound according to claim 1 which is N-tert-butyl-α,α,4-trimethyl-3-phenylpyrazole-1-acetamide.

28. A compound according to claim 1 which is α,α,4-trimethyl-3-phenylpyrazole-1-acetanilide.

29. A compound according to claim 1 which is N,αλ,α,4-tetramethyl-3-phenylpyrazole-1-acetanilide.

30. A comound according to claim 1 which is N-benzyl-α,α,4-trimethyl-3-phenylpyrazole-1-acetamide.

31. A compound according to claim 1 which is N,N,α,α,4-pentamethyl-3-phenylpyrazole-1-acetamide.

32. A compound according to claim 1 which is N,N-diethyl-α,α,4-trimethyl-3-phenylpyrazole-1-acetamide.

33. A compound according to claim 1 which is N,N,α,α-tetramethyl-3-phenylpyrazole-1-acetamide.

34. A compound according to claim 1 which is 3-(o-chlorophenyl)-N,N,α,α,-tetramethylpyrazole-1-acetamide.

35. A compound according to claim 1 which is N,N,α,α-tetramethyl-3-(o-tolyl)pyrazole-1-acetamide.

36. A compound according to claim 1 which is N,N,α,α-pentamethyl-3-o-tolyl)pyrazole-1-acetamide.

37. A compound according to claim 1 shich is α,4-dimethyl-3-phenylpyrazole-1-acetamide.

38. A compound according to claim 1 which is N,α,4-trimethyl-3-phenylpyrazole-1-acetamide.

39. A compound according to claim 1 which is N-ethyl-α,4-dimethyl-3-phenylpyrazole-1-acetamide.

40. A compound according to claim 1 which is N-butyl-α,4-dimethyl-3-phenylpyrazole-1-acetamide.

41. A compound according to claim 1 which is N-ethyl-N,α,4-trimethyl-3-phenylpyrazole-1-acetamide.

42. A compound according to claim 1 which is N,N-diethyl-α,4-dimethyl-3-phenylpyrazole-1-acetamide.

43. A compound according to claim 1 which is 1-[2-(4-methyl-3-phenylpyrazole-1-yl)propionyl]pyrrolidine.

44. A compound according to claim 1 which is α,4-dimethyl-3-phenyl-N,N-dipropylpyrazole-1-acetamide.

45. A compound according to claim 1 which is N,4-dimethyl-3-phenyl-α-propylpyrazole-1-acetamide.

46. A compound according to claim 1 which is N,N,4-trimethyl-3-phenyl-α-propylpyrazole-1acetamide.

47. A compound according to claim 1 which is N,N-diethyl-4-methyl-3-phenyl-α-propylpyrazole-1-acetamide.

48. A compound according to claim 1 which is α-ethyl-N,N-dimethyl-3-phenylpyrazole-1-acetamide.

49. A compound according to claim 1 which is N,N,α-triethyl-3-phenylpyrazole-1-acetamide.

50. A compound according to claim 1 which is N,N,α-triethyl-4-methyl-3-phenylpyrazole-1-acetamide.

51. A compound according to claim 1 which is α-isopropyl-N,N,4-trimethyl-3-phenylpyrazole-1-acetamide.

52. A compound according to claim 1 which is 4-chloro-α-ethyl-N,N-dimethyl-3-phenylpyrazole-1-acetamide.

53. A compound according to claim 1 which is 4-chloro-N,N,α-triethyl-3-phenylpyrazole-1-acetamide.

54. A compound according to claim 1 which is 4-cyano-N,N,α-trimethyl-3-phenylpyrazole-1-acetamide.

55. A compound according to claim 1 which is α-ethyl-N,N,α,4-tetramethyl-3-phenylpyrazole-1-acetamide.

56. A compound according to claim 1 which is N,N,α,4-tetramethyl-3-phenyl-α-propylpyrazole-1-acetamide.

57. A compound according to claim 1 which is α,α-diethyl-N,N,4-trimethyl-3-phenylpyrazole-1-acetamide.

58. A compound according to claim 1 which is α-ethyl-N,N,4-trimethyl-3-phenyl-α-propylpyrazole-1-acetamide.

59. A compound according to claim 1 which is N,N,α,4-tetramethyl-α,3-diphenylpyrazole-1-acetamide.

60. A compound according to claim 1 which is N,N-dimethyl-1-(4-methyl-3-phenylpyrazol-1-yl)cyclopropanecarboxamide.

61. A compound according to claim 1 which is N,N,-dimethyl-1-(4-methyl-3-phenylpyrazol-1-yl)cyclobutanecarboxamide.

62. A compound according to claim 1 which is N,N-dimethyl-1-(4-methyl-3-phenylpyrazol-1-yl)cyclopentanecarboxamide.

63. A compound according to claim 1 which is N,N-dimethyl-1-(3-phenylpyrazol-1-yl)cyclopropanecarboxamide.

64. A compound according to claim 1 which is N,N-dimethyl-1-(3-phenylpyrazol-1-yl)cyclobutanecarboxamide.

65. A compound according to claim 1 which is 4-bromo-N,N,α,5-tetramethyl-3-phenylpyrazole-1-acetamide.

66. A compound according to claim 1 which is 4-bromo-α-ethyl-N,N-dimethyl-3-phenylpyrazole-1-acetamide.

67. A compound according to claim 1 which is 4-chloro-3-(o-chlorophenyl)-N,N,α-trimethylpyrazole-1-acetamide.

68. A compound according to claim 1 which is 4-chloro-N,N,α-trimethyl-3-(o-tolyl)pyrazole-1-acetamide.

69. A compound according to claim 1 which is 4-chloro-N,N,α-trimethyl-3-(o-methoxyphenyl)pyrazole-1-acetamide.

70. A compound according to claim 1 which is 4-chloro-N,N,α,α-tetramethyl-3-phenylpyrazole-1-acetamide.

71. A compound according to claim 1 which is 4-chloro-N,N-dimethyl-3-phenyl-α-propylpyrazole-1-acetamide.

72. A compound according to claim 1 which is 4-chloro-N,N,α-trimethyl-3-(2,6-dichlorophenyl)-pyrazole-1-acetamide.

73. A compound according to claim 1 which is 4-chloro-3-(o-chlorophenyl)-α-ethyl-N,N-dimethyl-pyrazole-1-acetamide.

74. A compound according to claim 1 which is 4-chloro-3-(o-chlorophenyl)-N,N,α,α-tetramethylpyrazole-1-acetamide.

75. A compound according to claim 1 which is 4-chloro-N,N,α,α-tetramethyl-3-(o-tolyl)pyrazole-1-acetamide.

76. A compound according to claim 1 which is 3-(ochlorophenyl)-N,N,α,α,4-pentamethylpyrazole-1-acetamide.

77. A compound according to claim 1 which is 4-chloro-α-ethyl-N,N-dimethyl-3-(o-tolyl)pyrazole-1-acetamide.

78. A compound according to claim 1 which is the hydrochloride salt of N,N,α,4-tetramethyl-3-phenylpyrazole-1-acetamide.

79. A compound according to claim 1 which is the p-toluenesulfonate salt of N,N,α,4-tetramethyl-3-phenylpyrazole-1-acetamide.

80. A compound according to claim 1 which is the tridecylsulfonate salt of N,N,α,4-tetramethyl-3-phenylpyrazole-1-acetamide.

81. A compound according to claim 1 which is α,4-diethyl-N,N-dimethyl-3-phenylpyrazole-1-acetamide.

82. A compound according to claim 1 which is 3-(o-chlorophenyl)-4-ethyl-N,N,α-trimethylpyrazole-1-acetamide.

83. A compound according to claim 1 which is 3-(o-chlorophenyl)-α,4-diethyl-N,N-dimethylpyrazole-1-acetamide.

84. A compound according to claim 1 which is α-ethyl-3-(o-fluorophenyl)-N,N,4-trimethylpyrazole-1-acetamide.

85. A compound according to claim 1 which is 3-(o-fluorophenyl)-N,N,α,4-tetramethylpyrazole-1-acetamide.

86. A compound according to claim 1 which is 3-(o-bromophenyl)-N,N-diethyl-α,4-dimethylpyrazole-1-acetamide.

87. A compound according to claim 1 which is 3-(o-bromophenyl)-α-ethyl-N,N,4-trimethylpyrazole-1-acetamide.

88. A compound according to claim 1 which is 3-(2,4-dichlorophenyl)-N,N,α,4-tetramethylpyrazole-1-acetamide.

89. A compound according to claim 1 which is 4-ethyl-N,N,α,α-tetramethyl-3-phenylpyrazole-1-acetamide.

90. A compound according to claim 1 which is 3-(o-chlorophenyl)-4-ethyl-N,N,α,α-tetramethylpyrazole-1-acetamide.

91. A compound according to claim 1 which is 4-bromo-N,N,α,α-tetramethyl-3-phenylpyrazole-1-acetamide.

92. A compound according to claim 1 which is 3-(o-bromophenyl)-N,N,α,α,4-pentamethylpyrazole-1-acetamide.

93. A compound according to claim 1 which is 4-cyano-N,N,α,α-tetramethyl-3-phenylpyrazole-1-acetamide.

94. A compound according to claim 1 which is 3-(o-methoxyphenyl)-N,N,α,α-tetramethylpyrazole-1-acetamide.

95. A compound according to claim 1 which is N,N,α,α-tetramethyl-3-phenyl-4-isopropylpyrazole-1-acetamide.

96. A compound according to claim 1 which is N,Nα,α-tetramethyl-3-phenyl-4-propylpyrazole-1-acetamide.

97. A compound according to claim 1 which is 3-(2,4-dichlorophenyl)-N,N,α,α,4-pentamethylpyrazole-1-acetamide.

98. A compound according to claim 1 which is 3-(2,5-dichlorophenyl)-N,N,α,α,4-pentamethylpyrazole-1-acetamide.

99. A compound according to claim 1 which is 3-(o-cyanophenyl)-N,N,α,α,4-pentamethylpyrazole-1-acetamide.

100. A compound according to claim 1 which is 3-(o-bromophenyl)-N,N,α,4-tetramethylpyrazole-1-acetamide.

101. A compound according to claim 1 which is 3-(o-fluorophenyl)-N,N,α,α,4-pentamethylpyrazole-1-acetamide.

102. A compound according to claim 1 which is 3-(o-cyanophenyl)-N,N,α,4-tetramethylpyrazole-1-acetamide.

103. A compound according to claim 1 which is 4-ethylthio-N,N,α,α,-tetramethyl-3-phenylpyrazole-1-acetamide.

104. A compound according to claim 1 which is 3-(o-chlorophenyl)-N,N,α,α-tetramethyl-4-isopropylpyrazole-1-acetamide.

105. A compound according to claim 1 which is 3-(o-chlorophenyl)-N,N,α,α-tetramethyl-4-propylpyrazole-1-acetamide.

106. A compound according to claim 1 which is 3-(o-chlorophenyl)-N,N,α,α,4-tetramethylpyrazole-1-acetamide.

107. A compound according to claim 1 which is 3-(o-chlorophenyl)-N,N-diethyl-α,α,4-trimethylpyrazole-1-acetamide.

108. A compound according to claim 1 which is 4-methoxy-N,N,α,α-tetramethyl-3-phenylpyrazole-1-acetamide.

109. A compound according to claim 1 which is 3-(o-methoxyphenyl)-N,N,α,α,4-pentamethylpyrazole-1-acetamide.

110. A compound according to claim 1 which is 3-(o-chlorophenyl)-N,N-diethyl-α,4-dimethylpyrazole-1-acetamide.

111. A compound according to claim 1 which is 3-(o-chlorophenyl-N,N,α,4-tetramethyl-α-phenylpyrazole-1-acetamide.

112. A compound according to claim 1 which is 3-(2,6-dichlorophenyl)-N,N,α,4-tetramethylpyrazole-1-acetamide.

113. A compound according to claim 1 which is 3-(2,6-dichlorophenyl)-N,N,α,α,4-pentamethylpyrazole-1-acetamide.

114. A compound according to claim 1 which is 3-(o-bromophenyl)-4-ethyl-N,N,α,α-tetramethylpyrzole-1-acetamide.

115. A compound according to claim 1 which is 4-ethyl-3-(o-fluorophenyl)-N,N,α,α-tetramethylpyrazole-1-acetamide.

116. A compound according to claim 1 which is N,N,-dimethyl-1-[(3-o-chlorophenyl)-4-methylpyrazol-1-yl]cyclopropanecarboxamide.

117. A compound according to claim 1 which is N,N,dimethyl-1-[(3-o-chlorophenyl)-4-ethylpyrazol-1-yl]cyclopropanecarboxamide.

118. A compound according to claim 1 which is 3-o-ethylphenyl)-N,N,α,α,4-pentamethylpyrazole-1-acetamide.

119. A compound according to claim 1 which is N,N,α,α,4-pentamethyl-3-(o-isopropylphenyl)pyrazole-1-acetamide.

120. A compound according to claim 1 which is 3-(o-iodophenyl)-N,N,α,α,4-pentamethylpyrazole-1-acetamide.

121. A method for controlling weeds or undesirable vegetation which comprises applying to the locus thereof a herbicidally effective amount of a compound of the formula:

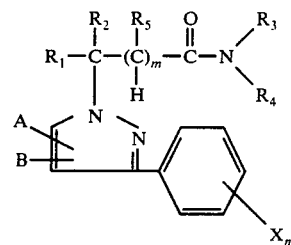

where $R_1$, $R_2$, $R_3$, $R_4$, $R_5$, $m$, X, $n$, A and B are as defined in claim 1.

122. A composition for herbicidal use comprising an inert adjuvant and, as the active ingredient, an effective amount of a compound of the formula:

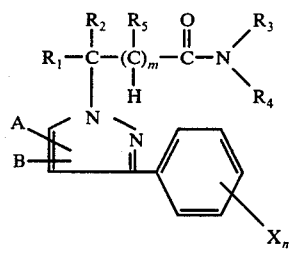

where $R_1$, $R_2$, $R_3$, $R_4$, $R_5$, $m$, X, $n$, A and B are as defined in claim 1.

* * * * *